US011248254B2

(12) United States Patent
Dambacher et al.

(10) Patent No.: US 11,248,254 B2
(45) Date of Patent: Feb. 15, 2022

(54) METHOD AND SYSTEM EMPLOYING DISTINGUISHABLE POLYMERASES FOR DETECTING TERNARY COMPLEXES AND IDENTIFYING COGNATE NUCLEOTIDES

(71) Applicant: Omniome, Inc., San Diego, CA (US)

(72) Inventors: Corey M. Dambacher, La Jolla, CA (US); Devon Cayer, Del Mar, CA (US); Richard LeCoultre, San Diego, CA (US); Joseph Rokicki, San Diego, CA (US); Kerry Wilson, La Jolla, CA (US); Eugene Tu, San Diego, CA (US); Kandaswamy Vijayan, San Diego, CA (US)

(73) Assignee: OMNIOME, INC., San Diego, CA (US)

( * ) Notice: Subject to any disclaimer, the term of this patent is extended or adjusted under 35 U.S.C. 154(b) by 373 days.

(21) Appl. No.: 15/851,383

(22) Filed: Dec. 21, 2017

(65) Prior Publication Data
US 2018/0187245 A1 Jul. 5, 2018

Related U.S. Application Data

(60) Provisional application No. 62/440,624, filed on Dec. 30, 2016.

(51) Int. Cl.
| | | |
|---|---|---|
| *C12Q 1/68* | (2018.01) | |
| *C12Q 1/6816* | (2018.01) | |
| *C12Q 1/6869* | (2018.01) | |
| *C12Q 1/6874* | (2018.01) | |
| *C12Q 1/6827* | (2018.01) | |

(52) U.S. Cl.
CPC ......... *C12Q 1/6816* (2013.01); *C12Q 1/6827* (2013.01); *C12Q 1/6869* (2013.01); *C12Q 1/6874* (2013.01)

(58) Field of Classification Search
USPC .......... 435/6.1, 6.11, 6.12, 91.1, 91.2, 91.51, 435/283.1, 287.1, 287.2; 436/94, 501; 536/23.1, 24.3, 24.33, 25.3, 25.32
See application file for complete search history.

(56) References Cited

U.S. PATENT DOCUMENTS

| | | | |
|---|---|---|---|
| 5,302,509 | A | 4/1994 | Cheeseman |
| 5,614,365 | A | 3/1997 | Tabor et al. |
| 6,485,909 | B1 | 11/2002 | Hong et al. |
| 6,720,177 | B2 | 4/2004 | Ghadiri et al. |
| 6,828,094 | B2 | 12/2004 | Kilger et al. |
| 6,908,736 | B1 | 6/2005 | Densham |
| 7,008,766 | B1 | 3/2006 | Densham et al. |
| 7,057,026 | B2 | 6/2006 | Barnes et al. |
| 7,223,540 | B2 | 5/2007 | Pourmand et al. |
| 7,264,934 | B2 | 9/2007 | Fuller et al. |
| 7,329,492 | B2 | 2/2008 | Hardin et al. |
| 7,414,116 | B2 | 8/2008 | Liu et al. |
| 7,427,673 | B2 | 9/2008 | Balasubramanian et al. |
| 7,449,297 | B2 | 11/2008 | Freije et al. |
| 7,482,120 | B2 | 1/2009 | Buzby et al. |
| 7,544,794 | B1 | 6/2009 | Benner et al. |
| 7,604,963 | B2 | 10/2009 | Densham et al. |
| 7,635,578 | B2 | 12/2009 | Li et al. |
| 7,713,698 | B2 | 5/2010 | Li et al. |
| 7,790,869 | B2 | 9/2010 | Li et al. |
| 7,871,771 | B2 | 1/2011 | Fuller et al. |
| 7,939,264 | B1 | 5/2011 | Densham et al. |
| 7,956,171 | B2 | 6/2011 | Siddiqi et al. |
| 8,034,923 | B1 | 10/2011 | Benner et al. |
| 8,071,755 | B2 | 12/2011 | Efcavitch et al. |
| 8,088,575 | B2 | 1/2012 | Li et al. |
| 8,133,672 | B2 | 3/2012 | Bjornson et al. |
| 8,236,532 | B2 | 8/2012 | Eltoukhy et al. |
| 8,298,792 | B2 | 10/2012 | Meng et al. |
| 8,399,196 | B2 | 3/2013 | Hoser et al. |
| 8,481,266 | B2 | 7/2013 | Shao et al. |
| 8,535,881 | B2 | 9/2013 | Schneider et al. |
| 8,603,741 | B2 | 12/2013 | Emig et al. |
| 8,632,975 | B2 | 1/2014 | Vander Horn et al. |

(Continued)

FOREIGN PATENT DOCUMENTS

| | | |
|---|---|---|
| EP | 1115848 | 7/2001 |
| WO | 1990/013666 | 11/1990 |

(Continued)

OTHER PUBLICATIONS

"Primer (molecular biology)" from Wikipedia. Printed on Apr. 23, 2021.*
PCT/US2017/067976, "International Search Report and Written Opinion", dated Mar. 14, 2018, 13 pages.
Previte et al., "DNA Sequencing Using Polymerase Substrate-binding Kinetics", Nature Communication, vol. 6, Jan. 23, 2015, 12 pages.
PCT/US2017/067976, "International Preliminary Report on Patentability", dated Jul. 11, 2019, 9 pages.
Agnarsson et al., "On-chip modulation of evanescent illumination and live-cell imaging with polymer waveguides." Optics Express, Nov. 7, 2011, vol. 19, No. 23: 22929-22935.

(Continued)

*Primary Examiner* — Frank W Lu
(74) *Attorney, Agent, or Firm* — Kilpatrick Townsend and Stockton LLP

(57) ABSTRACT

Method of identifying a cognate nucleotide (i.e., the "next correct nucleotide") for a primed template nucleic acid molecule. In some embodiments, an ordered or random array of primed target nucleic acids characterized by different cognate nucleotides can be evaluated using a single imaging step to identify different cognate nucleotides for a collection of different primed template nucleic acid molecules. An optional incorporation step can follow the identifying step. A polymerase different from the ones used in the binding and examination steps can be used to incorporate a nucleotide, such as a reversible terminator nucleotide, preliminary to identification of the next cognate nucleotide.

21 Claims, 5 Drawing Sheets

(56) References Cited

U.S. PATENT DOCUMENTS

| | | | |
|---|---|---|---|
| 8,658,365 B2 | 2/2014 | Bjornson et al. | |
| 8,703,461 B2 | 4/2014 | Peris et al. | |
| 8,808,989 B1 | 8/2014 | Siddiqi et al. | |
| 8,911,972 B2 | 12/2014 | Chaisson et al. | |
| 8,986,930 B2 | 3/2015 | Fedorov et al. | |
| 9,255,258 B2 | 2/2016 | Luo et al. | |
| 9,279,155 B2 | 3/2016 | Bjornson et al. | |
| 9,279,154 B2 | 6/2016 | Previte et al. | |
| 9,399,798 B2 | 7/2016 | Morris et al. | |
| 2003/0049635 A1* | 3/2003 | Sommer | C12Q 1/6827 435/6.11 |
| 2004/0005599 A1* | 1/2004 | Schoenbrunner | C12N 9/1252 435/6.11 |
| 2006/0051807 A1 | 3/2006 | Fuller | |
| 2006/0292583 A1 | 12/2006 | Schneider et al. | |
| 2007/0009925 A1 | 1/2007 | Fang et al. | |
| 2008/0124768 A1* | 5/2008 | Mueller | C12N 9/1252 435/91.1 |
| 2009/0061447 A1 | 3/2009 | Schneider et al. | |
| 2010/0316999 A1 | 12/2010 | Densham et al. | |
| 2010/0317012 A1 | 12/2010 | Ju et al. | |
| 2011/0008794 A1 | 1/2011 | Schneider et al. | |
| 2011/0160077 A1 | 6/2011 | Chaisson et al. | |
| 2011/0237464 A1 | 9/2011 | Cunningham et al. | |
| 2013/0165328 A1 | 6/2013 | Previte et al. | |
| 2014/0127680 A1 | 5/2014 | Emig et al. | |
| 2014/0234940 A1 | 8/2014 | Peris et al. | |
| 2016/0010150 A1 | 1/2016 | Emig et al. | |
| 2016/0168633 A1 | 6/2016 | Previte et al. | |
| 2016/0177384 A1 | 6/2016 | Bjornson et al. | |
| 2016/0208318 A1 | 7/2016 | Vander Horn et al. | |
| 2017/0022553 A1 | 1/2017 | Vijayan et al. | |
| 2017/0292157 A1 | 10/2017 | Drmanac | |
| 2017/0314064 A1 | 11/2017 | Iyidogan et al. | |

FOREIGN PATENT DOCUMENTS

| | | |
|---|---|---|
| WO | 9106678 | 5/1991 |
| WO | 9506138 | 3/1995 |
| WO | 2001/016375 | 3/2001 |
| WO | 0116375 | 3/2001 |
| WO | 2002/04680 | 1/2002 |
| WO | 2005/121363 | 12/2005 |
| WO | 2007048033 | 4/2007 |
| WO | 2007123744 | 11/2007 |
| WO | 2009061911 | 5/2009 |
| WO | 2009145820 | 12/2009 |
| WO | 2010/068884 | 6/2010 |
| WO | 2010/111690 | 9/2010 |
| WO | 2010141390 | 12/2010 |
| WO | 2011/159942 | 12/2011 |
| WO | 2011159942 | 12/2011 |
| WO | 2012/166742 | 12/2012 |
| WO | 2013/096692 | 6/2013 |
| WO | 2014114665 | 7/2014 |
| WO | 2016071689 | 5/2016 |
| WO | 2017014762 | 1/2017 |
| WO | 2017117235 | 7/2017 |
| WO | 2017184996 | 10/2017 |
| WO | 2018/034780 | 2/2018 |

OTHER PUBLICATIONS

Anker et al., "Biosensing with Plasmonic Nanosensors", Nature Materials 7, No. 6, Jun. 2008, 442-453.

Bandwar and Patel, "Peculiar 2-Aminopurine Fluorescence Monitors the Dynamics of Open Complex Formation by Bacteriophage T7 RNA Polymerase." The Journal of Biological Chemistry, vol. 275, No. 17, Issue of 27: 14075-14082, 2001.

Brockman et al., "A Multistep Chemical Modification Procedure to Create DNA Arrays on Gold Surfaces for the Study of Protein— DNA Interactions with Surface Plasmon Resonance Imaging", Journal of the American Chemical Society 121, Sep. 1999, 8044-8051.

Brown et al., "Pre-Steady-State Kinetic Analysis of Truncated and Full-Length *Saccharomyces cerevisiae* DNA Polymerase Eta", Journal of Nucleic Acids, 2010, Article ID 871939, 11 pages.

Campagnola et al., "High-throughput Screening Identification of Poliovirus RNA-dependent RNA Polymerase Inhibitors." Antiviral Res. Sep. 2011; 91(3):241-251.

Chan et al., "A general method for discovering inhibitors of protein-DNA interactions using photonic crystal biosensors." ACS Chem Biol. Jul. 18, 2008; 3(7): 437-448.

Chen et al., "The History and Advances of Reversible Terminators Used in New Generations of Sequencing Technology", Genomics Proteomics Bioinformatics, 11(1), Feb. 1, 2013, pp. 34-40.

Chin et al., "The Effect of Divalent Nickel (Ni2+) on in Vivo DNA Replication by DNA Polymerase α1", Cancer Research, May 1, 1994, 2337-2341, vol. 54.

Choi, et al., "EML4-ALK Mutations in Lung Cancer that Confer Resistance to ALK Inhibitors." N. Engl. J. Med. (2010)18:1734-1739.

Concepcion, "Label-Free Detection of Biomolecular Interactions Using BioLayer Interferometry for Kinetic Characterization." Combinatorial Chemistry and High Throughput Screening. 2009, 12(8):791-800.

Crumpacker, "Mechanism of action of foscarnet against viral polymerases." American Journal of Medicine, Feb. 14, 1992, vol. 92, Issue 2, Supplement 1, pp. S3-S7.

Datta, "Salt Dependence of DNA binding by Thermus aquaticus and *Escherichia coli* DNA Polymerases", Journal of Biological Chemistry, vol. 278, Issue of Feb. 21, 2003: 5694-5701.

Deredge et al., "The Glutamate Effect on DNA Binding by Pol I DNA Polymerases: Osmotic Stress and the Effective Reversal of Salt Linkage", J. Mol. Biol., vol. 401, 2010, 223-238.

Doublie et al., "An open and closed case for all polymerases", Doublie, Sawaya, Ellenberger, "An open and closed case for all polymerases", Structure, Feb. 1999, 7:R31-R35.

Dunlap and Tsai, "Use of 2-Aminopurine and Tryptophan Fluorescence as Probes in Kinetic Analyses of DNA Polymerase Beta." Biochemistry, 2002, 41: 11226-11235.

Dzantiev, "A conformational change in *E. coli* DNA polymerase I (Klenow fragment) is induced in the presence of a dNTP complementary to the template base in the active site", Biochemistry, 2000, 39(2):356-361.

Eriksson et al., "Pyrophosphate analogues as inhibitors of DNA polymerases of cytomegalovirus, herpes simplex virus and cellular origin", Biochimica et Biophysica Acta (1982), 696(2): 115-123.

Espinoza-Herrera et al., "Following DNA Chain Extension and Protein Conformational Changes in Crystals of a Y-Family DNA Polymerase via Raman Crystallography", Biochemistry, Jul. 23, 2013, 52(29).

Fang, et al., "Genome-wide mapping of methylated adenine residues in pathogenic *Escherichia coli* using single-molecule real-time sequencing." Dec. 2012, vol. 30, No. 12, 1232-1243.

Favicchio et al., "Fluorescence Spectroscopy and Anisotrophy in the analysis of DNA-Protein Interactions." Methods in Molecular Biology, DNA-Protein Interactions, vol. 543, 2009, 589-611.

Federley, "New insights into the mechanism of dna replication on unmodified and benzo[a]pyrene modified templates using surface plasmon resonance", Wayne State University Dissertations, 2011, Paper 235.

Fuller et al., "The challenges of Sequencing by synthesis." Nature Biotechnology, vol. 27, No. 11, Nov. 2009, pp. 1013-1023.

Gralla et al., "Potassium Glutamate as A Transcriptional Inhibitor During Bacterial Osmoregulation", The EMBO Journal, vol. 25, No. 7, 2006, pp. 1515-1521.

Horn et al., "EML4-ALK: Honing In on a New Target in Non-Small-Cell Lung Cancer." Journal of Clinical Oncology. Sep. 10, 2009. vol. 27, No. 26, p. 4232-4235.

Hoshino et al., "Effect of Ultrasound on DNA Polymerase Reactions: Monitoring on a 27-MHz Quartz Crystal Microbalance." Biomacromolecules, 2006, 7(3), pp. 682-685.

Hutter et al., "Labeled Nucleoside Triphosphates with Reversibly Terminating Aminoalkoxyl Groups", vol. 29, Issue 11-12, 2010.

(56) References Cited

OTHER PUBLICATIONS

Ion Torrent, "Ion Torrent Amplicon Sequencing", Internet, Available at http://iontorrent.com/lib/images/PDFs/amplicon_application_note_040411.pdf, Apr. 4, 2011, pp. 1-5.
Jindal et al., "Suramin affects DNA Synthesis in HeLa Cells by Inhibition of DNA Polymerases." Cancer Research, Dec. 15, 1990, 50:7754-7757.
Jochmans et al., "Indolopyridones Inhibit Human Immunodeficiency Virus Reverse Transcriptase with a Novel Mechanism of Action." Journal of Virology, Dec. 2006, vol. 80, No. 24: 12283-12292.
Kaplan, "Photolabile chelators for the rapid photorelease of divalent cations." Proc. Natl. Acad. Sci. USA, Sep. 1988, vol. 85: 6571-6575.
Kaushik et al., "Biochemical Analysis of Catalytically Crucial Aspartate Mutants of Human Immunodeficiency Virus Type 1 Reverse Transcriptase", Biochemistry, 35, 1996, 11536-11546.
Kim, "An FET-type charge sensor for highly sensitive detection of DNA sequence", Biosensors and Bioelectronics, Microsensors and Microsystems 2003, 20, No. 1, Jul. 30, 2004, 69-74.
Klenow et al., "Effect of Monovalent Cations on the Activity of the DNA Polymerase of *Escherichia coli* B", European J. Biochem., 1696, 133-141.
Kumar, et al., "Altered Order of Substrate Binding by DNA Polymerase X from African Swine Fever Virus." Biochemistry 2008: 7875-7887.
Leinbach et al., "Mechanism of phosphonoacetate inhibition of herpesvirus-induced DNA polymerase." Biochemistry, 1976, 15(2), pp. 426-430.
Lutz et al. "An in vitro screening technique for DNA polymerases that can incorporate modified nucleotides. Pseudothymidine as a substrate for thermostable polymerases." Nucleic Acids Research, 1999, vol. 27, No. 13: 2792-2798.
Maga et al., "HIV-1 RT Inhibitors with a Novel Mechanism of Action: NNRTIs that Compete with the Nucleotide Substrate." Viruses 2010, 2(4): 880-899.
Maga et al., "Selective Interaction of the Human Immunodeficiency Virus Type 1 Reverse Transcriptase Nonnucleoside Inhibitor Efavirenz and Its Thio-Subsitituted Analog with Different Enzyme-Substrate Complexes." Antimicrobial Agents and Chemotherapy, May 2000, 44, 1186-1194.
Mano, "Non-solid oncogenes in solid tumors: EML4-ALK fusion genes in lung cancer", (2008), Cancer Sci., 99:2349-2355.
Markiewicz et al., "Single-Molecule Microscopy Reveals New Insights into Nucleotide Selection by DNA Polymerase I", Nucleic Acids Research, vol. 40, No. 16, Jun. 4, 2012, pp. 7975-7984.
Masheyekhi et al., "Analysis of Read-Length Limiting Factors in Pyrosequencing Chemistry." Anal Biochem. Apr. 15, 2007; 363(3): 275-287.
Maxwell et al., "DNA Lesion Alters Global Conformational Dynamics of Y-family DNA Polymerase during Catalysis", The Journal of Biological Chemistry, vol. 287, No. 16, Apr. 13, 2012, pp. 13040-13047.
Namasivayam, "Light-Induced Molecular Cutting: Localized Reaction on a Single DNA Molecule." Anal. Chem. 2003, 75: 4118-4194.
Nath, "Label free colorimetric biosensing using nanoparticles", Jul. 2004; 14(4):377-89.
Nazirizadeh, "Low-cost label-free biosensors using photonic crystals embedded between crossed polarizers", Optics Express, vol. 18, No. 18, Aug. 30, 2010, 19120-19128.
Nikiforov, "Oligonucleotides labeled with single flurophores as sensors for deoxynucleotide triphosphate binding by DNA polymerases." Analytical Biochemistry 444 (2014): 60-66.
Patel, "Insights into DNA Polymerization Mechanisms from Structure and Function Analysis of HIV-1 Reverse Transcriptase.", Biochemistry 34, 1995, 5351-5363.
Peletskaya et al. "Cross-Linking of the Figners Subdomain of Human Immunodeficiency Virus Type 1 Reverse Transcriptase to Template-Primer." Journal of Virology, Oct. 2001, vol. 75, No. 19: 9435-9445.
Pitta et al., "Synthesis and HIV-1 RT inhibitory action of novel (4/6-substituted benzo[d]thiazol-2-yl) thiazolidin-4-ones. Divergence from the non-competitive inhibition mechanism." J. Enzyme Inhib. Med. Chem. 28(10):113-122(2013).
Potapova et al., "Interaction of dNTP, pyrophosphate and their analogs with the dNTP-binding sites of *E. coli* DNA polymerase I Klenow fragment and human DNA polymerase." Dec. 17, 1990, vol. 277, Issues 1-2, pp. 194-196.
Ren et al., "Inhibition of Klenow DNA polymerase and poly(A)-specific ribonuclease by aminoglycosides." RNA (2002), 8:1393-1400.
Richard, A. J. et al., "Thermal stability landscape for Klenow DNA polymerase as a function of pH and salt concentration," Biochemica et Biophysica Acta, 2006, vol. 1764, pp. 1546-1552.
Roettger et al., "Mismatched and Matched dNTP Incorporation by DNA Polymerase β Proceed via Analogues Kinetic Pathways", Biochemistry, 47, Sep. 16, 2008, pp. 9718-9727.
Santoso et al., "Conformational transitions in DNA polymerase I revealed by single-molecule FRET", Proceedings of the National Academy of Sciences, vol. 107, No. 2, Jan. 12, 2010, pp. 715-720.
Schadt et al., "Modeling Kinetic rate variation in thrid generation DNA sequencing data to detect putative modifications to DNA bases." Genome Research, 2013:129-141.
Schultz et al., "Single-target molecule detection with nonbleaching multicolor optical immunolabels", PNAS, vol. 96, No. 3, Feb. 1, 2000, 996-1001.
Sen, "Intrinsic fluorescence of *E. coli* RNA polymerase as a probe for its conformational changes during transcription initiation", Biochem Biophys Res Commun. Jun. 15, 1994; 201(2):820-8.
Soda et al., "Identification of the transforming EML4-ALK fusion gene in non-small-cell lung cancer." Aug. 2, 2007. vol. 448:561-566, Nature.
Star et al., "Electronic Detection of Specific Protein Binding Using Nanotube FET Devices", Nano Letters 3, No. 4, Apr. 1, 2003, 459-463.
Su, "Surface Plasmon Resonance Spectroscopy and Quartz Crystal Microbalance Study of Streptavidin Film Structure effects on Biotinylated DNA Assembly and Target DNA Hybridization." Langmuir, 2005, 21(1), pp. 348-353.
Tsai, "Dissertation", May 2005, pp. 1-131.
Tsai et al., "Site-Specific Labeling of T7 DNA Polymerase with a conformationally Sensitive Fluorophore and Its Use in Detecting Single-Nucleotide Polymorphisms", Analytical Biochemistry 384, No. 1, Jan. 1, 2009, pp. 136-144.
Vaidyanathan, "Binary and ternary binding affinities between exonuclease-deficient Klenow fragment (Kf-exo(−)) and various arylamine DNA lesions characterized by surface plasmon resonance.", Chem Res Toxicol. Aug. 20, 2012; 25(8): 1568-1570.
Vaidyanathan et al., "Binding kinetics of DNA-protein interaction using surface plasmon resonance", Protocol Exchange, May 22, 2013.
Vollmer, "Whispering-gallery-mode biosensing: label-free detection down to single molecules.", Nature Methods, vol. 5, No. 7, Jul. 2008:591-596.
Walsh, "Synthetic Nucleotides as Probes of DNA Polymerase Specificity", Journal of Nucleic Acids, vol. 2012, Article ID 530963, 17 pages.
Washington et al., "Human DNA Polymerase Utilizes Different Nucleotide Incorporation Mechanisms Dependent upon the Template Base", Molecular and Cellular Biology, vol. 24, No. 2, Jan. 2004, 936-943.
Xia et al., "DNA Mismatch Synthesis Complexes Provide Insights into Base Selectivity of a B family DNA Polymerase", J Am Chem Soc. 135(1), Jan. 9, 2013, 193-202.
Yuzenkova et al., "Tagetitoxin inhibits transcription by stabilizing pre-translocated state of the elongation complex." Nucleic Acids Research, 2013:1-9.
"APCH231: Chemical Analysis Complexometric Titrations EDTA", Notes compiled by Dr. C. Southway, Available Online At: (http://cheminnerweb.ukzn.ac.za/libraries/apch231_h_govender_s_notes/apch231_edta.sflb.ashx), post date of Nov. 23, 2015, pp. 30-42.

(56) References Cited

OTHER PUBLICATIONS

Engtröm et al., "A Label-Free Continuous Total-Internal-Reflection-Fluorescence-Based Immunosensor", Analytical Biochemistry, vol. 357, No. 2, Oct. 15, 2006, pp. 159-166.
Escobedo et al., "Integrated Nanohole Array Surface Plasmon Resonance Sensing Device Using a Dual-Wavelength Source", Journal of Micromechanics and Microengineering, vol. 21, No. 11, Oct. 2011, pp. 1-6.
Puttaswamy, "Optical Method for Measuring Spatial pH Change on Conductive Microelectrodes", Submitted in fulfillment for the International Master's Program (IMP) Nanomaterials and Nanotechnology, KTH, Royal Institute of Technology, Stockholm, Sweden, 2007, pp. 1-66.
EP17835535.0, "Office Action", dated Sep. 8, 2020, 4 pages.
CA3,048,415, "Office Action", dated Jun. 10, 2020, 5 pages.
AU2017386515, "First Examination Report", dated Oct. 12, 2020, 4 pages.
CA3,048,415, "Office Action", dated Apr. 22, 2021, 3 pages.

\* cited by examiner

METHOD AND SYSTEM EMPLOYING DISTINGUISHABLE POLYMERASES FOR DETECTING TERNARY COMPLEXES AND IDENTIFYING COGNATE NUCLEOTIDES

RELATED APPLICATION

This application claims the benefit of U.S. Provisional Application No. 62/440,624, filed Dec. 30, 2016. The entire disclosure of this earlier application is hereby incorporated by reference.

TECHNICAL FIELD

The present disclosure generally relates to the field of biotechnology. More specifically, the disclosure concerns a Sequencing By Binding™ method and system employing binding complexes that are distinguished from each other.

BACKGROUND

The advent of automated nucleic acid sequencing platforms has brought with it a need for sequencing chemistries that can be performed with exceedingly high efficiency at each of several discrete steps over many cycles of nucleotide identification. High throughput platforms conventionally employ target nucleic acids immobilized in a flow cell (e.g., on a bead or generated in situ). Certain approaches rely upon template-dependent incorporation of nucleotide analogs by polymerase enzymes, where the incorporation efficiency is measurably less than 100% per cycle. These approaches can further involve removal of a portion of the nucleotide analog molecule, but sometimes result in extended primers containing a chemical remnant (sometimes called a "scar") of the analog that is not characteristic of native nucleic acid. Accumulation of these chemical scars can inhibit correct and efficient downstream nucleotide incorporation, thereby compromising integrity of the nucleic acid chemistry.

To overcome this liability, various approaches have been pursued to leave primers with a native structure during at least one phase of the cycling routine. In some instances, detectable labels and reversible terminator moieties have been joined to the incoming nucleotide using multiple linkages that may be cleaved by a so-called "scarfree" mechanism. Efficient and complete removal of these linkages can provide good results, but can also add increased cost, time and/or complexity to the sequencing workflow. Again, this complexity arises from procedures that incorporate labeled nucleotides.

Even in view of the many successes that have been achieved with next-generation sequencing platforms, there remains a need for techniques that can be used for determining nucleic acid sequences in a manner that maintains a structure similar to natural nucleic acid, and that permits simple data processing to make correct nucleotide calls in a reliable fashion.

SUMMARY OF THE DISCLOSURE

Figure 1:
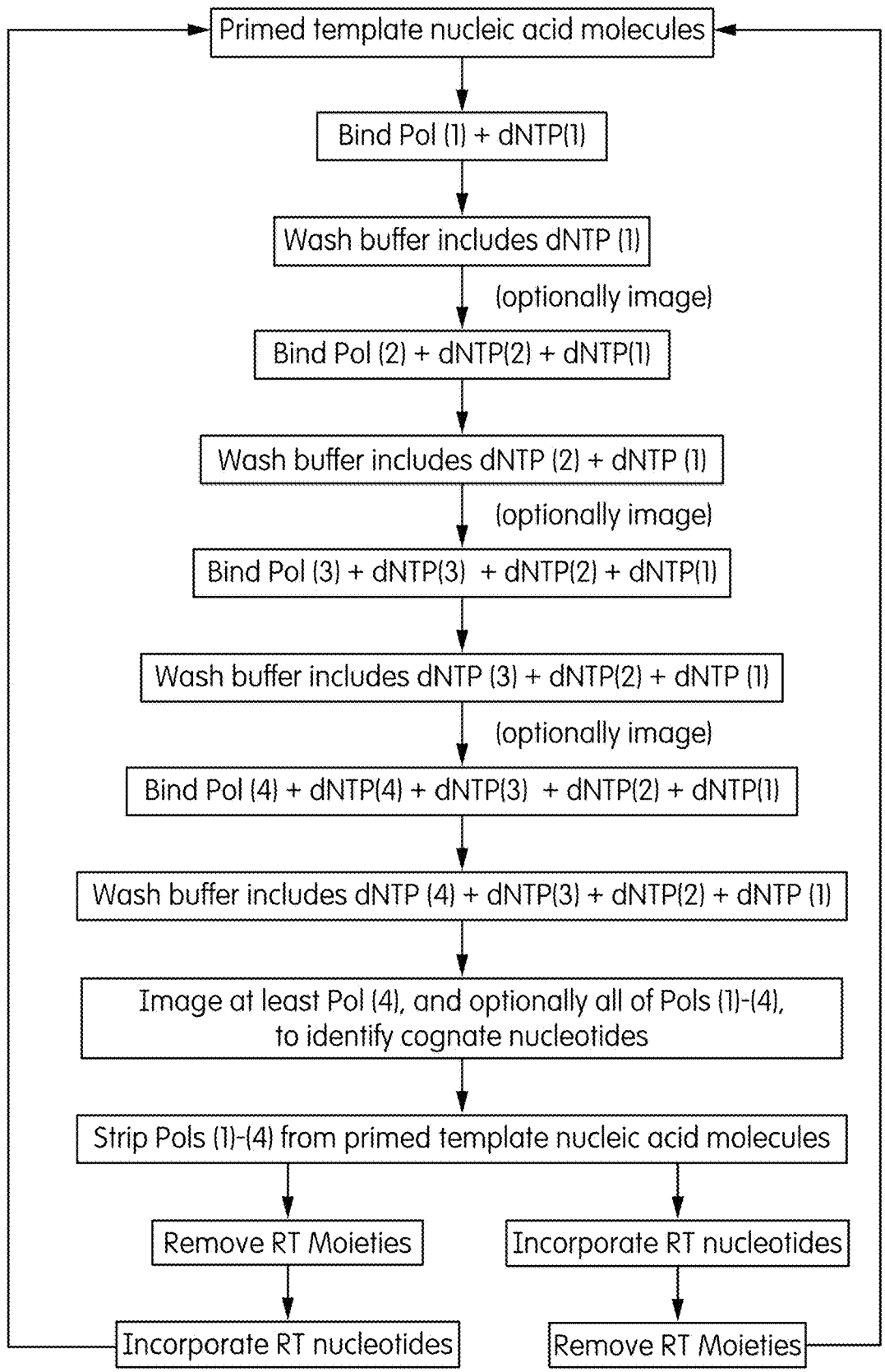
FIG. 1 is a schematic flow diagram illustrating sequential steps in a procedure that identifies cognate nucleotides and increments the primed template nucleic acid by single-base extension. Notably, subsequently performed binding steps omit the polymerases used in previous binding steps in the cycle of determining cognate nucleotide identity. The flow diagram illustrates how each binding step employs a unique combination of polymerase and nucleotide(s). Buffers used in wash steps also can omit polymerases.

In one aspect, the disclosure relates to a method of distinguishing nucleic acids. The method includes the step of (a) providing a first mixture including a population of different primed template nucleic acids and a first stabilized ternary complex, the first stabilized ternary complex including a first primed template nucleic acid of the mixture, a polymerase that is attached to a first type of label, and a first type of nucleotide. There also is the step of (b) forming a second stabilized ternary complex by contacting the first mixture with a reagent including a second type of nucleotide and a polymerase attached to a second type of label that is different from the first type of label, the second stabilized ternary complex including a second primed template nucleic acid of the first mixture, a polymerase of the reagent, and a second type of nucleotide of the reagent, thereby forming a second mixture including the first and second stabilized ternary complexes. There also is the step of (c) detecting the first and second type of label to distinguish the first primed template nucleic acid from the second primed template nucleic acid. According to one generally preferred embodiment, the first type of label is covalently attached to the polymerase of the first stabilized ternary complex. When this is the case, the second type of label can be covalently attached to the polymerase of the second stabilized ternary complex. According to another generally preferred embodiment, the first and second types of nucleotides are not distinguishably labeled with respect to each other. When this is the case, both the first and second types of nucleotides can be unlabeled nucleotides. According to another generally preferred embodiment, the method further includes a step of removing free polymerases from the first mixture between steps (a) and (b). For example, the removing step can involve contacting the first mixture with a wash solution that includes the first type of nucleotide. Alternatively, when the method includes the step of removing free polymerases from the first mixture between steps (a) and (b), the method can further include a step for removing free polymerases from the second mixture between steps (b) and (c). More preferably, the removing step can involve contacting the second mixture with a wash solution that includes the first and second types of nucleotides. According to another generally preferred embodiment, the population of different primed template nucleic acids can be attached to a solid support. According to another generally preferred embodiment, the first reagent can further include the first type of nucleotide. According to another generally preferred embodiment, the first type of nucleotide is not covalently attached to the primed template nucleic acid in the first stabilized ternary complex of the second mixture, and the second type of nucleotide is not covalently attached to the primed template nucleic acid in the second stabilized ternary complex of the second mixture. According to another generally preferred embodiment, the method can further include the steps of: (d) forming a third stabilized ternary complex by contacting the second mixture with a second reagent that includes a third type of nucleotide and a polymerase that is attached to a third type of label that is different from the first and second types of labels, the third stabilized ternary complex including a third primed template nucleic acid of the second mixture, a polymerase of the second reagent, and a third type of nucleotide of the second reagent, thereby forming a third mixture including the first, second and third stabilized ternary complexes; and (e) detecting the third type of label to distinguish the third primed template nucleic acid from the first and second primed template nucleic acids. When this is the case, the third type of label can be covalently attached to the polymerase of the third stabilized ternary complex. Alternatively, the first, second and third types of nucleotides are not distinguishably labeled with respect to each other. Alternatively, the method can further include a step for removing free polymerases from the second mixture between steps (b) and (d). More preferably, the removing step can involve contacting the second mixture with a wash solution that includes the first and second types of nucleotides. Alternatively, the method further includes a step of removing free polymerases from the third mixture between steps (d) and (e). More preferably, the removing includes contacting the third mixture with a wash solution including the first, second and third types of nucleotides. According to a different alternative, the second reagent further includes the second type of nucleotide. According to yet a different alternative, the first type of nucleotide is not covalently attached to the primed template nucleic acid in the first stabilized ternary complex of the third mixture; the second type of nucleotide is not covalently attached to the primed template nucleic acid in the second stabilized ternary complex of the third mixture, and the third type of nucleotide is not covalently attached to the primed template nucleic acid in the third stabilized ternary complex of the third mixture. According to still yet a different alternative, the method further includes the steps of: (f) forming a fourth stabilized ternary complex by contacting the third mixture with a third reagent including a fourth type of nucleotide and a polymerase that is attached to a fourth type of label that is different from the first, second and third types of labels, the fourth stabilized ternary complex including a fourth primed template nucleic acid of the third mixture, a polymerase of the third reagent, and a fourth type of nucleotide of the third reagent, thereby forming a fourth mixture including the first, second, third and fourth stabilized ternary complexes; and (g) detecting the fourth type of label to distinguish the fourth primed template nucleic acid from the first, second and third primed template nucleic acids. For example, the fourth type of label can be covalently attached to the polymerase of the fourth stabilized ternary complex. Alternatively, the first, second, third and fourth types of nucleotides are not distinguishably labeled with respect to each other. Alternatively, the method can further include a step for removing free polymerases from the third mixture between steps (d) and (f). More preferably, the removing step can involve contacting the third mixture with a wash solution that includes the first, second and third types of nucleotides. Alternatively, the method can further include a step for removing free polymerases from the fourth mixture between steps (e) and (f). More preferably, the removing step can involve contacting the fourth mixture with a wash solution that includes the first, second, third and fourth types of nucleotides. According to a different embodiment, when the method includes steps (f) and (g), the third reagent further includes the third type of nucleotide. According to yet a different embodiment, when the method includes steps (f) and (g), the first type of nucleotide is not covalently attached to the primed template nucleic acid in the first stabilized ternary complex of the fourth mixture; the second type of nucleotide is not covalently attached to the primed template nucleic acid in the second stabilized ternary complex of the fourth mixture, the third type of nucleotide is not covalently attached to the primed template nucleic acid in the third stabilized ternary complex of the fourth mixture, and the fourth type of nucleotide is not covalently attached to the primed template nucleic acid in the fourth stabilized ternary complex of the fourth mixture.

In another aspect, the disclosure relates to a method of identifying the next correct nucleotide for a primed template nucleic acid molecule. The method includes the step of (a) serially contacting the primed template nucleic acid molecule with a plurality of distinguishable polymerase-nucleotide combinations under discriminating conditions and without incorporation, where each of the combinations includes a different distinguishably labeled polymerase and a different nucleotide, and whereby there is formed a complex including one of the different distinguishably labeled polymerases and one of the different nucleotides, each delivered in combination with the other, and the primed template nucleic acid molecule when the one of the different nucleotides is the next correct nucleotide for the primed template nucleic acid molecule. There also is the step of (b) detecting the complex by detecting the one of the different distinguishably labeled polymerases. There also is the step of (c) identifying the next correct nucleotide for the primed template nucleic acid molecule as the one of the different nucleotides that contacted the primed template nucleic acid molecule in combination with the one of the different distinguishably labeled polymerases to form the complex. According to one generally preferred embodiment, the primed template nucleic acid molecule is contained within a flow cell, and step (a) involves contacting the primed template nucleic acid molecule by flowing through the flow cell a liquid reagent that includes the plurality of distinguishable polymerase-nucleotide combinations. More preferably, the primed template nucleic acid molecule is disposed on a bead, and the bead is contained within the flow cell. According to a different preferred embodiment, the method further includes the step of removing substantially all of the different distinguishably labeled polymerase that did not complex with the primed template nucleic acid molecule in the prior contacting step, without removing substantially all of the one of the different distinguishably labeled polymerases of the complex. When this is the case, the removing step can involve flowing a wash buffer through the flow cell, where the wash buffer includes each of the different nucleotides of all prior contacting steps. Preferably, each of the different nucleotides of the combinations in step (a) is a different native nucleotide, where the complex that includes one of the different nucleotides includes one of the different native nucleotides, and where step (c) involves identifying the next correct nucleotide for the primed template nucleic acid molecule as the one of the different native nucleotides that contacted the primed template nucleic acid molecule in combination with the one of the different distinguishably labeled polymerases to form the complex. Alternatively, each of the different nucleotides of the combinations in step (a) is a different unlabeled nucleotide, where the complex that includes one of the different nucleotides includes one of the different unlabeled nucleotides, and where step (c) involves identifying the next correct nucleotide for the primed template nucleic acid molecule as the one of the different unlabeled nucleotides that contacted the primed template nucleic acid molecule in combination with the one of the different distinguishably labeled polymerases to form the complex. More preferably, the each of the different unlabeled nucleotides can be a different unlabeled native nucleotide. Alternatively, the plurality of distinguishable polymerase-nucleotide combinations consists of four distinguishable polymerase-nucleotide combinations, and no more than a single of the four distinguishable polymerase-nucleotide combinations contacts the primed template nucleic acid molecule at any time. More preferably, the primed template nucleic acid molecule contacts no more than a single of the plurality of distinguishable polymerase-nucleotide combinations at any time, and each of the plurality of distinguishable polymerase-nucleotide combinations includes a different nucleotide analog. Alternatively, the method further includes, after step (c), the step of (d) removing the one of the different distinguishably labeled polymerases and the one of the different nucleotides from the primed template nucleic acid molecule of the complex by washing the complex with a stripping buffer. Preferably, the stripping buffer includes a chemical agent that removes any reversible terminator moiety that may be present on the 3' nucleotide of the primer strand of the primed template nucleic acid molecule. More preferably, the method further includes, after step (d), the step of (e) incorporating a nucleotide into a primer strand of the primed template nucleic acid molecule using a polymerase different from any of the different distinguishably labeled polymerases of step (a). Still more preferably, the nucleotide that is incorporated into the primer includes a reversible terminator moiety that precludes subsequent phosphodiester bond formation. Still more preferably, the nucleotide that is incorporated into the primer is a native nucleotide. Alternatively, when the method further includes step (d), the primed template nucleic acid molecule can include a primer with a reversible terminator moiety that precludes incorporation of the next correct nucleotide by phosphodiester bond formation. Alternatively, when the method further includes steps (d) and (e), the method can further include, after step (d) and before step (e), the step of removing any reversible terminator moiety that may be present on the primer strand. Alternatively, each polymerase of the different distinguishably labeled polymerases of the plurality of distinguishable polymerase-nucleotide combinations can be labeled with a different label that produces a distinguishable optical signal. For example, the distinguishable optical signal can be a distinguishable fluorescent signal. Yet more preferably, the distinguishable fluorescent signals produced by the different labels of the different distinguishably labeled polymerases are substantially unchanged in the presence or absence of the next correct nucleotide. According to another generally preferred embodiment, each of the different nucleotides of the combinations in step (a) can be a different native nucleotide, the complex that includes one of the different nucleotides can include one of the different native nucleotides, and step (c) includes identifying the next correct nucleotide for the primed template nucleic acid molecule as the one of the different native nucleotides that contacted the primed template nucleic acid molecule in combination with the one of the different distinguishably labeled polymerases to form the complex. According to another generally preferred embodiment, each of the different nucleotides of the combinations in step (a) can be a different unlabeled nucleotide, the complex that includes one of the different nucleotides includes one of the different unlabeled nucleotides, and step (c) involves identifying the next correct nucleotide for the primed template nucleic acid molecule as the one of the different unlabeled nucleotides that contacted the primed template nucleic acid molecule in combination with the one of the different distinguishably labeled polymerases to form the complex. Each of the different unlabeled nucleotides can be a different unlabeled native nucleotide. According to another generally preferred embodiment, the plurality of distinguishable polymerase-nucleotide combinations consists of four distinguishable polymerase-nucleotide combinations, and no more than a single of the four distinguishable polymerase-nucleotide combinations contacts the primed template nucleic acid molecule at any time. According to another generally preferred embodiment, the primed template nucleic acid molecule includes a primer with a reversible terminator moiety that precludes incorporation of the next correct nucleotide by phosphodiester bond formation. According to another generally preferred embodiment, the method further includes after step (c), the step of (d) removing the one of the different distinguishably labeled polymerases and the one of the different nucleotides from the primed template nucleic acid molecule of the stable complex by washing the complex with a stripping buffer. More preferably, the method further includes after step (d), the step of (e) incorporating a nucleotide into a primer strand of the primed template nucleic acid molecule using a polymerase different from any of the different distinguishably labeled polymerases of step (a). Still more preferably, the nucleotide that is incorporated into the primer includes a reversible terminator moiety that precludes phosphodiester bond formation. According to another generally preferred embodiment, the primed template nucleic acid molecule contacts no more than a single of the plurality of distinguishable polymerase-nucleotide combinations at any time, and each of the plurality of distinguishable polymerase-nucleotide combinations includes a different nucleotide analog. According to another generally preferred embodiment, each polymerase of the different distinguishably labeled polymerases of the plurality of distinguishable polymerase-nucleotide combinations can be labeled with a different label that produces a distinguishable optical signal. For example, the distinguishable optical signal can be a distinguishable fluorescent signal. Still more preferably, the distinguishable fluorescent signals produced by the different labels of the different distinguishably labeled polymerases are substantially unchanged in the presence or absence of the next correct nucleotide. According to another generally preferred embodiment, the method further includes the step of removing substantially all of the different distinguishably labeled polymerase that did not complex with the primed template nucleic acid molecule in the prior contacting step, without removing substantially all of the one of the different distinguishably labeled polymerases of the complex.

In another aspect, the disclosure relates to a method of identifying next correct nucleotides for individuals among populations of nucleic acid features. The method includes the step of (a) providing a population of features that include primed template nucleic acid molecules. There also is the step of (b) first contacting the population of step (a) with a first reagent solution that includes a first distinguishably labeled polymerase, a first nucleotide, and a ternary complex-stabilizing agent, whereby there results a first population binding product. There also is the step of (c) second contacting the first population binding product with a second reagent solution including a second distinguishably labeled polymerase, a second nucleotide, and the ternary complex-stabilizing agent, whereby there results a second population binding product. There also is the step of (d) third contacting the second population binding product with a third reagent solution that includes a third distinguishably labeled polymerase, a third nucleotide, and the ternary complex-stabilizing agent, whereby there results a third population binding product. There also is the step of (e) fourth contacting the third population binding product with a fourth reagent solution including a fourth distinguishably labeled polymerase, a fourth nucleotide, and the ternary complex-stabilizing agent, whereby there results a fourth population binding product. There also is the step of (f) imaging the fourth population binding product to detect each of the distinguishably labeled polymerases, thereby determining which among the population of features include ternary complexes having one of the first, second, third, and fourth distinguishably labeled polymerases. There also is the step of (g) identifying the next correct nucleotide for individuals among the population of features having primed template nucleic acid molecules using imaging results from step (f). According to one generally preferred embodiment, the ternary complex-stabilizing agent is a non-catalytic metal ion. For example, the non-catalytic metal ion can be a trivalent lanthanide cation. Preferably, the trivalent lanthanide cation is $Eu^{3+}$ and not $Tb^{3+}$. Alternatively, the trivalent lanthanide cation is $Tb^{3+}$ and not $Eu^{3+}$. According to another generally preferred embodiment, the second reagent solution further includes the first nucleotide, the third reagent solution further includes the first nucleotide and the second nucleotide, and the fourth reagent solution further includes the first nucleotide, the second nucleotide, and the third nucleotide. More preferably, the population of features in step (a) includes a collection of beads having primed template nucleic acid molecules, and step (g) involves comparing, for each bead of the collection, intensities of optical signals produced by each of the distinguishably labeled polymerases imaged in step (f). Alternatively, the population of features in step (a) includes a collection of in situ synthesized template nucleic acid molecules, and step (g) involves comparing, for each in situ synthesized template nucleic acid molecule of the collection, intensities of optical signals produced by each of the distinguishably labeled polymerases imaged in step (f). In accordance with a different alternative, after each of steps (b)-(e) there is a step for washing the population binding product of the immediately prior step to remove the polymerase of the immediately prior contacting step, but maintaining the ternary complex stabilizing agent and each of the nucleotides of all prior steps. According to another generally preferred embodiment, each of the nucleotides is unlabeled, and each of the polymerases has a different optically detectable label that is distinguishable from the others. According to another generally preferred embodiment, the primed template nucleic acid molecules of the population provided in step (a) includes primers with 3'-OH moieties on the 3'-terminal nucleotides. According to another generally preferred embodiment, primers of the primed template nucleic acid molecules of the population provided in step (a) do not include reversible terminator moieties. According to another generally preferred embodiment, the method further includes the steps of: (g) removing from the fourth population binding product each of the polymerases that may be present; and (h) incorporating reversible terminator nucleotides into the primed template nucleic acid molecules that remain after step (g).

In another aspect, the disclosure relates to a composition. The composition includes: (a) an array of different primed template nucleic acids attached to a solid support; (b) a plurality of first stabilized ternary complexes, each of the first stabilized ternary complexes including a first primed template nucleic acid of the array, a polymerase, and a first type of nucleotide that is non-covalently bound as the next correct nucleotide of the first primed template nucleic acid; and (c) a plurality of second stabilized ternary complexes, where each of the second stabilized ternary complexes includes a second primed template nucleic acid of the array that is different from the first primed template nucleic acid, a polymerase, and a second type of nucleotide that is non-covalently bound as the next correct nucleotide of the second primed template nucleic acid and that is different from the first type of nucleotide, and where the first and second types of nucleotides are not distinguishably labeled with respect to each other. According to one generally preferred embodiment, the polymerase of the first stabilized complex can be covalently attached to a first label. When this is the case, the polymerase of the second stabilized complex can be covalently attached to a second label that is different from the first label. According to another generally preferred embodiment, the first and second stabilized ternary complexes can be in fluid communication with each other on the solid support. For example, the fluid includes free nucleotides of the first and second types. Alternatively, the fluid includes free polymerase. According to another generally preferred embodiment, the composition further includes a plurality of third stabilized ternary complexes, where each of the third stabilized ternary complexes includes a third primed template nucleic acid of the array that is different from the first and second primed template nucleic acids, a polymerase, and a third type of nucleotide that is non-covalently bound as the next correct nucleotide of the third primed template nucleic acid and that is different from the first and second types of nucleotides, and where the first, second and third types of nucleotides are not distinguishably labeled with respect to each other. Preferably, the polymerase of the third stabilized complex is covalently attached to a third label that is different from the first and second labels. Alternatively, the first, second and third stabilized ternary complexes are in fluid communication with each other on the sold support. Preferably, the fluid includes free nucleotides of the first, second and third types. Alternatively, when the composition further includes the plurality of third stabilized ternary complexes, where each of the third stabilized ternary complexes includes the third primed template nucleic acid of the array that is different from the first and second primed template nucleic acids, the polymerase, and the third type of nucleotide that is non-covalently bound as the next correct nucleotide of the third primed template nucleic acid and that is different from the first and second types of nucleotides, and where the first, second and third types of nucleotides are not distinguishably labeled with respect to each other, the composition can further include a plurality of fourth stabilized ternary complexes, where each of the fourth stabilized ternary complexes includes a fourth primed template nucleic acid of the array that is different from the first, second and third primed template nucleic acids, a polymerase, and a fourth type of nucleotide that is non-covalently bound as the next correct nucleotide of the fourth primed template nucleic acid and that is different from the first, second and third types of nucleotides, and where the first, second, third and fourth types of nucleotides are not distinguishably labeled with respect to each other. Preferably, the polymerase of the fourth stabilized complex is covalently attached to a fourth label that is different from the first, second and third labels. Alternatively, the first, second, third and fourth stabilized ternary complexes are in fluid communication with each other on the solid support. More preferably, the fluid includes free nucleotides of the first, second, third and fourth types.

In another aspect, the disclosure relates to a system that identifies a next correct nucleotide of a primed template nucleic acid molecule. The system includes: (a) a reaction vessel in fluid communication with a supply of four distinguishably labeled polymerases; (b) a reagent dispense module configured to direct into the reaction vessel, one at a time, a liquid reagent including one of the four distinguishably labeled polymerases in combination with one or more different nucleotides for each of four reagent exchanges; (c) an imaging module; (d) a processing module that receives a result from the imaging module and identifies the next correct nucleotide using the result; and (e) an electronic storage device, in communication with the processing module, that stores a non-transient record of the next correct nucleotide identified by the processing module. The imaging module can be configured to detect which of the four distinguishably labeled polymerases is present in a complex that includes: (i) the primed template nucleic acid molecule, (ii) one of the four distinguishably labeled polymerases, and (iii) the next correct nucleotide. According to one generally preferred embodiment, the electronic storage device includes a computer hard drive. According to another generally preferred embodiment, the system further includes: (f) an output device that produces a non-transient record of the next correct nucleotide identified by the processing module. According to another generally preferred embodiment, the reaction vessel is either a flow cell, or an individual well of a multiwell plate. When this is the case, the reaction vessel is the flow cell, and each reagent exchange involves flowing through the flow cell a second liquid reagent to replace a first liquid reagent. For example, the imaging module includes an illumination component and a detection component, each of the four distinguishably labeled polymerases having a fluorescent detectable label, each of the fluorescent detectable labels is excited by a wavelength of energy produced by the illumination component, and the detection component is configured to detect intensities of a plurality of different wavelengths, each corresponding to a fluorescence emission by one of the four distinguishably labeled polymerases. More preferably, none of the fluorescent detectable labels is an intercalating dye, and none of the fluorescent detectable labels is excited by energy transfer from a different molecular species. According to another generally preferred embodiment, the reagent dispense module includes a syringe pump that controllably transfers one of the four distinguishably labeled polymerases in combination with one of the different nucleotides. According to another generally preferred embodiment, the imaging module includes an illumination component and a detection component, each of the four distinguishably labeled polymerases includes a fluorescent detectable label, where each of the fluorescent detectable labels is excited by a wavelength of energy produced by the illumination component, and the detection component is configured to detect intensities of a plurality of different wavelengths, each corresponding to a fluorescence emission by one of the four distinguishably labeled polymerases. According to another generally preferred embodiment, the processing module includes a computer configured with software to compare intensities of the plurality of different wavelengths, and to determine therefrom the identity of the next correct nucleotide. According to another generally preferred embodiment, the non-transient record produced by the output device is either a record stored on computer-readable media, or a record printed on paper. According to another generally preferred embodiment, the liquid reagent directed into the reaction vessel by the reagent dispense module further includes a ternary complex-stabilizing agent. Alternatively, none of the fluorescent detectable labels is an intercalating dye, and none of the fluorescent detectable labels is excited by energy transfer from a different molecular species.

In another aspect, the disclosure relates to a method of identifying the next correct nucleotide for a primed template nucleic acid molecule. The method includes the step of (a) serially contacting the primed template nucleic acid molecule with a plurality of distinguishable polymerase-nucleotide combinations under discriminating conditions and without incorporation, where each of the combinations includes a polymerase and a different nucleotide, and whereby there is formed a complex that includes the polymerase and one of the different nucleotides, each delivered in combination with the other, and the primed template nucleic acid molecule when the one of the different nucleotides is the next correct nucleotide for the primed template nucleic acid molecule. There also is the step of (b) detecting the complex by detecting the polymerase. There also is the step of (c) identifying the next correct nucleotide for the primed template nucleic acid molecule as the one of the different nucleotides that contacted the primed template nucleic acid molecule in combination with the polymerase detected in step (b). According to one generally preferred embodiment, the polymerase of each of the combinations is distinguishably labeled compared to the others. Preferably, the polymerase of each of the combinations includes a different fluorescent label. Alternatively, the polymerase of each of the combinations is not distinguishably labeled compared to the others. More preferably, the polymerase of each of the combinations is labeled with the same detectable label, each of the combinations includes the different nucleotide at a different concentration, and step (b) involves detecting the polymerase by detecting intensity of a signal produced thereby. According to another generally preferred embodiment, none of the different nucleotides includes a detectable label. Preferably, each of the different nucleotides is a different native nucleotide. According to another generally preferred embodiment, each of the plurality of distinguishable polymerase-nucleotide combinations includes one or more nucleotides. In certain embodiments, wherein the polymerase of each of the combinations includes a different fluorescent label, each of the different fluorescent labels can produce a distinguishable optical signal that is substantially unchanged in the presence or absence of the next correct nucleotide, and none of the different fluorescent labels is in energy transfer relationship with any chemical moiety attached to the polymerase. According to another generally preferred embodiment, the method further includes the step of (d) incorporating a nucleotide into a primer strand of the primed template nucleic acid molecule using a polymerase different from any polymerase of step (a). According to another generally preferred embodiment, the method further includes the step of (d) removing the polymerase and the one of the different nucleotides from the primed template nucleic acid molecule of the complex by washing the complex with a stripping buffer. Preferably, the method further includes, after step (d), the step of: (e) incorporating a nucleotide into a primer strand of the primed template nucleic acid molecule using a polymerase different from any polymerase of step (a). Still more preferably, the nucleotide that is incorporated into the primer includes a reversible terminator moiety that precludes phosphodiester bond formation.

Definitions

Unless defined otherwise, all technical and scientific terms used herein have the same meaning as is commonly understood by one of ordinary skill in the art. For clarity, the following specific terms have the specified meanings. Other terms are defined in other sections herein.

The singular forms "a" "an" and "the" include plural referents unless the context clearly dictates otherwise. Approximating language, as used in the description and claims, may be applied to modify any quantitative representation that could permissibly vary without resulting in a change in the basic function to which it is related. Accordingly, a value modified by a term such as "about" is not to be limited to the precise value specified. Unless otherwise indicated, all numbers expressing quantities of ingredients, properties such as molecular weight, reaction conditions, so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the compositions, apparatus, or methods of the present disclosure. At the very least, each numerical parameter should at least be construed in light of the number of reported significant digits and by applying ordinary rounding techniques.

As used herein, "Sequencing By Binding™ technique" refers to a sequencing technique wherein specific binding of a polymerase to a primed template nucleic acid molecule is used for identifying the next correct nucleotide to be incorporated into the primer strand of the primed template nucleic acid. The specific binding interaction need not result in chemical incorporation of the nucleotide into the primer. In some embodiments, the specific binding interaction can precede chemical incorporation of the nucleotide into the primer strand or can precede chemical incorporation of an analogous, next correct nucleotide into the primer. Thus, identification of the next correct nucleotide can take place without incorporation of the next correct nucleotide.

As used herein, "stabilize" and its grammatical variants mean to hold steady or limit fluctuations. "Stabilizing" a complex refers to promoting or prolonging the existence of the complex or inhibiting disruption of the complex. The term can be applied to any of a variety of complexes including, but not limited to a binary complex or ternary complex. For example, the complex that is stabilized can be a ternary complex between a polymerase, primed template nucleic acid and cognate nucleotide. Generally, stabilization of the ternary complex prevents incorporation of the nucleotide component of the ternary complex into the primed nucleic acid component of the ternary complex. Accordingly, stabilizing a ternary complex can refer to promoting or prolonging non-covalent interactions that bind components of the ternary complex, or inhibiting disruption of non-covalent interactions that bind components of the ternary complex.

As used herein, "destabilize" and its grammatical variants mean to cause something to be unable to continue existing or working in its usual way. "Destabilizing" a complex refers to the process of promoting dissolution or breakdown of the complex (e.g., separation of the components of the complex). "Destabilizing" a complex also includes the process of inhibiting or preventing formation of the complex. The term can be applied to any of a variety of complexes including, but not limited to a binary complex or ternary complex. A ternary complex can be destabilized in a way that does not necessarily result in formation of a covalent bond between a primed template nucleic acid and next correct nucleotide.

As used herein, a "salt providing monovalent cation" is an ionic compound that dissociates in aqueous solution to produce cations having a single positive charge. For example, the cations can be metal cations where the oxidation state +1.

As used herein, "a glutamate salt" is an ionic compound that dissociates in aqueous solution to produce glutamate anions.

As used herein, to provide reaction conditions that "enhance" ternary complex formation over binary complex formation means to provide conditions that give a ratio of ternary complex to binary complex signals that is greater than one to one. An enhancement of two-fold means that signal associated with ternary complex formation is twice the signal associated with binary complex formation.

As used herein, "nucleic acid" or "oligonucleotide" or "polynucleotide" means at least two nucleotides covalently linked together. Thus, the terms include, but are not limited to, DNA, RNA, analogs (e.g., derivatives) thereof or any combination thereof, that can be acted upon by a polymerizing enzyme during nucleic acid synthesis. The term includes single-, double-, or multiple-stranded DNA, RNA and analogs (e.g., derivatives) thereof. Double-stranded nucleic acids advantageously can minimize secondary structures that may hinder nucleic acid synthesis. A double stranded nucleic acid may possess a nick or a single-stranded gap. A nucleic acid may represent a single, plural, or clonally amplified population of nucleic acid molecules.

As used herein, a "template nucleic acid" is a nucleic acid to be detected, sequenced, evaluated or otherwise analyzed using a method or apparatus disclosed herein.

As used herein, "primed template nucleic acid" is a template nucleic acid primed with (i.e., hybridized to) a primer, wherein the primer is an oligonucleotide having a 3'-end with a sequence complementary to a portion of the template nucleic acid. The primer can optionally have a free 5' end (e.g., the primer being noncovalently associated with the template) or the primer can be continuous with the template (e.g., via a hairpin structure). The primed template nucleic acid includes the complementary primer and the template nucleic acid to which it is bound.

As used herein, the "next template nucleotide" (or the "next template base") refers to the nucleotide in a template nucleic acid that is located immediately 5' of the base in the template that is hybridized to the 3'-end of a hybridized primer.

As used herein, the "next correct nucleotide" (sometimes referred to as the "cognate" nucleotide) is the nucleotide having a base complementary to the base of the next template nucleotide. The next correct nucleotide will hybridize at the 3'-end of a primer to complement the next template nucleotide. The next correct nucleotide can be, but need not necessarily be, capable of being incorporated at the 3' end of the primer. For example, the next correct nucleotide can be a member of a ternary complex that will complete an incorporation reaction or, alternatively, the next correct nucleotide can be a member of a stabilized ternary complex that does not catalyze an incorporation reaction. A nucleotide having a base that is not complementary to the next template base is referred to as an "incorrect" (or "non-cognate") nucleotide.

As used herein, a "blocked primed template nucleic acid" is a primed template nucleic acid modified to preclude or prevent phosphodiester bond formation at the 3'-end of the primer. Blocking may be accomplished, for example, by chemical modification with a blocking group at either the 3' or 2' position of the five-carbon sugar at the 3' terminus of the primer. Alternatively, or in addition, chemical modifications that preclude or prevent phosphodiester bond formation may also be made to the nitrogenous base of a nucleotide. Reversible terminator nucleotide analogs including each of these types of blocking groups will be familiar to those having an ordinary level of skill in the art. Incorporation of these analogs at the 3' terminus of a primer results in a blocked primed template nucleic acid.

As used herein, "polymerase" is a generic term for a protein or other molecule that forms a ternary complex with a cognate nucleotide and primed template nucleic acid including but not limited to, DNA polymerase, RNA polymerase, reverse transcriptase, primase and transferase. Typically, the polymerase includes one or more active sites at which nucleotide binding may occur. Optionally a polymerase includes one or more active sites at which catalysis of nucleotide polymerization may occur. Optionally a polymerase lacks catalytic nucleotide polymerization function, for example, due to a modification such as a mutation or chemical modification. Alternatively, the polymerase may catalyze the polymerization of nucleotides to the 3'-end of a primer bound to its complementary nucleic acid strand. For example, a polymerase catalyzes the addition of a next correct nucleotide to the 3'-OH group of the primer via a phosphodiester bond, thereby chemically incorporating the nucleotide into the primer. Optionally, the polymerase used in the provided methods is a processive polymerase. Optionally, the polymerase used in the provided methods is a distributive polymerase.

As used herein, "distinguishably labeled polymerases" are polymerases harboring different detectable labels, where the two labels can be told apart from each other to permit independent detection of the different polymerases. Preferred distinguishable labels include different fluorescent labels having different excitation and/or emission spectra, or Raman labels producing different Raman signatures.

As used herein, a "polymerase-nucleotide combination" refers to a polymerase composition (e.g., one or more polymerases) and a single nucleotide or nucleotide analog that are used together (e.g., being mixed together and delivered as a mixture or combination), where both components are required for the combination.

As used herein, "extension" refers to the process after an oligonucleotide primer and a template nucleic acid have annealed to one another, wherein a polymerase enzyme catalyzes addition of one or more nucleotides at the 3'-end of the primer. A nucleotide that is added to a nucleic acid by extension is said to be "incorporated" into the nucleic acid. Accordingly, the term "incorporating" can be used to refer to the process of joining a nucleotide to the 3' end of a primer by formation of a phosphodiester bond.

As used herein, a "nucleotide" is a molecule that includes a nitrogenous base, a five-carbon sugar (e.g., ribose or deoxyribose), and at least one phosphate group or functional analogs of such a molecule. The functional analogs may have a function of forming a ternary complex with a polymerase and primed template nucleic acid and/or a function of being incorporated into a primed template nucleic acid. The term embraces ribonucleotides, deoxyribonucleotides, nucleotides modified to include exogenous labels or reversible terminators, and nucleotide analogs.

As used herein, a "test nucleotide" is a nucleotide being investigated for its ability to participate in formation of a ternary complex that further includes a primed template nucleic acid and a polymerase.

As used herein, a "native" nucleotide refers to a naturally occurring nucleotide that does not include an exogenous label (e.g., a fluorescent dye, or other label) or chemical modification such as may characterize a nucleotide analog. Examples of native nucleotides useful for carrying out the Sequencing By Binding™ procedures described herein include: dATP (2'-deoxyadenosine-5'-triphosphate); dGTP (2'-deoxyguanosine-5'-triphosphate); dCTP (2'-deoxycytidine-5'-triphosphate); dTTP (2'-deoxythymidine-5'-triphosphate); and dUTP (2'-deoxyuridine-5'-triphosphate).

As used herein, a "nucleotide analog" has modifications, such as chemical moieties, which replace, remove and/or modify any of the components (e.g., nitrogenous base, five-carbon sugar, or phosphate group(s)) of a native nucleotide. Nucleotide analogs may be either incorporable or non-incorporable by a polymerase in a nucleic acid polymerization reaction. Optionally, the 3'-OH group of a nucleotide analog is modified with a moiety. The moiety may be a 3' reversible or irreversible terminator of polymerase extension. The base of a nucleotide may be any of adenine, cytosine, guanine, thymine, or uracil, or analogs thereof. Optionally, a nucleotide has an inosine, xanthine, hypoxanthine, isocytosine, isoguanine, nitropyrrole (including 3-nitropyrrole) or nitroindole (including 5-nitroindole) base. Nucleotides may include, but are not limited to, ATP, UTP, CTP, GTP, ADP, UDP, CDP, GDP, AMP, UMP, CMP, GMP, dATP, dTTP, dUTP, dCTP, dGTP, dADP, dTDP, dCDP, dGDP, dAMP, dTMP, dCMP, and dGMP. Nucleotides may also contain terminating inhibitors of DNA polymerase, dideoxynucleotides or 2',3' dideoxynucleotides, which are abbreviated as ddNTPs (ddGTP, ddATP, ddTTP, ddUTP and ddCTP).

As used herein, a "blocking moiety," when used with reference to a nucleotide analog, is a part of the nucleotide that inhibits or prevents the nucleotide from forming a covalent linkage to a second nucleotide (e.g., via the 3'-OH of the nucleotide after it has been incorporated into a primer) during the incorporation step of a nucleic acid polymerization reaction. The blocking moiety of a "reversible terminator" nucleotide can be removed from the nucleotide analog to allow for nucleotide incorporation. Such a blocking moiety is referred to herein as a "reversible terminator moiety." A blocking moiety or reversible terminator moiety that is attached to a nucleotide generally prevents or inhibits reaction of the 3' oxygen of the nucleotide. Exemplary reversible terminator moieties are set forth in U.S. Pat. Nos. 7,427,673; 7,414,116; and 7,057,026 and PCT publications WO 91/06678 and WO 07/123744, each of which is incorporated by reference.

As used herein, "monitoring" (or sometimes "measuring"), when used in reference to a molecular binding event, refers to a process of detecting a measurable interaction or binding between two molecular species. For example, monitoring may involve detecting measurable interactions between a polymerase and primed template nucleic acid, typically at various points throughout a procedure. Monitoring can be intermittent (e.g., periodic) or continuous (e.g., without interruption), and can involve acquisition of quantitative results. Monitoring can be carried out by detecting multiple signals over a period of time during a binding event or, alternatively, by detecting signal(s) at a single time point during or after a binding event.

As used herein, "contacting," when used in reference to chemical reagents, refers to the mixing together of reagents (e.g., mixing an immobilized template nucleic acid and either a buffered solution that includes a polymerase, or the combination of a polymerase and a test nucleotide) so that a physical binding reaction or a chemical reaction may take place.

As used herein, "incorporating" or "chemically incorporating," when used in reference to a nucleic acid and nucleotide, refers to the process of joining a cognate nucleotide to a nucleic acid primer by formation of a phosphodiester bond.

As used herein, a "binary complex" is a complex between a polymerase and a primed template nucleic acid, where the complex does not include a nucleotide molecule such as the next correct nucleotide.

As used herein, a "ternary complex" is a complex between a polymerase, a primed template nucleic acid, and the next correct nucleotide positioned immediately downstream of the primer and complementary to the template strand of the primed template nucleic acid or the blocked primed template nucleic acid. The primed template nucleic acid can include, for example, a primer with a free 3'-OH or a blocked primer (e.g., a primer with a chemical modification on the base or the sugar moiety of the 3' terminal nucleotide, where the modification precludes enzymatic phosphodiester bond formation).

As used herein, a "catalytic metal ion" refers to a metal ion that facilitates phosphodiester bond formation between the 3'-OH of a nucleic acid (e.g., a primer) and the phosphate of an incoming nucleotide by a polymerase. A "divalent catalytic metal cation" is a catalytic metal ion having a valence of two. Catalytic metal ions can be present at concentrations necessary to stabilize formation of a complex between a polymerase, a nucleotide, and a primed template nucleic acid, referred to as non-catalytic concentrations of a metal ion. Catalytic concentrations of a metal ion refer to the amount of a metal ion sufficient for polymerases to catalyze the reaction between the 3'-OH group of a nucleic acid (e.g., a primer) and the phosphate group of an incoming nucleotide.

As used herein, a "non-catalytic metal ion" refers to a metal ion that, when in the presence of a polymerase enzyme, does not facilitate phosphodiester bond formation needed for chemical incorporation of a nucleotide into a primer. Typically, the non-catalytic metal ion is a cation. A non-catalytic metal ion may inhibit phosphodiester bond formation by a polymerase, and so may stabilize a ternary complex by preventing nucleotide incorporation. Non-catalytic metal ions may interact with polymerases, for example, via competitive binding compared to catalytic metal ions. A "divalent non-catalytic metal ion" is a non-catalytic metal ion having a valence of two. Examples of divalent non-catalytic metal ions include, but are not limited to, $Ca^{2+}$, $Zn^{2+}$, $Co^{2+}$, $Ni^{2+}$, and $Sr^{2+}$. The trivalent $Eu^{3+}$ and $Tb^{3+}$ ions are non-catalytic metal ions having a valence of three.

As used herein an "exogenous label" refers to a detectable chemical moiety of a sequencing reagent that is not present in a natural analog of the sequencing reagent, such as a non-naturally occurring label present on a synthetic nucleotide analog or a synthetic polymerase analog (e.g., a DNA polymerase). While a native dNTP may have a characteristic limited fluorescence profile, the native dNTP does not include any added colorimetric or fluorescent moiety. Conversely, a dATP (2'-deoxyadenosine-5'-triphosphate) molecule modified to include a chemical linker and fluorescent moiety attached to the gamma phosphate would be said to include an exogenous label because the attached chemical components are not ordinarily a part of the nucleotide. Of course, chemical modifications to add detectable labels to nucleotide bases also would be considered exogenous labels. Likewise, a DNA polymerase modified to include a fluorescent dye (e.g., by attachment to a cys residue that is part of the primary sequence of the enzyme) also would be said to include an exogenous label because the label is not ordinarily a part of the polymerase.

As used herein, "unlabeled" refers to a molecular species free of added or exogenous label(s) or tag(s). Of course, unlabeled nucleotides will not include either of an exogenous fluorescent label, or an exogenous Raman scattering tag. A native nucleotide is another example of an unlabeled molecular species. An unlabeled molecular species can exclude one or more of the labels set forth herein or otherwise known in the art relevant to nucleic acid sequencing or analytical biochemistry.

As used herein, a "flow cell" is a reaction chamber that includes one or more channels that direct fluid in a predetermined manner to conduct a desired reaction. The flow cell can be coupled to a detector such that a reaction occurring in the reaction chamber can be observed. For example, a flow cell can contain primed template nucleic acid molecules, for example, tethered to a solid support, to which nucleotides and ancillary reagents are iteratively applied and washed away. The flow cell can include a transparent material that permits the sample to be imaged after a desired reaction occurs. For example, a flow cell can include a glass slide containing small fluidic channels, through which polymerases, dNTPs and buffers can be pumped. The glass inside the channels can be decorated with one or more primed template nucleic acid molecules to be sequenced. An external imaging system can be positioned to detect the molecules on the surface of the glass. Reagent exchange in a flow cell is accomplished by pumping, drawing, or otherwise "flowing" different liquid reagents through the flow cell. Exemplary flow cells, methods for their manufacture and methods for their use are described in US Pat. App. Publ. Nos. 2010/0111768 A1 or 2012-0270305 A1; or WO 05/065814, each of which is incorporated by reference herein.

As used herein, a "reaction vessel" is a container that isolates one reaction (e.g., a binding reaction; an incorporation reaction; etc.) from another, or that provides a space in which a reaction can take place. Non-limiting examples of reaction vessels useful in connection with the disclosed technique include: flow cells, wells of a multiwell plate; microscope slides; tubes (e.g., capillary tubes); etc. Features to be monitored during binding and/or incorporation reactions can be contained within the reaction vessel.

As used herein, "library" refers to a collection of analytes having different chemical compositions. Typically, the analytes in a library will be different species having a common feature or characteristic. For example, a library can include nucleic acid species that differ in nucleotide sequence, but that are similar with respect to having a sugar-phosphate backbone.

As used herein, a "feature" is a point, area or volume of a material (e.g., a patterned or random array) that can be distinguished from other points or areas according to relative location. An individual feature can include one or more molecules of a particular type. For example, a feature can include a single target nucleic acid molecule having a particular sequence, or a feature can include an ensemble of several nucleic acid molecules having the same sequence and/or complementary sequence thereof. Different molecules that are at different features of a pattern can be distinguished from each other according to the locations of the features in the pattern. Exemplary features include without limitation, wells in a substrate, beads (or other particles) in or on a substrate, projections (e.g., in situ generated nucleic acid amplification products) from a substrate, pads of gel material on a substrate, or channels in a substrate.

As used herein, "population" refers to a collection of things that are somehow related (e.g., nucleic acids of the same or different sequences), and that are processed together. A "population of features" refers to a collection of features that are processed together (e.g., in a flow cell or in a well of a multiwell plate). Individuals among the collection may be single nucleic acid molecules (e.g., RCA amplification products), or a collection of homogenous nucleic acid molecules. Individual features can be distinguished from each other within or among the population. To "determine the identity of a next correct nucleotide for a population of features comprising primed template nucleic acid molecules" means to establish identity of the next correct nucleotide for the primed template nucleic acid molecules of the different features that make up the population. As examples, populations of target nucleic acids may be represented by a collection of beads or in situ generated nucleic acid amplification products.

As used herein, a "population binding product" refers to the product that results from a binding reaction (e.g., that may or may not result in formation of complexes) that involves a population of features. Thus, the term can refer to the product (e.g., the aggregated collection of features) that results from contacting a population of features comprising primed template nucleic acid molecules with a polymerase and a test nucleotide, where some features among the population may form ternary complexes, while others may not.

As used herein, taking place "serially" or "in serial fashion" means taking place sequentially, one after the other. In some embodiments, two steps can occur in a series allowing for intervening steps or actions (i.e., not necessarily without interruption). Polymerase-nucleotide combinations that serially contact a nucleic acid do not mingle with each other or accumulate (as would be the case for serial addition). Thus, contacting a nucleic acid molecule with two different polymerase-nucleotide combinations "serially" or "in serial fashion" means contacting with the first combination, and then contacting with the second combination sometime later when the first combination is no longer present. Mingling only one component of the first combination with the second combination does not constitute mingling of the two combinations. In an exemplary serial process, a nucleic acid population can be contacted with a first solution that contains a first polymerase-nucleotide combination and then, after the first solution has been removed, the nucleic acid population can be contacted with a second solution that contains a second polymerase-nucleotide combination. In this example, the solutions do not mingle but polymerase-nucleotide combinations from the two solutions can remain bound to the nucleic acid population at the same time.

As used herein, "discriminating conditions," when used in reference to a polymerase, are reaction conditions that distinguish between formation of a binary complex (a complex between the polymerase and a primed template nucleic acid molecule in the absence of a cognate nucleotide) and formation of a ternary complex (a complex between the polymerase and a primed template nucleic acid molecule in the presence of a cognate nucleotide). Discriminating conditions may be provided by a number of routes, including: use of salts (e.g., salts providing monovalent cations, or glutamate anions), use of polymerase enzymes engineered to exhibit low background binding in the presence of a non-cognate nucleotide, temperature adjustment, and/or pH adjustment etc.

As used herein, a "complex" is a molecular entity formed by non-covalent association involving two or more component molecular entities (e.g., a polymerase and a primed template nucleic acid molecule).

As used herein, "imaging" refers to a process for obtaining a representation of a sample or a portion thereof. The process may involve acquisition of optical data, such as the relative location of a feature undergoing analysis, and intensity of an optical signal produced at the position of the feature.

The terms "cycle" or "round," when used in reference to a sequencing procedure, refer to the portion of a sequencing run that is repeated to indicate the presence of a nucleotide. Typically, a cycle or round includes several steps such as steps for delivery of reagents, washing away unreacted reagents and detection of signals indicative of changes occurring in response to added reagents.

As used herein, a "non-transient" record is a record of results or information, where the record persists in time. A non-transient record can be stored and then referenced or retrieved at a later time. Non-limiting examples of non-transient recordings include printed information (e.g., paper records), electronically recorded information disposed on a computer-readable medium or storage device (e.g., a flash drive, disk drive, floppy disk, etc.), or otherwise recorded on a machine-readable form, such as a bar code for storing numerical values.

As used herein, to perform a "reagent exchange" means to substitute or replace one reagent (e.g., a liquid reagent) with something else. For example, a reagent exchange may involve flowing one liquid reagent through a flow cell to replace a different reagent that already is or was present in the flow cell. An optional wash step can occur between the exchange of reagents, but need not occur in all embodiments. Alternatively, a probe (e.g., an optical interferometry probe) derivatized with a primed template nucleic acid undergoing testing can be transferred from a reservoir containing one reagent to a different reservoir containing a different reagent. In yet another example, reagent exchange can be carried out using robotic liquid handling to remove one liquid reagent contained in a well of a multiwell plate, and to replace it with a volume of a different liquid reagent. In all cases, the composition of a reaction mixture will be different before and after the reagent exchange such that the first mixture, existing in a vessel prior to reagent exchange, will be understood to be different from the second mixture that results in the vessel after the reagent exchange.

As used herein, a "ternary complex-stabilizing agent" is any agent that promotes or maintains stability of a ternary complex that includes a primed template nucleic acid molecule, a polymerase, and a cognate nucleotide (i.e., the next correct nucleotide for the primed template nucleic acid molecule). Examples include: a non-catalytic metal ion that inhibits polymerization (e.g., $Ca^{2+}$, $Zn^{2+}$, $Co^{2+}$, $Ni^{2+}$, and $Sr^{2+}$), including trivalent lanthanide cations (e.g., $Eu^{3+}$ and $Tb^{3+}$); polymerases engineered to have reduced capacity for binary complex formation while exhibiting ternary complex formation capacity; polymerases engineered for complete loss of ability to catalyze phosphodiester bond formation in the presence of $Mg^{2+}$ ion.

As used herein, a "module" is a component (e.g., a separable component) of a system or apparatus that is interchangeable with others of like kind, as may be used in the construction of an apparatus or in replacement of a non-working part. For example, a "reagent dispense module" refers to a collection of interconnected components that may include one or more of any pumps, actuators, hosing and fluidics necessary for dispensing one or more reagents. Similarly, an "imaging module" refers to a collection of interconnected components that may include one or more of radiation sources, detectors, lensing, and other elements useful for imaging a collection of targets in a reaction vessel (e.g., a flow cell). A "processing module" refers to any collection of interconnected components (e.g., a computer and ancillary peripherals connected thereto) working together to perform computational analysis of a set of data.

DETAILED DESCRIPTION

Introduction

The present disclosure provides compositions, apparatus and methods that exploit the specificity of binding in a ternary complex formed between a polymerase, primed template nucleic acid and cognate nucleotide. The specificity can be exploited to determine the next correct nucleotide for the primed template nucleic acid by identifying the nucleotide that is present in the ternary complex. Surprisingly, the ternary complex that forms between a polymerase, primed template nucleic acid and next correct nucleotide can be stabilized, not only to prevent covalent incorporation of the nucleotide into the primer, but also to prevent the ternary complex from disassociating in the presence of competitive binding components such as other polymerases, primed template nucleic acids and next correct nucleotides.

As set forth in further detail below, the stability of the ternary complex to competitive binding events advantageously provides for multiplex analytical formats where multiple different ternary complexes are evaluated in parallel. The stability of the multiple different complexes allows them to be in fluid communication with each other in a vessel, such as a microarray or flow cell, while being analyzed in a detection method such as a sequencing method.

In particular embodiments, the stability of the ternary complex to competitive binding events advantageously allows sequential formation of ternary complexes having known or desired characteristics. Specifically, a first ternary complex can be maintained in the presence of reagents used to form a second ternary complex. For example, an array of primed template nucleic acids can include a first ternary complex that has been formed between a first polymerase, a first primed template nucleic acid and a first type of nucleotide. The array can be contacted with a second polymerase and a second type of nucleotide under conditions that result in formation of a second ternary complex (i.e., between a second primed template nucleic acid on the array, the second polymerase and the second type of nucleotide), wherein the conditions result in maintaining the first ternary complex. The array can be detected to distinguish the different ternary complexes at the features for the different primed template nucleic acids. An advantage of the multiplex techniques is that the different types of nucleotides need not be distinguishably labeled in order to distinguish the two ternary complexes (or the different primed template nucleic acids to which they respectively bind). Rather, the polymerases that are introduced to the array can be differentially labeled to correlate with the type of nucleotide that is present when the polymerase is contacted with the array.

Provided are methods and systems adapted to identify the next correct nucleotide for a primed template nucleic acid. The methods can be carried out in a multiplex configuration to identify the next correct nucleotide for each member of a population of different nucleic acids. The methods set forth herein are particularly useful for identifying the next correct nucleotide for one or more nucleic acids being interrogated in a Sequencing By Binding™ procedure. Sequencing By Binding™ procedures are typically carried out as a series of cycles, with each cycle including one or more steps that result in identification of the next correct nucleotide for a particular nucleic acid template. As such, the sequence of the nucleic acid template is determined from the series of nucleotides identified from the series of cycles. Convenient platforms for the sequencing chemistry can involve flow cells or individual wells of a multiwell plate, where the different nucleic acids may be present as features such as in vitro- or in situ-synthesized clusters of primed template nucleic acids, or such as immobilized microbeads displaying primed template nucleic acid molecules. Cognate nucleotide identification can be made by identifying one or more distinguishable polymerases used in a Sequencing By Binding™ procedure using as few as a single imaging step to detect each of four different types of cognate nucleotide (i.e., dATP, dGTP, dCTP, and dTTP or dUTP).

General features of the Sequencing By Binding™ technique of the present disclosure, together with details concerning various aspects of methods employing single-scan imaging are detailed below. It will be understood that the apparatus and methods set forth herein need not be limited to nucleic acid sequencing. For example, this disclosure provides methods for interrogating a single nucleotide site in a primed template nucleic acid. Interrogation of a single nucleotide site can be useful for detecting a variant at a single site (e.g., a single nucleotide polymorphism or SNP), for example, in a genotyping method. Typically, a genotyping method is carried out using a template nucleic acid with a known genetic locus, but for which an allelic variation at the locus is to be determined. Alternatively, identification of a single nucleotide site can be useful for evaluating characteristics of a target polymerase, such as specificity of the polymerase for binding to a correct nucleotide. This embodiment can be carried out using a primed template nucleic acid having known sequence including the identity of the nucleotide type that is considered the next correct nucleotide.

However, the primed template nucleic acid is contacted with a target polymerase and the method is used to determine whether or not, or the extent to which, the polymerase forms a ternary complex with the expected next correct nucleotide. Methods that interrogate only a single nucleotide site can be carried out using a single cycle of a Sequencing By Binding™ method set forth herein.

Moreover, the compositions, apparatus and methods of the present disclosure are exemplified below with regard to the use of labeled polymerase(s). For example, embodiments set forth herein can be carried out using unlabeled nucleotides and/or unlabeled nucleic acids. However, it will be understood that alternative embodiments can be configured similarly to those exemplified below, with the exception that another component is labeled or no label is used. For example, a component of a ternary complex such as a nucleotide, primer nucleic acid or template nucleic acid can be labeled. The other component can be labeled instead of having the label on the polymerase (i.e., a polymerase need not be labeled in some embodiments). Alternatively, both a polymerase and another component of a ternary complex can be labeled. Optionally, in some embodiments the nucleotides harbor detectable labels, and the polymerase does not include any label that is detected as an indicator of ternary complex formation. In these embodiments there would be no energy transfer from the polymerase to a labeled nucleotide.

Distinguishing Nucleic Acids

The present disclosure provides a method of distinguishing nucleic acids. The method can include steps of (a) providing a first mixture that includes a population of different primed template nucleic acids and a first stabilized ternary complex, the first stabilized ternary complex includes a first primed template nucleic acid of the mixture, a polymerase, and a first type of nucleotide, wherein the first stabilized ternary complex is attached to a first type of label; (b) forming a second stabilized ternary complex by contacting the first mixture with a first reagent including a second type of nucleotide and a polymerase, the second stabilized ternary complex including a second primed template nucleic acid of the first mixture, a polymerase of the reagent, and a second type of nucleotide of the reagent, wherein the second stabilized ternary complex is attached to a second type of label that is different from the first type of label, thereby forming a second mixture including the first and second stabilized ternary complexes; and (c) detecting the first and second type of label to distinguish the first primed template nucleic acid from the second primed template nucleic acid.

Optionally, the method of distinguishing nucleic acids can include a step of removing free (i.e., non-complexed) polymerases from the first mixture between steps (a) and (b). Alternatively or additionally, the method can include a step of removing free polymerases from the second mixture between steps (b) and (c).

In some embodiments, the population of different primed template nucleic acids is an array (e.g., a random or patterned distribution in spaced-apart relation) of the primed nucleic acids. For example, the primed template nucleic acids can be covalently attached to a surface to form features on the array. In such embodiments, or others that utilize components that are attached to a solid support, free (i.e., non-complexed) polymerase can be removed via a wash step. Optionally, the fluid used for the wash that removes free polymerase from the first mixture can include the first nucleotide. The presence of the first nucleotide in the wash can provide the advantage of stabilizing the first ternary complex. Similarly, the removing of the free polymerase from the second mixture can be carried out by a wash with a solution that contains the first and second types of nucleotides. The presence of the first and second nucleotides in the wash can provide the advantage of stabilizing the first and second ternary complexes.

The method of distinguishing nucleic acids can be used in a method for sequencing the nucleic acids. Accordingly, the method can further include steps of: (d) forming a third stabilized ternary complex by contacting the second mixture with a second reagent comprising a third type of nucleotide and a polymerase, the third stabilized ternary complex including a third primed template nucleic acid of the second mixture, a polymerase of the second reagent, and a third type of nucleotide of the second reagent, thereby forming a third mixture having the first, second and third stabilized ternary complexes, wherein the third stabilized ternary complex is attached to a third type of label that is different from the first and second types of labels; and (e) detecting the third type of label to distinguish the third primed template nucleic acid from the first and second primed template nucleic acids.

As a further option, the method can include steps of: (f) forming a fourth stabilized ternary complex by contacting the third mixture with a third reagent including a fourth type of nucleotide and a polymerase, the fourth stabilized ternary complex comprising a fourth primed template nucleic acid of the third mixture, a polymerase of the third reagent, and a fourth type of nucleotide of the third reagent, thereby forming a fourth mixture having the first, second, third and fourth stabilized ternary complexes, wherein the fourth stabilized ternary complex is attached to a fourth type of label that is different from the first, second and third types of labels; and (g) detecting the fourth type of label to distinguish the fourth primed template nucleic acid from the first, second and third primed template nucleic acids.

The first, second, third or fourth types of labels used in the method of distinguishing nucleic acids can optionally be attached to the polymerases in the respective stabilized ternary complexes. The first, second, third or fourth types of nucleotides need not be labeled (e.g., the nucleotides need not contain an exogenous label). Even if the nucleotides are labeled they need not be detected in the method of distinguishing nucleic acids.

As set forth above, the first reagent used in the method of distinguishing nucleic acids will include a second type of nucleotide and a polymerase, the second reagent will include a third type of nucleotide and a polymerase, and the third reagent will include a fourth type of nucleotide and a polymerase. As such the second, third and fourth types of nucleotides will participate in formation of the second, third and fourth stabilized ternary complexes. Each respective reagent can further include nucleotide types that were present in the prior-used reagent. More specifically, the first reagent can include the first and second types of nucleotide and the polymerase, the second reagent can include the first second and third types of nucleotide and the polymerase, and the third reagent can include the first, second, third and fourth types of nucleotides and the polymerase. The presence of the prior used nucleotide types in the reagents provides the advantage of stabilizing the prior formed ternary complexes from disassociating or reconstituting with other components.

The methods set forth herein can be used to produce a variety of nucleic acid compositions. The compositions can be stable products of a method set forth herein or they can be intermediates, some of which occur transiently.

Accordingly, the present disclosure provides a composition that includes (a) an array of different primed template nucleic acids attached to a solid support; (b) a plurality of first stabilized ternary complexes, wherein each of the first stabilized ternary complexes includes a first primed template nucleic acid of the array, a polymerase, and a first type of nucleotide that is non-covalently bound as the next correct nucleotide of the first primed template nucleic acid; and (c) a plurality of second stabilized ternary complexes, wherein each of the second stabilized ternary complexes includes a second primed template nucleic acid of the array that is different from the first primed template nucleic acid, a polymerase, and a second type of nucleotide that is non-covalently bound as the next correct nucleotide of the second primed template nucleic acid and that is different from the first type of nucleotide, and wherein the first and second types of nucleotides are not distinguishably labeled with respect to each other.

Optionally, the composition can further include (d) a plurality of third stabilized ternary complexes, wherein each of the third stabilized ternary complexes includes a third primed template nucleic acid of the array that is different from the first and second primed template nucleic acids, a polymerase, and a third type of nucleotide that is non-covalently bound as the next correct nucleotide of the third primed template nucleic acid and that is different from the first and second types of nucleotides, and wherein the first, second and third types of nucleotides are not distinguishably labeled with respect to each other. As a further option, the composition can include a plurality of fourth stabilized ternary complexes, wherein each of the fourth stabilized ternary complexes includes a fourth primed template nucleic acid of the array that is different from the first, second and third primed template nucleic acids, a polymerase, and a fourth type of nucleotide that is non-covalently bound as the next correct nucleotide of the fourth primed template nucleic acid and that is different from the first, second and third types of nucleotides, and wherein the first, second, third and fourth types of nucleotides are not distinguishably labeled with respect to each other.

As set forth elsewhere herein, the polymerases of one or more of the stabilized complexes can each be covalently attached to a label. The polymerases can be distinguishably labeled such that the label identity can be correlated with the type of nucleotide that is present in the respective stabilized ternary complex.

Optionally two or more of the stabilized ternary complexes can be in fluid communication with each other. For example, two or more of the first, second third and fourth stabilized ternary complexes can be in fluid communication with each other on the sold support. The fluid can optionally include free (i.e., non-complexed) nucleotides of the first, second, third and/or fourth types.

Other compositions that result from methods set forth herein are set forth below or will be immediately recognized by those skilled in the art as resulting from the methods based on the teachings herein.

Sequencing by Binding™ Technology: General Aspects

Described herein are polymerase-based nucleic acid Sequencing By Binding™ reactions, wherein the polymerase undergoes transitions between open and closed conformations during discrete steps of the reaction. In one step, the polymerase binds to a primed template nucleic acid to form a binary complex, also referred to herein as the pre-insertion conformation. In a subsequent step, an incoming nucleotide is bound and the polymerase fingers close, forming a pre-chemistry conformation comprising the polymerase, primed template nucleic acid and nucleotide; wherein the bound nucleotide has not been incorporated. This step may be followed by a $Mg^{2+}$- or Mn'-catalyzed chemical incorporation of the next correct nucleotide, wherein nucleophilic displacement of a pyrophosphate (PPi) by the 3'-hydroxyl of the primer results in phosphodiester bond formation. This is generally referred to as nucleotide "incorporation." The polymerase returns to an open state upon the release of PPi following nucleotide incorporation, and translocation initiates the next round of reaction. Certain details of the Sequencing By Binding™ procedure can be found in commonly owned U.S. patents and patent applications identified as U.S. Pat. No. 10,077,470, and 62/375,379, the entire disclosures of these documents being incorporated by reference herein for all purposes.

While a ternary complex including a primed template nucleic acid molecule having a primer with a free 3'-hydroxyl can form in the absence of a divalent catalytic metal ion (e.g., $Mg^{2+}$), chemical addition of nucleotide can proceed in the presence of the divalent metal ions. Low or deficient levels of catalytic metal ions, such as $Mg^{2+}$ tend to lead to non-covalent (physical) sequestration of the next correct nucleotide in a tight ternary complex. This ternary complex may be referred to as a stabilized or trapped ternary complex. Other methods disclosed herein also can be used to produce a stabilized ternary complex. In any reaction described above, the polymerase configuration and/or interaction with a nucleic acid may be monitored during an examination step to identify the next correct base in the nucleic acid sequence. Before or after incorporation, reaction conditions can be changed to disengage the polymerase from the primed template nucleic acid, and changed again to remove from the local environment any reagents that inhibit polymerase binding.

Generally speaking, the Sequencing By Binding™ procedure of the present disclosure includes an "examination" step that detects signals for identifying the next template base, and optionally a subsequent "incorporation" step that adds one or more complementary nucleotides to the 3'-end of the primer component of the primed template nucleic acid. Identity of the next correct nucleotide to be added is determined from signals detected either without, or before chemical linkage of that nucleotide to the 3'-end of the primer through a covalent bond. The examination step can involve providing a primed template nucleic acid to be used in the procedure, and contacting the primed template nucleic acid with a polymerase enzyme (e.g., a DNA polymerase) composition and one or more test nucleotides being investigated as the possible next correct nucleotide. Further, there is a step that involves monitoring or measuring the interaction between the polymerase and the primed template nucleic acid in the presence of the test nucleotides.

Optionally, monitoring of the interaction can take place when the primer of the primed template nucleic acid molecule includes a blocking group that precludes enzymatic incorporation of an incoming nucleotide into the primer. The interaction generally can take place in the presence of stabilizers, whereby the polymerase-nucleic acid interaction is stabilized in the presence of the next correct nucleotide (i.e., stabilizers that stabilize the ternary complex). Again, the examination step collects signal(s) that identify or determine the identity of the next correct nucleotide without requiring incorporation of that nucleotide. Stated differently, identity of the next correct nucleotide can be established without chemical incorporation of the nucleotide into the primer, whether or not the 3'-end of the primer is blocked.

Whereas methods involving a single template nucleic acid molecule may be described for convenience, these methods are exemplary. The sequencing methods provided herein readily encompass a plurality of template nucleic acids, wherein the plurality of nucleic acids may be clonally amplified copies of a single nucleic acid, or disparate nucleic acids, including combinations, such as populations of disparate nucleic acids that are clonally amplified.

The Examination Step

Generally, an examination step in a Sequencing By Binding™ procedure in accordance with the disclosed technique typically includes the following sub-steps: (1) providing a primed template nucleic acid molecule (i.e., a template nucleic acid molecule hybridized with a primer that optionally may be blocked from extension at its 3'-end); (2) contacting the primed template nucleic acid molecule with a reaction mixture that includes at least one polymerase that can be distinguished from others used in the procedure (e.g., by virtue of including a detectable label) and one nucleotide; (3) detecting the interaction of the polymerase with the primed template nucleic acid molecule in the presence of the nucleotide and without chemical incorporation of any nucleotide into the primed template nucleic acid; and (4) determining from the detected interaction the identity of the next base in the template nucleic acid (i.e., the next correct nucleotide).

In the above embodiment, and several embodiments exemplified below, the examination step includes a sub-step of determining or identifying a nucleotide type. It will be understood that a determination or identification sub-step of a cycle can occur on a timeframe that is separate from fluidic and detection sub-steps of that cycle. For example, the determination or identification sub-step can occur after a delay that covers one or more subsequent cycles in a Sequencing By Binding™ procedure. In some cases, the determination or identification of the next correct nucleotide for each cycle can occur after all of the cycles of a Sequencing By Binding™ procedure have been completed. Thus, signal data from the examination step of each cycle can be stored in a way that it is indexed to the respective cycle to allow later analysis on a cycle by cycle basis.

In one embodiment, an examination step includes: (1) serially contacting a primed template nucleic acid (where the primer strand optionally is blocked from extension at its 3'-end) with a plurality of distinguishably labeled polymerase-nucleotide combinations under conditions that discriminate between formation of ternary complexes and binary complexes; (2) detecting any ternary complexes that formed as a result of the serial contacting steps by detecting one or more of the distinguishably labeled polymerases from the combinations used in the different contacting steps; and (3) identifying the next correct nucleotide for the primed template nucleic acid as the nucleotide component of the distinguishably labeled polymerase-nucleotide combination that formed the ternary complex. Preferably, the detection step is performed after the serial contacting steps have all been completed. This can be achieved by stabilizing the ternary complex (e.g., by use of a ternary complex-stabilizing agent) sufficiently so that the first ternary complex to form survives through the processing needed to form the second ternary complex. While a ternary complex may be stabilized by non-catalytic cations that inhibit nucleotide incorporation or polymerization, primers blocked at their 3'-ends and or polymerases that are engineered to lack catalytic activity provide alternative stabilization approaches. For example, a trivalent lanthanide cation or other stabilizing agent may be used to inhibit dissociation of the complex (e.g., to "lock" the ternary complex in place). Notably, detection can be performed before all the serial contacting steps are finished, for example, separate detection events can be carried out after each of the respective contacting steps.

In a different embodiment that takes advantage of single-scan imaging to process a population of primed template nucleic acid molecules, an examination step includes: (1) providing the population; (2) serially performing a plurality of contacting steps (e.g., four contacting steps), one after the other, that involve contacting the population with different reagent solutions, where each reagent solution contains a distinguishable polymerase (e.g., being distinguishable from the others by virtue of a detectable label) and a different nucleotide in the presence of a ternary complex-stabilizing agent; (3) imaging the population after performance of at least two, and preferably after performance of all four contacting steps to detect labels associated with the different distinguishable polymerase compositions, thereby determining which members of the population participate in ternary complexes independently containing the different polymerases; and (4) determining identities of cognate nucleotides for different members of the population from the imaging results. More particularly, the determining step optionally may involve identifying cognate nucleotides by assessing which polymerase(s) participated in a ternary complex for a particular member of the population. When multiple imaging steps conveniently can be performed, imaging and detection can take place after each contacting step has concluded. Notably, the serial contacting steps are carried out in a serial fashion, so that the different polymerase and nucleotide combinations do not mix prior to formation of their respective ternary complexes. Thus, the polymerase and nucleotide (as a combination, unassociated with primed template nucleic acid) from one step should not mingle or mix with the polymerase and nucleotide (as a combination, unassociated with primed template nucleic acid) from a subsequent step. More particularly, free (i.e., non-complexed) polymerase from a prior contacting step should not mingle with (i.e., should not be simultaneously present with) a nucleotide type that is first introduced in a subsequent contacting step. Conversely, it is acceptable to mix a free (i.e., non-complexed) nucleotide type from a prior contacting step with a polymerase used in a subsequent contacting step.

The primer of the primed template nucleic acid optionally can be either an extendible primer, or a primer blocked from extension at its 3'-end (e.g., by the presence of a reversible terminator moiety). The primed template nucleic acid, the polymerase and the test nucleotide are capable of forming a ternary complex when the base of the test nucleotide is complementary to the next base of the primed template nucleic acid molecule. The primed template nucleic acid and the polymerase are capable of forming a binary complex when the base of the test nucleotide is not complementary to the next base of the primed template nucleic acid molecule. Optionally, the contacting occurs under conditions that favor formation of the ternary complex over formation of the binary complex. Optionally, the conditions that favor or stabilize the ternary complex are provided by either: (1) the presence of a reversible terminator moiety on the 3' nucleotide of the primer of the primed template nucleic acid molecule; or (2) the presence of a non-catalytic ion (e.g., a divalent or trivalent non-catalytic metal ion) that inhibits nucleotide incorporation or polymerization. Optionally, the conditions that disfavor or destabilize binary complexes are provided by the presence of one or more monovalent cations and/or glutamate anions in the reaction mixture during the examination step. Alternatively, a polymerase engineered to have reduced catalytic activity or reduced propensity for binary complex formation can be used. The determining or identifying step can include identifying the base of the nucleotide that is complementary to the next base of the primed template nucleic acid. This can be accomplished by detecting the polymerase of the ternary complex (e.g., via a label attached to the polymerase), and deducing identity of the cognate nucleotide from that identification.

The examination step conventionally is controlled so that nucleotide incorporation is attenuated. This being the case, a separate incorporation step (discussed elsewhere herein in greater detail) may be performed. The separate incorporation step may be accomplished without the need for monitoring, as the base has already been identified during the examination step. However if desired, subsequent incorporation can be detected, for example by incorporating nucleotides having exogenous labels. Detection at both binding and incorporation steps can provide for error checking and increased sequencing accuracy. A reversibly terminated nucleotide (whether labeled or not) may be used in the incorporation step to prevent the addition of more than one nucleotide during a single cycle.

The Sequencing By Binding™ method of the present disclosure allows for controlled determination of a template nucleic acid base (e.g., by identifying a next correct nucleotide) without the need for labeled nucleotides, as the interaction between the polymerase and template nucleic acid can be monitored without a label on the nucleotide. Template nucleic acid molecules may be sequenced under examination conditions which do not require attachment of template nucleic acid or polymerase to a solid support. However, in certain preferred embodiments, primed template nucleic acids to be sequenced are attached to a solid support, such as an interior surface of a flow cell. The compositions, methods and systems described herein provide numerous advantages over previous systems, such as controlled reaction conditions, unambiguous determination of sequence, long read lengths, low overall cost of reagents, and low instrument cost.

Alternatively or additionally to attaching primed template nucleic acids to a solid support, one or more polymerase molecules can be attached to the solid support. Attachment of polymerase to a solid support can provide an advantage in localizing the polymerase for a subsequent detection step. This can be useful for example, when screening polymerase variants for ability to form a stabilized ternary complex with a primed template nucleic acid and nucleotide that are delivered via solution phase. Alternatively, attachment of the polymerase can be useful for localizing the polymerase at a feature where a particular nucleic acid resides.

Optionally, the provided methods further include a wash step. The wash step can occur before or after any other step in the method. Optionally, the wash step is performed after each of the serially contacting steps, wherein the primed template nucleic acid molecule is contacted with one of the distinguishably labeled polymerase-nucleotide combinations. Optionally, the wash step is performed prior to the monitoring step and/or prior to the determining or identifying step. Optionally, the wash step occurs under conditions that stabilize the ternary complex. Optionally, the conditions result from the presence of a reversible terminator moiety on the 3' nucleotide of the primer of the primed template nucleic acid molecule. Optionally, the conditions include a stabilizing agent. Optionally, the stabilizing agent is a non-catalytic metal ion (e.g., a divalent non-catalytic metal ion) that inhibits nucleotide incorporation or polymerization. Non-catalytic metal ions include, but are not limited to, calcium, strontium, scandium, titanium, vanadium, chromium, iron, cobalt, nickel, copper, zinc, gallium, germanium, arsenic, selenium, rhodium, europium, and terbium ions. Optionally, the wash buffer includes nucleotides from previous contacting steps, but does not include the distinguishably labeled polymerase composition of a prior polymerase-nucleotide combination. Including the nucleotides from previous contacting steps can provide the advantage of stabilizing previously formed ternary complexes from unwanted disassociation. This in turn prevents unwanted loss of signal due to washing away previously formed ternary complexes or emergence of erroneous signals due to reconstitution between one or more component(s) of previously formed ternary complexes and one or more component(s) of an incoming reagent. Optionally, the ternary complex has a half-life and the wash step is performed for a duration shorter than the half-life of the ternary complex formed when a nucleotide molecule provides a base that is complementary to the next base of the primed template nucleic acid molecule.

The examination step may be controlled, in part, by providing reaction conditions to prevent chemical incorporation of a nucleotide, while allowing determination of the identity of the next correct base on the primed template nucleic acid molecule. Such reaction conditions may be referred to as examination reaction conditions. Optionally, a ternary complex is formed under examination conditions.

Optionally, the examination conditions accentuate the difference in affinity for polymerase to primed template nucleic acids in the presence of different nucleotides, for example by destabilizing binary complexes. Optionally, the examination conditions cause differential affinity of the polymerase for the primed template nucleic acid in the presence of different nucleotides. By way of example, the examination conditions that cause differential affinity of the polymerase for the primed template nucleic acid in the presence of different nucleotides include, but are not limited to, high salt and glutamate ions. For example, the salt may dissolve in aqueous solution to yield a monovalent cation, such as a monovalent metal cation (e.g., sodium ion or potassium ion). Optionally, the salt that provides the monovalent cations (e.g., monovalent metal cations) further provides glutamate anions. Optionally, the source of glutamate ions can be potassium glutamate. In some instances, the concentrations of potassium glutamate that can be used to alter polymerase affinity of the primed template nucleic acid extend from 10 mM to 1.6 M of potassium glutamate, or any amount in between 10 mM and 1.6 M. As indicated above, high salt refers to a concentration of salt from 50 to 1,500 mM salt.

Examination typically involves detecting polymerase interaction with a template nucleic acid where the interaction of the two different polymerase compositions (e.g., each containing a different polymerase, or a different combination of two polymerases) can be distinguished. Detection may include optical, electrical, thermal, acoustic, chemical and mechanical means. Optionally, examination is performed after a wash step, wherein the wash step removes any non-bound reagents (e.g., unbound polymerases and/or nucleotides) from the region of observation. This may occur at the end of a series of steps involving contacting of a primed template nucleic acid molecule with a plurality of distinguishable polymerase-nucleotide combinations. Optionally, examination is performed during a wash step, such that the dissociation kinetics of the polymerase-nucleic acid or polymerase-nucleic acid-nucleotide complexes may be monitored and used to determine the identity of the next base. Optionally, examination is performed during the course of addition of the examination reaction mixture (or first reaction mixture), such that the association kinetics of the polymerase to the nucleic acid may be monitored and used to determine the identity of the next base on the nucleic acid. Optionally, examination involves distinguishing ternary complexes from binary complexes of polymerase and nucleic acid. Optionally, examination is performed under equilibrium conditions where the affinities measured are equilibrium affinities. Multiple examination steps comprising different or similar examination reagents, may be performed sequentially to ascertain the identity of the next template base. Multiple examination steps may be utilized in cases where multiple template nucleic acids are being sequenced simultaneously in one sequencing reaction, wherein different nucleic acids react differently to the different examination reagents. Optionally, multiple examination steps may improve the accuracy of next base determination. Optionally, a single examination step is used to identify the next correct nucleotide, out of a plurality of possible nucleotides (e.g., four possible nucleotides), for different primed template nucleic acid molecules among a population.

Generally, the examination step involves binding a polymerase to the polymerization initiation site of a primed template nucleic acid in a reaction mixture comprising one or more nucleotides, and monitoring the interaction. Optionally, a nucleotide is sequestered within the polymerase-primed template nucleic acid complex to form a ternary complex, under conditions in which incorporation of the enclosed nucleotide by the polymerase is attenuated or inhibited. Optionally, the ternary complex is stabilized by the presence of a blocking moiety (e.g., a reversible terminator moiety) on the 3' terminal nucleotide of the primer. Optionally a stabilizer is added to stabilize the ternary complex in the presence of the next correct nucleotide. This ternary complex is in a stabilized or polymerase-trapped pre-chemistry conformation.

Optionally, the polymerase is trapped at the polymerization site in its ternary complex by one or a combination of means, not limited to, crosslinking of the polymerase domains, crosslinking of the polymerase to the nucleic acid, polymerase mutations that stabilize the ternary complex, allosteric inhibition by small molecules, uncompetitive inhibitors, competitive inhibitors, non-competitive inhibitors, and denaturation; wherein the formation of the trapped ternary complex provides information about the identity of the next base on the nucleic acid template.

Contacting Steps

In the provided methods, contacting of the primed template nucleic acid molecule with a reaction mixture that includes a polymerase composition and one nucleotide optionally occurs under conditions that stabilize formation of the ternary complex, and that destabilize formation of binary complexes. These conditions can be provided by alternative approaches that are a matter of choice by the end-user.

Optionally, the conditions comprise contacting the primed template nucleic acid molecule with a buffer that regulates osmotic pressure. Optionally, the reaction mixture used in the examination step includes the buffer that regulates osmotic pressure. Optionally, the buffer is a high salt buffer that includes a monovalent ion, such as a monovalent metal ion (e.g., potassium ion or sodium ion) at a concentration of from 50 to 1,500 mM. Salt concentrations in the range of from 100 to 1,500 mM, and from 200 to 1,500 mM also are highly preferred. Optionally, the buffer further includes a source of glutamate ions (e.g., potassium glutamate). Optionally, the conditions that stabilize formation of the ternary complex involve contacting the primed template nucleic acid molecule with a stabilizing agent. Optionally, the reaction mixture used during the examination step includes a stabilizing agent. Optionally, the stabilizing agent is a non-catalytic metal ion (e.g., a divalent or trivalent non-catalytic metal ion). Non-catalytic metal ions useful in this context include, but are not limited to, calcium, strontium, scandium, titanium, vanadium, chromium, iron, cobalt, nickel, copper, zinc, gallium, germanium, arsenic, selenium, rhodium, europium, and terbium.

Optionally, the contacting step is facilitated by the use of a flow cell or chamber, multiwell plate, etc. Flowing liquid reagents through the flow cell, which contains an interior solid support surface (e.g., a planar surface), conveniently permits reagent exchange or replacement. Immobilized to the interior surface of the flow cell is one or more primed template nucleic acids to be sequenced or interrogated using the procedures described herein. Typical flow cells will include microfluidic valving that permits delivery of liquid reagents (e.g., components of the "reaction mixtures" discussed herein) to an entry port. Liquid reagents can be removed from the flow cell by exiting through an exit port.

As discussed above, in certain embodiments it is desirable to avoid mixing one distinguishably labeled polymerase-nucleotide combination reagent with a subsequent polymerase-nucleotide combination reagent during the plurality of serial contacting steps. This can be accomplished by including an intervening wash step between each of the serial contacting steps. This may be done by alternatively flowing a binding mixture that includes a polymerase-nucleotide combination reagent and a wash solution through a flow cell. By another approach, robotic fluid handling may be used to perform reagent exchanges when using a multi-well formatted platform.

Detecting Steps

Detecting (e.g., via monitoring or measuring) the interaction of a polymerase with a primed template nucleic acid molecule and a cognate nucleotide molecule (i.e., detecting ternary complex formation) may be accomplished in many different ways. For example, monitoring can include measuring association kinetics for the interaction between the primed template nucleic acid, the polymerase, and any one of the four nucleotide molecules. Monitoring the interaction of the polymerase with the primed template nucleic acid molecule in the presence of a nucleotide molecule can include measuring equilibrium binding constants between the polymerase and primed template nucleic acid molecule (i.e., equilibrium binding constants of polymerase to the template nucleic acid in the presence of any one or the four nucleotides). Thus, for example, the monitoring includes measuring the equilibrium binding constant of the polymerase to the primed template nucleic acid in the presence of any one of the four nucleotides. Monitoring the interaction of the polymerase with the primed template nucleic acid molecule in the presence of a nucleotide molecule includes, for example, measuring dissociation kinetics of the polymerase from the primed template nucleic acid in the presence of any one of the four nucleotides. Optionally, monitoring the interaction of the polymerase with the primed template nucleic acid molecule in the presence of a nucleotide molecule includes measuring dissociation kinetics of the dissociation of the closed-complex (i.e., dissociation of the primed template nucleic acid, the polymerase, and any one of the four nucleotide molecules). Optionally, the measured association kinetics are different depending on the identity of the nucleotide molecule. Optionally, the polymerase has a different affinity for each of the four types of nucleotide molecules. Optionally, the polymerase has a different dissociation constant for each of the four types of nucleotide molecules in each type of ternary complex. Association, equilibrium and dissociation kinetics are known and can be readily determined by one in the art. See, for example, Markiewicz et al., Nucleic Acids Research 40(16):7975-84 (2012); Xia et al., J. Am. Chem. Soc. 135(1):193-202 (2013); Brown et al., J. Nucleic Acids, Article ID 871939, 11 pages (2010); Washington, et al., Mol. Cell. Biol. 24(2):936-43 (2004); Walsh and Beuning, J. Nucleic Acids, Article ID 530963, 17 pages (2012); and Roettger, et al., Biochemistry 47(37):9718-9727 (2008), which are incorporated by reference herein in their entireties.

The detecting step can include monitoring the steady state interaction of the polymerase with the primed template nucleic acid molecule in the presence of the first nucleotide molecule, without chemical incorporation of the first nucleotide molecule into the primer of the primed template nucleic acid molecule. Optionally, the detecting includes monitoring dissociation of the polymerase with the primed template nucleic acid molecule in the presence of the first nucleotide molecule, without chemical incorporation of the first nucleotide molecule into the primer of the primed template nucleic acid molecule. Optionally, the detecting includes monitoring association of the polymerase with the primed template nucleic acid molecule in the presence of the first nucleotide molecule, without chemical incorporation of the first nucleotide molecule into the primer of the primed template nucleic acid molecule. Again, the test nucleotides in these procedures may be native nucleotides (i.e., unlabeled), labeled nucleotides (e.g., including fluorescent or Raman scattering labels), or nucleotide analogs (e.g., nucleotides modified to include reversible terminator moieties with or without detectable label moieties). It will be understood that a detection technique can accumulate signal over a relatively brief duration as is typically understood to be a single timepoint acquisition or, alternatively, signal can be continuously monitored over time as is typical of a time-based acquisition. It is also possible to acquire a series of timepoints to obtain a time-based acquisition.

In some embodiments of the methods provided herein, a chemical block on the 3' nucleotide of the primer of the primed template nucleic acid molecule (e.g., a reversible terminator moiety on the base or sugar of the nucleotide), or the absence of a catalytic metal ion in the reaction mixture, or the absence of a catalytic metal ion in the active site of the polymerase prevents the chemical incorporation of the nucleotide into the primer of the primed template nucleic acid. Optionally, the chelation of a catalytic metal ion in the reaction mixtures of the contacting step prevents the chemical incorporation of the nucleotide into the primer of the primed template nucleic acid. Optionally, a non-catalytic metal ion acts as a stabilizer for the ternary complex in the presence of the next correct nucleotide. Optionally, the substitution of a catalytic metal ion in the reaction mixtures of the contacting step with a non-catalytic metal ion prevents the chemical incorporation of the nucleotide molecule to the primed template nucleic acid. Optionally, the catalytic metal ion is magnesium. The metal ion mechanisms of polymerases postulate that a low concentration of metal ions may be needed to stabilize the polymerase-nucleotide-DNA binding interaction. See, for instance, Section 27.2.2, Berg J M, Tymoczko J L, Stryer L, Biochemistry 5th Edition, WH Freeman Press, 2002.

Optionally, a low concentration of a catalytic ion in the reaction mixture used during the examination step prevents the chemical incorporation of the nucleotide molecule to the primed template nucleic acid. Optionally, a low concentration is from about 1 µM to about 100 µM. Optionally, a low concentration is from about 0.5 µM to about 5 µM. Optionally, the reaction mixture used during the examination step includes cobalt ions and the incorporating step involves contacting with an incorporation reaction mixture that includes a higher concentration of cobalt ions as compared to the concentration of cobalt ions in the first reaction mixture.

In an exemplary sequencing reaction, the examination step involves formation and/or stabilization of a ternary complex including a polymerase, primed template nucleic acid, and nucleotide. Characteristics of the formation and/or release of the ternary complex can be detected to identify the enclosed nucleotide and therefore the next base in the template nucleic acid. Ternary complex characteristics can be dependent on the sequencing reaction components (e.g., polymerase, primer, template nucleic acid, nucleotide) and/or reaction mixture components and/or conditions.

The examination step involves detecting the interaction of a polymerase with a template nucleic acid in the presence of a nucleotide. The formation of a ternary complex may be detected or monitored. Optionally, the absence of formation of ternary complex is detected or monitored. Optionally, the dissociation of a ternary complex is monitored. Optionally, the incorporation step involves detecting or monitoring incorporation of a nucleotide. Optionally, the incorporation step involves detecting or monitoring the absence of nucleotide incorporation.

Any process of the examination and/or incorporation step may be detected or monitored. Optionally, a polymerase has a detectable tag (e.g., a fluorescent label or a Raman scattering tag). Optionally, the detectable tag or label on the polymerase is removable. Generally speaking, when using single-scan imaging, among the series of distinguishable polymerase and nucleotide combinations employed in the procedure, as few as two polymerases among the plurality of different polymerase-nucleotide combinations will harbor detectable labels. As indicated elsewhere herein, this can provide information about four different nucleotides based on monitoring ternary complex formation. A single polymerase label can be used when multiple scans (e.g., four independent scans) are performed.

Optionally, a nucleotide of a particular type is made available to a polymerase in the presence of a primed template nucleic acid molecule. The reaction is detected or monitored, wherein, if the nucleotide is a next correct nucleotide, the polymerase may be stabilized to form a ternary complex. If the nucleotide is an incorrect nucleotide, a ternary complex may still be formed; however, without the additional assistance of stabilizing agents or reaction conditions (e.g., absence of catalytic ions, polymerase inhibitors, salt), the ternary complex may dissociate. The rate of dissociation is dependent on the affinity of the particular combination of polymerase, template nucleic acid, and nucleotide, as well as reaction conditions. Optionally, the affinity is measured as an off-rate. Optionally, the affinity is different between different nucleotides for the ternary complex. For example, if the next base in the template nucleic acid downstream of the 3'-end of the primer is G, the polymerase-nucleic acid affinity, measured as an off-rate, is expected to be different based on whether dATP, dCTP, dGTP or dTTP (or analogs thereof) are added. In this case, dCTP would have the slowest off-rate, with the other nucleotides providing different off-rates for the interaction. Optionally, the off-rate may be different depending on the reaction conditions, for example, the presence of stabilizing agents (e.g., absence of magnesium or inhibitory compounds) or reaction conditions (e.g., nucleotide modifications or modified polymerases).

Once the identity of the next correct nucleotide is determined, 1, 2, 3, 4 or more nucleotide types may be introduced simultaneously to the reaction mixture under conditions that specifically target the formation of a ternary complex. Excess nucleotides optionally may be removed from the reaction mixture and the reaction conditions modulated to incorporate the next correct nucleotide of the ternary complex. This sequencing reaction ensures that only one nucleotide is incorporated per sequencing cycle. Preferably, reversible terminator nucleotides are employed in the incorporation step, and optionally, the reversible terminator nucleotides are not labeled with fluorescent or other labels.

Identifying Steps

The identity of the next correct base or nucleotide can be determined by detecting the presence, formation, and/or dissociation of the ternary complex. The identity of the next correct nucleotide may be determined without covalently incorporating the nucleotide into to the primer at its 3'-end. Optionally, the identity of the next base is determined by detecting the affinity of the polymerase and the primed template nucleic acid in the presence of added nucleotides. Optionally, the affinity of the polymerase and the primed template nucleic acid in the presence of the next correct nucleotide may be used to determine the next correct base on the template nucleic acid. Optionally, the affinity of the polymerase to the primed template nucleic acid in the presence of an incorrect nucleotide may be used to determine the next correct base on the template nucleic acid.

In certain embodiments, a ternary complex that includes a primed template nucleic acid (or a blocked primed template nucleic acid) is formed in the presence of a polymerase and a plurality of nucleotides. Cognate nucleotide participating in the ternary complex optionally is identified by observing destabilization of the complex that occurs when the cognate nucleotide is absent from the reaction mixture. This is conveniently carried out, for example, by exchanging one reaction mixture for another. Here, loss of the complex is an indicator of cognate nucleotide identity. Loss of binding signal (e.g., a fluorescent binding signal associated with a particular locus on a solid support) can occur when the primed template nucleic acid is exposed to a reaction mixture that does not include the cognate nucleotide. Optionally, maintenance of a ternary complex in the presence of a single nucleotide in a reaction mixture also can indicate identity of the cognate nucleotide. When reversible terminator nucleotides are employed, removal of excess nucleotides is unnecessary because only a single reversible terminator nucleotide can be incorporated before the reversible terminator moiety is removed.

Incorporation Steps

Optionally, incorporation proceeds after the cognate nucleotide has been identified in an examination procedure using a first polymerase, or after signals (or other information) required to make the cognate nucleotide identification has been gathered. Incorporation optionally may employ a polymerase different from the one used in the examination step, together with a nucleotide analog. For example, the nucleotide analog can be an unlabeled reversible terminator nucleotide corresponding to the identified cognate nucleotide (i.e., the reversible terminator nucleotide and the cognate nucleotide are both complementary to the same base of the template strand). Also significantly, cognate nucleotides for a plurality of different primed template nucleic acids having different sequences advantageously can be identified using only a single imaging step. This is sometimes referred to as "single-scan imaging." Thus, the provided approach is both simple to implement and rapid to analyze.

The methods described herein optionally include an incorporation step. The incorporation step involves covalently incorporating one or more nucleotides at the 3'-end of a primer hybridized to a template nucleic acid. In a preferred embodiment, only a single nucleotide is incorporated at the 3'-end of the primer. Optionally, multiple nucleotides of the same kind are incorporated at the 3'-end of the primer. Optionally, multiple nucleotides of different kinds are incorporated at the 3'-end of the primer. Incorporated nucleotides alternatively can be unlabeled nucleotides, reversible terminator nucleotides, or detectably labeled nucleotide analogs. The polymerase can dissociate from the polymerization initiation site after nucleotide incorporation or can be retained at the polymerization initiation site after incorporation.

The incorporation reaction may be facilitated by an incorporation reaction mixture. Optionally, the incorporation reaction mixture has a different composition of nucleotides than the examination reaction. For example, the examination reaction can include one type of nucleotide and the incorporation reaction can include another type of nucleotide. Optionally, the incorporation reaction includes a polymerase that is different from the polymerases of the examination step. By way of another example, the examination reaction comprises one type of nucleotide and the incorporation reaction comprises four types of nucleotides, or vice versa. In yet another example, the examination reaction uses four different reagents, each containing one of four types of nucleotides, such that the four types of nucleotides are sequentially present, and the incorporation reaction can include the four types of nucleotides in a simultaneous mixture. As a further example, a first examination reaction can introduce a first type of nucleotide, a second examination reaction can introduce a second type of nucleotide along with the first type of nucleotide, a third examination reaction can introduce a third type of nucleotide along with the first and second types of nucleotides, a fourth examination reaction can introduce a fourth type of nucleotide along with the first, second and third types of nucleotides, and the incorporation reaction can include the first, second, third and fourth types of nucleotides in a simultaneous mixture. Optionally, an examination reaction mixture is altered or replaced by an incorporation reaction mixture. Optionally, an incorporation reaction mixture includes a catalytic metal ion (e.g., a divalent catalytic metal ion), a monovalent metal cation (e.g., potassium ions or sodium ions), glutamate ions, or a combination thereof.

There is flexibility in the nature of the nucleotide used in the incorporation step. For example, the at least one nucleotide can include a 3'-hydroxyl group, which can be, for example, a free 3'-hydroxyl group. Optionally, the 3' position of the at least one nucleotide molecule is modified to include a 3' terminator moiety. The 3' terminator moiety may be a reversible terminator or may be an irreversible terminator. Optionally, the reversible terminator nucleotide includes a 3'-ONH$_2$ moiety attached at the 3' position of the sugar moiety. Optionally, the reversible terminator of the at least one nucleotide molecule is replaced or removed before or after the examination step. Further examples of useful reversible terminator moieties are described, for example, in Bentley et al., Nature 456:53-59 (2008), WO 04/018497;

U.S. Pat. No. 7,057,026; WO 91/06678; WO 07/123744; U.S. Pat. Nos. 7,329,492; 7,211,414; 7,315,019; 7,405,281, and US 2008/0108082, each of which is incorporated herein by reference.

Nucleotides present in the reaction mixture but not sequestered in a ternary complex may cause multiple nucleotide insertions. A wash step can be employed prior to the chemical incorporation step to promote or ensure only the nucleotide sequestered within a trapped ternary complex being available for incorporation during the incorporation step. Optionally, free nucleotides may be removed or inactivated by enzymes such as phosphatases. The trapped polymerase complex may be a ternary complex, a stabilized ternary complex or ternary complex involving the polymerase, primed template nucleic acid and next correct nucleotide.

Optionally, the nucleotide enclosed within the ternary complex of the examination step is incorporated into the 3'-end of the template nucleic acid primer during the incorporation step. For example, a stabilized ternary complex of the examination step includes an incorporated next correct nucleotide.

Optionally, the incorporation step involves replacing a nucleotide from the examination step and incorporating another nucleotide into the 3'-end of the template nucleic acid primer. The incorporation step can involve releasing a nucleotide from within a ternary complex (e.g., the nucleotide is a modified nucleotide or nucleotide analog) and incorporating a nucleotide of a different kind into the 3'-end of the primer of the primed template nucleic acid molecule. The nucleotides used in the incorporation and examination steps can be cognates for the same template nucleotide despite other differences in the structure of the two nucleotide types. Optionally, the released nucleotide is removed and replaced with an incorporation reaction mixture containing a next correct nucleotide. For example, the incorporated nucleotide can be a reversible terminator nucleotide, such as an unlabeled reversible terminator nucleotide that does not include a detectable fluorophore. In this example, the incorporated nucleotide can be a cognate for the same template nucleotide as the nucleotide that was released.

Suitable reaction conditions for incorporation may involve replacing the examination reaction mixture with an incorporation reaction mixture. Optionally, nucleotide(s) present in the examination reaction mixture are replaced with one or more nucleotides in the incorporation reaction mixture. Optionally, the polymerase(s) present during the examination step is replaced during the incorporation step. By this approach it is possible to employ different types of polymerase in the examination and incorporation steps. Optionally, the polymerase present during the examination step is modified during the incorporation step. Optionally, the one or more nucleotides present during the examination step are modified during the incorporation step. The reaction mixture and/or reaction conditions present during the examination step may be altered by any means during the incorporation step. These means include, but are not limited to, removing reagents, chelating reagents, diluting reagents, adding reagents, altering reaction conditions such as conductivity or pH, and any combination thereof.

Optionally, the reaction mixture employed in the incorporation step includes competitive inhibitors, where the competitive inhibitors reduce the occurrence of multiple incorporations. In one embodiment, the competitive inhibitor is a non-incorporable nucleotide. In one embodiment, the competitive inhibitor is an aminoglycoside. In some embodiments, the competitive inhibitor is capable of replacing either the nucleotide or the catalytic metal ion in the active site, such that after the first incorporation the competitive inhibitor occupies the active site preventing a second incorporation. In some embodiments, both an incorporable nucleotide and a competitive inhibitor are introduced in the incorporation step, such that the ratio of the incorporable nucleotide and the inhibitor can be adjusted to ensure incorporation of a single nucleotide at the 3'-end of the primer.

Optionally, the provided reaction mixture(s), including the incorporation reaction mixture(s), include at least one nucleotide molecule that is a non-incorporable nucleotide or a nucleotide incapable of incorporation into the nucleic acid strand. In other words, the provided reaction mixture(s) can include one or more nucleotide molecules incapable of incorporation into the primer of the primed template nucleic acid molecule. Such nucleotides incapable of incorporation include, for example, monophosphate and diphosphate nucleotides. In another example, the nucleotide may contain modification(s) to the triphosphate group that make the nucleotide non-incorporable. Examples of non-incorporable nucleotides may be found in U.S. Pat. No. 7,482,120, which is incorporated by reference herein in its entirety. Optionally, the primer may not contain a free hydroxyl group at its 3'-end, thereby rendering the primer incapable of incorporating any nucleotide, and, thus, making any nucleotide non-incorporable.

A polymerase inhibitor optionally may be included with the reaction mixtures containing test nucleotides in the examination step to trap the polymerase on the nucleic acid upon binding the next correct nucleotide. Optionally, the polymerase inhibitor is a pyrophosphate analog. Optionally, the polymerase inhibitor is an allosteric inhibitor. Optionally, the polymerase inhibitor is a DNA or an RNA aptamer. Optionally, the polymerase inhibitor competes with a catalytic ion-binding site in the polymerase. Optionally, the polymerase inhibitor is a reverse transcriptase inhibitor. The polymerase inhibitor may be an HIV-1 reverse transcriptase inhibitor or an HIV-2 reverse transcriptase inhibitor. The HIV-1 reverse transcriptase inhibitor may be a (4/6-halogen/MeO/EtO-substituted benzo[d]thiazol-2-yl)thiazolidin-4-one.

The provided method may further include preparing the primed template nucleic acid molecule for a next examination step after the incorporation step. Optionally, the preparing includes subjecting the primed template nucleic acid or the nucleic acid/polymerase complex to one or more wash steps; a temperature change; a mechanical vibration; a pH change; a chemical treatment to remove reversible terminator moieties; or an optical stimulation. Optionally, the wash step comprises contacting the primed template nucleic acid or the primed template nucleic acid/polymerase complex with one or more buffers, detergents, protein denaturants, proteases, oxidizing agents, reducing agents, or other agents capable of releasing internal crosslinks within a polymerase or crosslinks between a polymerase and nucleic acid.

In the provided sequencing methods, signals used to identify the next base can be detected before the incorporation step, allowing the incorporation step to not require labeled reagents and/or monitoring. Thus, in the provided methods, a nucleotide, optionally, does not contain an attached detectable tag or label. Optionally, the nucleotide contains a detectable label, but the label is not detected in the method. Optionally, the nucleotide includes a label that is detected to indicate ternary complex formation, and the polymerase does not include any label (such as an energy transfer label) that is detected to indicate ternary complex formation. The label can be unique to a particular type of nucleotide such that it is distinguished from other types of nucleotides when participating in a ternary complex or, alternatively, several different nucleotides can have the same label and ternary complexes having different nucleotide types can be distinguished based on separate deliveries of the different nucleotide types. Optionally, the correct nucleotide does not contain a detectable label; however, an incorrect or non-complementary nucleotide to the next base contains a detectable label.

The examination step of the sequencing reaction may be repeated 1, 2, 3, 4 or more times prior to the incorporation step. The examination and incorporation steps may be repeated for a predefined number of cycles, until the desired sequence of the template nucleic acid is obtained or until certain reaction criteria are reached such as a minimum signal intensity or signal to noise ratio.

Reaction Mixtures

Nucleic acid sequencing reaction mixtures, or simply "reaction mixtures," can include one or more reagents that are commonly present in polymerase-based nucleic acid synthesis reactions. Reaction mixture reagents include, but are not limited to, enzymes (e.g., polymerase(s)), dNTPs (or analogs thereof), template nucleic acids, primer nucleic acids (including 3' blocked primers that cannot be extended by phosphodiester bond formation), salts, buffers, small molecules, co-factors, metals, and ions. The ions may be catalytic ions, divalent catalytic ions, non-catalytic ions, non-covalent metal ions, or a combination thereof. The reaction mixture can include salts, such as NaCl, KCl, potassium acetate, ammonium acetate, potassium glutamate, $NH_4Cl$, or $(NH_4HSO_4)$, that ionize in aqueous solution to yield monovalent cations. The reaction mixture can include a source of ions, such as $Mg^{2+}$ or $Mn^{2+}$, $Co^{2+}$, $Cd^{2+}$ or $Ba^{2+}$ ions. The reaction mixture can include tin, $Ca^{2+}$, $Zn^{2+}$, $Cu^{2+}$, $Co^{2+}$, $Fe(II)SO_4$, or $Ni^{2+}$, or other divalent or trivalent non-catalytic metal cation that stabilizes ternary complexes by inhibiting formation of phosphodiester bonds between the primed template nucleic acid molecule and the cognate nucleotide.

The buffer can include Tris, Tricine, HEPES, MOPS, ACES, MES, phosphate-based buffers, and acetate-based buffers. The reaction mixture can include chelating agents such as EDTA, EGTA, and the like. Optionally, the reaction mixture includes cross-linking reagents. Provided herein are first reaction mixtures, optionally, used during the examination step, as well as incorporation reaction mixtures used during nucleotide incorporation that can include one or more of the aforementioned agents. First reaction mixtures when used during examination can be referred to herein as examination reaction mixtures. Optionally, the first reaction mixture comprises a high concentration of salt; a high pH; 1, 2, 3, 4, or more types of nucleotides; potassium glutamate; a chelating agent; a polymerase inhibitor; a catalytic metal ion; a non-catalytic metal ion; or any combination thereof. The first reaction mixture can include 10 mM to 1.6 M of potassium glutamate (including any amount between 10 mM and 1.6 M). Optionally, the incorporation reaction mixture comprises a catalytic metal ion; 1, 2, 3, 4, or more types of nucleotides; potassium chloride; a non-catalytic metal ion; or any combination thereof.

The provided methods can be conducted under reaction conditions that modulate the formation and stabilization of a ternary complex during an examination step. The reaction conditions of the examination step typically favor the formation and/or stabilization of a ternary complex encapsulating a nucleotide and hinder the formation and/or stabilization of a binary complex. The binary interaction between the polymerase and template nucleic acid may be manipulated by modulating sequencing reaction parameters such as ionic strength, pH, temperature, or any combination thereof, or by the addition of a binary complex destabilizing agent to the reaction. Optionally, high salt (e.g., 50 to 1,500 mM) and/or pH changes are utilized to destabilize a binary complex. Optionally, a binary complex may form between a polymerase and a template nucleic acid during the examination or incorporation step of the sequencing reaction, regardless of the presence of a nucleotide. Optionally, the reaction conditions favor the stabilization of a ternary complex and destabilization of a binary complex. By way of example, the pH of the examination reaction mixture can be adjusted from 4.0 to 10.0 to favor the stabilization of a ternary complex and destabilization of a binary complex. Optionally, the pH of the examination reaction mixture is from 4.0 to 6.0. Optionally, the pH of the examination reaction mixture is 6.0 to 10.0.

The provided sequencing methods disclosed herein can function to promote polymerase interaction with the nucleotides and template nucleic acid in a manner that reveals the identity of the next base while controlling the chemical addition of a nucleotide. Optionally, the methods are performed in the absence of detectably labeled nucleotides, or in the presence of labeled nucleotides wherein the labels are not detected or not distinguished from each other. Optionally, only the nucleotides harbor labels that are detected as indicators of ternary complex formation (i.e., the polymerase does not include any label that is detected, including energy transfer labels that transfer or receive energy from labeled nucleotides). Optionally, only the polymerase harbors a detectable label (e.g., fluorescent detectable label, and only the label of the polymerase is detected in the procedure. Preferably, when the polymerase includes a detectable label, the detectable label produces a signal that does not change upon interaction with a cognate or non-cognate nucleotide. For example, the detectable label does not participate in energy transfer to or from a labeled nucleotide, or to or from another label that indicates conformational states of the polymerase.

Provided herein are methods for the formation and/or stabilization of a ternary complex comprising a polymerase bound to a primed template nucleic acid and a nucleotide enclosed within the polymerase-template nucleic acid complex, under examination reaction conditions. Examination reaction conditions may inhibit or attenuate nucleotide incorporation. Optionally, incorporation of the enclosed nucleotide is inhibited and the complex is stabilized or trapped in a pre-chemistry conformation or a ternary complex. Optionally, the enclosed nucleotide is incorporated and a subsequent nucleotide incorporation is inhibited. In this instance, the complex may be stabilized or trapped in a pre-translocation conformation. For the sequencing reactions provided herein, the ternary complex is stabilized during the examination step, allowing for controlled nucleotide incorporation. Optionally, a stabilized ternary complex is a complex wherein incorporation of an enclosed nucleotide is attenuated, either transiently (e.g., to examine the complex and then incorporate the nucleotide) or permanently (e.g., for examination only) during an examination step. Optionally, a stabilized ternary complex allows for the incorporation of the enclosed nucleotide, but does not allow for the incorporation of a subsequent nucleotide. Optionally, the closed-complex is stabilized in order to monitor any polymerase interaction with a template nucleic acid in the presence of a nucleotide for identification of the next base in the template nucleic acid.

Optionally, the enclosed nucleotide has severely reduced or disabled binding to the template nucleic acid in the ternary complex. Optionally, the enclosed nucleotide is base-paired to the template nucleic acid at a next base. Optionally, the identity of the polymerase, nucleotide, primer, template nucleic acid, or any combination thereof, affects the interaction between the enclosed nucleotide and the template nucleic acid in the ternary complex.

Optionally, the enclosed nucleotide is bound to the polymerase of the closed-complex. Optionally, the enclosed nucleotide is weakly associated with the polymerase of the ternary complex. Optionally, the identity of the polymerase, nucleotide, primer, template nucleic acid, or any combination thereof, affects the interaction between the enclosed nucleotide and the polymerase in the ternary complex. For a given polymerase, each nucleotide has a different affinity for the polymerase than another nucleotide. Optionally, a plurality of nucleotides, for example, all of the nucleotide types that have been used in reagents of the previous steps of the cycle, is present in a wash buffer. Optionally, the plurality of polymerases includes two polymerases that harbor distinguishable detectable labels, and the polymerases are components of a combination used with a single nucleotide. Optionally, this affinity is dependent, in part, on the template nucleic acid and/or the primer.

Optionally, the examination reaction condition comprises a plurality of primed template nucleic acids, polymerases, nucleotides, or any combination thereof. Optionally, the plurality of nucleotides comprises at least 1, 2, 3, 4, or more types of different nucleotides, for example dATP, dTTP (or dUTP), dGTP, and dCTP. Alternatively or additionally, the plurality of nucleotides comprises at most 1, 2, 3, or 4 types of different nucleotides, for example dATP, dTTP (or dUTP), dGTP, and dCTP. Optionally, the plurality of nucleotides comprises one or more types of nucleotides that, individually or collectively, complement at least 1, 2, 3 or 4 types of nucleotides in a template, for example dATP, dTTP (or dUTP), dGTP, or dCTP. Alternatively or additionally, the plurality of nucleotides comprises one or more types of nucleotides that, individually or collectively, complement at most 1, 2, 3 or 4 types of nucleotides in a template, for example dATP, dTTP (or dUTP), dGTP, or dCTP. Optionally, the plurality of template nucleic acids is a clonal population of template nucleic acids.

Optionally, the examination reaction mixture comprises one or more reagents or biomolecules generally present in a nucleic acid polymerization reaction. Reaction components used in addition to those set forth herein, may include, but are not limited to, salts, buffers, small molecules, detergents, crowding agents, metals, and ions. Optionally, properties of the reaction mixture may be manipulated, for example, electrically, magnetically, and/or with vibration.

Useful Nucleotides and Nucleotide Analogs

Optionally, a ternary complex of an examination step comprises either a native nucleotide, or a nucleotide analog or modified nucleotide to facilitate stabilization of the ternary complex. Optionally, a nucleotide analog comprises a nitrogenous base, five-carbon sugar, and phosphate group; wherein any moiety of the nucleotide may be modified, removed and/or replaced. Nucleotide analogs may be non-incorporable nucleotides. Non-incorporable nucleotides may be modified to become incorporable at any point during the sequencing method. Optionally, a nucleotide analog includes a detectable label attached to any of a phosphate moiety, a base moiety, and a sugar moiety of the nucleotide analog.

Nucleotide analogs include, but are not limited to, alpha-phosphate modified nucleotides, alpha-beta nucleotide analogs, beta-phosphate modified nucleotides, beta-gamma nucleotide analogs, gamma-phosphate modified nucleotides, caged nucleotides, or ddNTPs. Examples of nucleotide analogs are described in U.S. Pat. No. 8,071,755, which is incorporated by reference herein in its entirety.

Nucleotide analogs can include terminators that reversibly prevent nucleotide incorporation at the 3'-end of the primer. For example, the terminator can reversibly prevent the 3' end of the nucleotide analog from reacting with another nucleotide after the nucleotide analog has been incorporated into the primer. One type of reversible terminator is a 3'-O-blocked reversible terminator. Here the terminator moiety is linked to the oxygen atom of the 3'-OH end of the 5-carbon sugar of a nucleotide. For example, U.S. Pat. Nos. 7,544,794 and 8,034,923 (the disclosures of these patents are incorporated by reference) describe reversible terminator dNTPs having the 3'-OH group replaced by a 3'-$ONH_2$ group. Another type of reversible terminator is a 3'-unblocked reversible terminator, wherein the terminator moiety is linked to the nitrogenous base of a nucleotide. For example, U.S. Pat. No. 8,808,989 (the disclosure of which is incorporated by reference) discloses particular examples of base-modified reversible terminator nucleotides that may be used in connection with the methods described herein. Other reversible terminators that similarly can be used in connection with the methods described herein include those described in U.S. Pat. Nos. 7,956,171, 8,071,755, and 9,399,798 (the disclosures of these U.S. patents are incorporated by reference). For reviews of nucleotide analogs having terminators see e.g., Mu, R., et al., "The History and Advances of Reversible Terminators Used in New Generations of Sequencing Technology," Genomics, Proteomics & Bioinformatics 11(1):34-40 (2013). Optionally, one or more native nucleotides employed during the examination step is replaced by a second type of nucleotide that is incorporated during the incorporation step. For example, nucleotides present in the reaction mixture used during an examination step may be replaced by nucleotide analogs that include reversible terminator moieties (e.g., positioned on the base or sugar of the nucleotide molecule).

Optionally, nucleotide analogs have terminator moieties that irreversibly prevent nucleotide incorporation at the 3'-end of the primer. Irreversible terminator nucleotide analogs include, for example, 2', 3'-dideoxynucleotides, ddNTPs (ddGTP, ddATP, ddTTP, ddCTP). Dideoxynucleotides lack the 3'-OH group of dNTPs that is essential for polymerase-mediated synthesis.

Optionally, non-incorporable nucleotides comprise a blocking moiety that inhibits or prevents the nucleotide from forming a covalent linkage to a second nucleotide (3'-OH of a primer) during the incorporation step of a nucleic acid polymerization reaction. In certain embodiments, the blocking moiety can be removed from the nucleotide, allowing for nucleotide incorporation.

Optionally, a nucleotide analog present in a ternary complex renders the ternary complex stable. Optionally, the nucleotide analog is non-incorporable. Optionally, the nucleotide analog is released and a native nucleotide is incorporated. Optionally, the ternary complex is released, the nucleotide analog is modified, and the modified nucleotide analog is incorporated. Optionally, the ternary complex is released under reaction conditions that modify and/or destabilize the nucleotide analog in the ternary complex.

Optionally, a nucleotide analog present in a ternary complex is incorporated and the ternary complex is stabilized. The ternary complex may be stabilized by the nucleotide analog, or for example, by any stabilizing methods disclosed herein. Optionally, the nucleotide analog does not allow for the incorporation of a subsequent nucleotide. The ternary complex can be released, for example, by any methods described herein, and the nucleotide analog is modified. The modified nucleotide analog may allow for subsequent incorporation of a nucleotide to its 3'-end.

Optionally, a nucleotide analog is present in the reaction mixture during the examination step. For example, 1, 2, 3, 4 or more nucleotide analog types are present in the reaction mixture during the examination step. Similarly, one or more nucleotide analog types that are present in the reaction mixture during the examination step can be complementary to at least 1, 2, 3 or 4 nucleotide types in a template nucleic acid. Optionally, a nucleotide analog is replaced, diluted, or sequestered during an incorporation step. Optionally, a nucleotide analog is replaced with a native nucleotide. In this option, the nucleotide analog and native nucleotide can have base moieties that are cognates for the same type of template nucleotide. The native nucleotide may include a next correct nucleotide. Optionally, a nucleotide analog is modified during an incorporation step. The modified nucleotide analog can be similar to or the same as a native nucleotide.

Optionally, a nucleotide analog has a different binding affinity for a polymerase than a native nucleotide. Optionally, a nucleotide analog has a different interaction with a next base than a native nucleotide. Nucleotide analogs and/or non-incorporable nucleotides may base-pair with a complementary base of a template nucleic acid.

Optionally, a nucleotide analog is a nucleotide, modified or native, fused to a polymerase. Optionally, a plurality of nucleotide analogs comprises fusions to a plurality of polymerases, wherein each nucleotide analog comprises a different polymerase.

Any nucleotide modification that traps the polymerase in a ternary complex may be used in the methods disclosed herein. The nucleotide may be trapped permanently or transiently. Optionally, the nucleotide analog is not the means by which a closed-complex is stabilized. Any ternary complex stabilization method may be combined in a reaction utilizing a nucleotide analog.

Optionally, a nucleotide analog that allows for the stabilization of a closed-complex is combined with reaction conditions that usually release the ternary complex. The conditions include, but are not limited to, the presence of a release reagent (e.g., catalytic metal ion, such as magnesium or manganese). Optionally, the ternary complex is stabilized even in the presence of a catalytic metal ion. Optionally, the ternary complex is released even in the presence of a nucleotide analog. Optionally, the stabilization of the closed-complex is dependent, in part, on the concentrations and/or identity of the stabilization reagent and/or release reagents, and any combination thereof. Optionally, the stabilization of a ternary complex using nucleotide analogs is combined with additional reaction conditions that function to stabilize a ternary complex, including, but not limited to, sequestering, removing, reducing, omitting, and/or chelating a catalytic metal ion; the presence of a polymerase inhibitor, cross-linking agent; and any combination thereof.

Optionally, one or more nucleotides can be labeled with distinguishing and/or detectable tags or labels. However in particular embodiments such tags or labels preferably are not detected during examination, identification of the base or incorporation of the base, and such tags or labels are not detected during the sequencing methods disclosed herein. The tags may be distinguishable by means of their differences in fluorescence, Raman spectrum, charge, mass, refractive index, luminescence, length, or any other measurable property. The tag may be attached to one or more different positions on the nucleotide, so long as the fidelity of binding to the polymerase-nucleic acid complex is sufficiently maintained to enable identification of the complementary base on the template nucleic acid correctly. Optionally, the tag is attached to the nucleobase of the nucleotide. Under suitable reaction conditions, the tagged nucleotides may be enclosed in a ternary complex with the polymerase and the primed template nucleic acid. Alternatively, a tag is attached to the gamma phosphate position of the nucleotide.

Useful Polymerase Compositions

The disclosed approach permits identification of a cognate nucleotide using the combination of a unique polymerase composition (e.g., a reagent including a polymerase that can be distinguished from others, such as a detectably labeled polymerase) and a single nucleotide (e.g., a native nucleotide) without incorporation of the nucleotide. While individually labeled polymerases may be used for each different nucleotide used in an examination step, mixtures of two different labeled polymerases alternatively can be used as a single unique polymerase composition. Generally speaking, the primer strand of a primed template nucleic acid molecule undergoing examination is chemically unchanged by the polymerase or any other enzyme during examination procedure that identifies the cognate nucleotide. This is to say that the primer is neither extended by formation of a new phosphodiester bond, nor shortened by nucleolytic degradation during the examination step to identify the next correct nucleotide.

It is to be understood that four distinguishable polymerase compositions do not necessarily require four different labeled polymerases. For example, two distinguishably labeled polymerases can be used in combination with two different nucleotides to yield two different polymerase-nucleotide combinations. Alternatively or additionally, a polymerase having both of the distinguishable labels or a mixture of the same two distinguishably labeled polymerases (i.e., representing a third distinct polymerase composition) can be used in combination with a third nucleotide to yield a third polymerase-nucleotide combination. Further alternatively or additionally, an unlabeled polymerase can be used in combination with a fourth nucleotide to yield a fourth polymerase-nucleotide combination (i.e., a "dark" combination). In some embodiments, use of a fourth polymerase-nucleotide combination can be avoided altogether, deducing by the absence of a signal indicating the cognate nucleotide is any of the first three nucleotides that the cognate must be, by default, the fourth nucleotide. By this approach, all four different cognate nucleotides can be identified using fewer than four different labels. For example, at most one, two, or three polymerases used in the four polymerase compositions can harbor distinguishable labels. Optionally, four different polymerases are labeled with four different detectable moieties (e.g., fluorescent moieties or Raman labels). This approach has successfully allowed for simultaneous detection of the next correct nucleotide in a multiplexed field of features by the technique described herein.

To further clarify this point, polymerase compositions that can be used with the disclosed technique typically include a plurality of distinguishable polymerases. For example, when four distinguishable polymerase-nucleotide combinations are being tested to identify a next correct nucleotide, there can be four polymerases, each harboring a different detectable label, where the different polymerases are independently paired with a single different nucleotide to create the four distinguishably labeled polymerase-nucleotide combinations. Alternatively, there can be three labeled polymerases, each harboring a different detectable label, where the different polymerases are independently paired with a single different nucleotide to create the three distinguishably labeled polymerase-nucleotide combinations. Here, the three distinguishably labeled polymerase-nucleotide combinations can be used for identifying three different cognate nucleotides, with a fourth cognate nucleotide being identified as the one that did not participate in formation of a ternary complex that included one of the other labeled polymerases. Finally, it is even possible to use as few as two different labeled polymerases to identify which of four candidate nucleotides is the next correct nucleotide. In this case, the two distinguishable labeled polymerases are independently paired with different single nucleotides to create the first two polymerase-nucleotide combinations. A third polymerase-nucleotide combination can be created from a mixture of the two distinguishably labeled polymerases (or with a polymerase being attached to both of the labels that were used in the first two polymerase-nucleotide combinations), with the mixture being paired with third nucleotide to create a third distinguishably labeled polymerase-nucleotide combination. Identity of a cognate nucleotide corresponding to the fourth nucleotide again can be made as the nucleotide that did not promote formation of a ternary complex with any of the first, second, or third distinguishably labeled polymerase-nucleotide combinations. This option to use fewer than four labeled polymerases for identifying four different cognate nucleotides optionally can be used for "polymerase barcoding" applications, wherein polymerase exchange is used. Again, cognate nucleotide identification can be made using the Sequencing By Binding™ technique and a single-scan imaging step.

Polymerases that may be used to carry out the disclosed techniques include naturally occurring polymerases and modified variations thereof, including, but not limited to, mutants, recombinants, fusions, genetic modifications, chemical modifications, synthetics, and analogs. Naturally occurring polymerases and modified variations thereof are not limited to polymerases that retain the ability to catalyze a polymerization reaction. Optionally, the naturally occurring and/or modified variations thereof retain the ability to catalyze a polymerization reaction. Optionally, the naturally-occurring and/or modified variations have special properties that enhance their ability to sequence DNA, including enhanced binding affinity to nucleic acids, reduced binding affinity to nucleic acids, enhanced binding affinity to nucleotides, reduced binding affinity to nucleotides, enhanced specificity for next correct nucleotides, reduced specificity for next correct nucleotides, enhanced catalysis rates, reduced catalysis rates, catalytic inactivity etc. Mutant polymerases include polymerases wherein one or more amino acids are replaced with other amino acids, and insertions or deletions of one or more amino acids.

Modified polymerases include polymerases that contain an external tag (e.g., an exogenous detectable label), which can be used to monitor the presence and interactions of the polymerase. Optionally, intrinsic signals from the polymerase can be used to monitor their presence and interactions. Thus, the provided methods can include monitoring the interaction of the polymerase, nucleotide and template nucleic acid through detection of an intrinsic signal from the polymerase. Optionally, the intrinsic signal is a light scattering signal. For example, intrinsic signals include native fluorescence of certain amino acids such as tryptophan, wherein changes in intrinsic signals from the polymerase may indicate the formation of a ternary complex.

Optionally, the polymerase employed during the examination step includes one or more exogenous detectable label (e.g., a fluorescent label or Raman scattering tag) chemically linked to the structure of the polymerase by a covalent bond. Optionally, the label(s) can be attached after the polymerase has been at least partially purified using protein isolation techniques. For example, the exogenous detectable label can be chemically linked to the polymerase using a free sulfhydryl or a free amine moiety of the polymerase. This can involve chemical linkage to the polymerase through the side chain of a cysteine residue, or through the free amino group of the N-terminus. An exogenous label can also be attached to a polymerase via protein fusion. Exemplary fluorescent labels that can be attached via protein fusion include, for example, Green Fluorescent Protein (and wavelength shifted variants thereof) and phycobiliproteins (e.g., phycocyanin, phycoerythrin and variants thereof). In certain preferred embodiments, a fluorescent label attached to the polymerase is useful for locating the polymerase, as may be important for determining whether or not the polymerase has localized to a feature or spot on an array corresponding to immobilized primed template nucleic acid. The fluorescent signal need not, and preferably does not change absorption or emission characteristics as the result of binding any nucleotide. Stated differently, the signal emitted by the labeled polymerase can be maintained substantially uniformly in the presence and absence of any nucleotide being investigated as a possible next correct nucleotide. In certain other preferred embodiments, the fluorescent signal emitted by the labeled polymerase is differentially affected by inclusion of the polymerase in binary and ternary complexes. Labels useful in this regard are known to those having an ordinary level of skill in the art.

The term polymerase and its variants, as used herein, also refers to fusion proteins comprising at least two portions linked to each other, for example, where one portion comprises a peptide that can catalyze the polymerization of nucleotides into a nucleic acid strand is linked to another portion that comprises a second moiety, such as, a reporter enzyme or a processivity-modifying domain. For example, T7 DNA polymerase comprises a nucleic acid polymerizing domain and a thioredoxin binding domain, wherein thioredoxin binding enhances the processivity of the polymerase. Absent the thioredoxin binding, T7 DNA polymerase is a distributive polymerase with processivity of only one to a few bases. Although DNA polymerases differ in detail, they have a similar overall shape of a hand with specific regions referred to as the fingers, the palm, and the thumb; and a similar overall structural transition, comprising the movement of the thumb and/or finger domains, during the synthesis of nucleic acids.

DNA polymerases include, but are not limited to, bacterial DNA polymerases, eukaryotic DNA polymerases, archaeal DNA polymerases, viral DNA polymerases and phage DNA polymerases. Bacterial DNA polymerases include *E. coli* DNA polymerases I, II and III, IV and V, the Klenow fragment of *E. coli* DNA polymerase, *Clostridium stercorarium* (Cst) DNA polymerase, *Clostridium thermocellum* (Cth) DNA polymerase and *Sulfolobus solfataricus* (Sso) DNA polymerase. Eukaryotic DNA polymerases include DNA polymerases α, β, γ, δ, ε, η, ζ, λ, σ, μ, and k, as well as the Rev1 polymerase (terminal deoxycytidyl transferase) and terminal deoxynucleotidyl transferase (TdT). Viral DNA polymerases include T4 DNA polymerase, phi-29 DNA polymerase, GA-1, phi-29-like DNA polymerases, PZA DNA polymerase, phi-15 DNA polymerase, Cp1 DNA polymerase, Cp7 DNA polymerase, T7 DNA polymerase, and T4 polymerase. Other DNA polymerases include thermostable and/or thermophilic DNA polymerases such as DNA polymerases isolated from *Thermus aquaticus* (Taq) DNA polymerase, *Thermus filiformis* (Tfi) DNA polymerase, *Thermococcus zilligi* (Tzi) DNA polymerase, *Thermus thermophilus* (Tth) DNA polymerase, *Thermus flavus* (Tfl) DNA polymerase, *Pyrococcus woesei* (Pwo) DNA polymerase, *Pyrococcus furiosus* (Pfu) DNA polymerase and Turbo Pfu DNA polymerase, *Thermococcus litoralis* (Tli) DNA polymerase, *Pyrococcus* sp. GB-D polymerase, *Thermotoga maritima* (Tma) DNA polymerase, *Bacillus stearothermophilus* (Bst) DNA polymerase, *Pyrococcus Kodakaraensis* (KOD) DNA polymerase, Pfx DNA polymerase, *Thermococcus* sp. JDF-3 (JDF-3) DNA polymerase, *Thermococcus gorgonarius* (Tgo) DNA polymerase, *Thermococcus acidophilium* DNA polymerase; *Sulfolobus acidocaldarius* DNA polymerase; *Thermococcus* sp. go N-7 DNA polymerase; *Pyrodictium occultum* DNA polymerase; *Methanococcus voltae* DNA polymerase; *Methanococcus thermoautotrophicum* DNA polymerase; *Methanococcus jannaschii* DNA polymerase; *Desulfurococcus* strain TOK DNA polymerase (D. Tok Pol); *Pyrococcus abyssi* DNA polymerase; *Pyrococcus horikoshii* DNA polymerase; *Pyrococcus islandicum* DNA polymerase; *Thermococcus fumicolans* DNA polymerase; *Aeropyrum pernix* DNA polymerase; and the heterodimeric DNA polymerase DP1/DP2. Engineered and modified polymerases also are useful in connection with the disclosed techniques. For example, modified versions of the extremely thermophilic marine archaea *Thermococcus* species 9° N (e.g., Therminator DNA polymerase from New England BioLabs Inc.; Ipswich, Mass.) can be used. Still other useful DNA polymerases, including the 3PDX polymerase are disclosed in U.S. Pat. No. 8,703,461, the disclosure of which is incorporated by reference in its entirety.

RNA polymerases include, but are not limited to, viral RNA polymerases such as T7 RNA polymerase, T3 polymerase, SP6 polymerase, and K11 polymerase; Eukaryotic RNA polymerases such as RNA polymerase I, RNA polymerase II, RNA polymerase III, RNA polymerase IV, and RNA polymerase V; and Archaea RNA polymerase.

Reverse transcriptases include, but are not limited to, HIV-1 reverse transcriptase from human immunodeficiency virus type 1 (PDB 1HMV), HIV-2 reverse transcriptase from human immunodeficiency virus type 2, M-MLV reverse transcriptase from the Moloney murine leukemia virus, AMV reverse transcriptase from the avian myeloblastosis virus, and Telomerase reverse transcriptase that maintains the telomeres of eukaryotic chromosomes.

Optionally, a polymerase is tagged with a chemiluminescent tag, wherein closed-complex formation is monitored as a stable luminescence signal in the presence of the appropriate luminescence triggers. The unstable interaction of the polymerase with the template nucleic acid in the presence of an incorrect nucleotide results in a measurably weaker signal compared to the ternary complex formed in the presence of the next correct nucleotide. Additionally, an optional wash step prior to triggering luminescence can remove substantially all polymerase molecules not bound in a stable ternary complex.

Optionally, a polymerase is tagged with an optical scattering tag, wherein ternary complex formation is monitored as a stable optical scattering signal. The unstable interaction of the polymerase with the nucleic acid in the presence of an incorrect nucleotide results in a measurably weaker signal compared to the ternary complex formed in the presence of the next correct nucleotide.

Optionally, the polymerase is tagged with a plasmonic nanoparticle tag, wherein the ternary complex formation is monitored as a shift in plasmonic resonance that is different from the plasmonic resonance in the absence of the ternary complex or the presence of a ternary complex comprising an incorrect nucleotide. The change in plasmon resonance may be due to the change in local dielectric environment in the ternary complex, or it may be due to the synchronous aggregation of the plasmonic nanoparticles on a cluster of clonally amplified nucleic acid molecules or another means that affects the plasmons differently in the closed-complex configuration.

Optionally, the polymerase is tagged with a Raman scattering tag, wherein, the ternary complex formation is monitored as a stable Raman scattering signal. The unstable interaction of polymerase with the nucleic acid in the presence of an incorrect nucleotide results in a measurably weaker signal compared to the ternary complex formed in the presence of the next correct nucleotide.

Optionally, a next correct nucleotide is identified by a tag on a polymerase selected or modified to have a high affinity for nucleotides, wherein the polymerase binds to a nucleotide prior to binding to the template nucleic acid. For example, the DNA polymerase X from the African Swine Fever virus has an altered order of substrate binding, where the polymerase first binds to a nucleotide, then binds to the template nucleic acid. Optionally, a polymerase is incubated with each type of nucleotide in separate compartments, where each compartment contains a different type of nucleotide and where the polymerase is labeled differently with a tag depending on the nucleotide with which it is incubated. In these conditions, unlabeled nucleotides are bound to differently labeled polymerases. The polymerases may be the same kind of polymerase bound to each nucleotide type or different polymerases bound to each nucleotide type. The differentially tagged polymerase-nucleotide complexes may be added simultaneously to any step of the sequencing reaction. Each polymerase-nucleotide complex binds to a template nucleic acid whose next base is complementary to the nucleotide in the polymerase-nucleotide complex. The next correct nucleotide is identified by the tag on the polymerase carrying the nucleotide. The interrogation of the next template base by the labeled polymerase-nucleotide complex may be performed under non-incorporating and/or examination conditions, where once the identity of the next template base is determined, the complex is destabilized and removed, sequestered, and/or diluted and a separate incorporation step is performed in a manner ensuring that only one nucleotide is incorporated.

A common method of introducing a detectable tag on a polymerase involves chemical conjugation to amines or cysteines present in the non-active regions of the polymerase. Such conjugation methods are well known in the art. As non-limiting examples, n-hydroxysuccinimide esters (NHS esters) are commonly employed to label amine groups that may be found on an enzyme. Cysteines readily react with thiols or maleimide groups, while carboxyl groups may be reacted with amines by activating them with EDC (1-Ethyl-3-[3-dimethylaminopropyl]carbodiimide hydrochloride). Optionally, N-Hydroxysuccinimide (NHS) chemistry is employed at pH ranges where only the N-terminal amines are reactive (for instance, pH 7), such that only a single tag is added per polymerase.

Optionally, the tag attached to the polymerase is a charge tag, such that the formation of stable ternary complex can be detected by electrical means by measuring changes in local charge density around the template nucleic acids. Methods for detecting electrical charges are well known in the art, comprising methods such as field-effect transistors, dielectric spectroscopy, impedance measurements, and pH measurements, among others. Field-effect transistors include, but are not limited to, ion-sensitive field-effect transistors (ISFET), charge-modulated field-effect transistors, insulated-gate field-effect transistors, metal oxide semiconductor field-effect transistors and field-effect transistors fabricated using semiconducting single wall carbon nanotubes.

Optionally, a charge tag is a peptide tag having an isoelectric point below about 4 or above about 10. Optionally, a polymerase comprising a peptide tag has a total isoelectric point below about 5 or above about 9. A charge tag may be any moiety which is positively or negatively charged. The charge tag may comprise additional moieties including mass and/or labels such as dyes. Optionally, the charge tag possesses a positive or negative charge only under certain reaction conditions such as changes in pH.

A polymerase optionally may be labeled with a fluorophore and/or quencher. Optionally, a nucleic acid is labeled with a fluorophore and/or quencher. Optionally, one or more nucleotides are labeled with a fluorophore and/or quencher. Exemplary fluorophores include, but are not limited to, fluorescent nanocrystals; quantum dots; green fluorescent protein and color shifted mutants thereof, phycobiliproteins such as phycocyanin and phycoerythrin, d-Rhodamine acceptor dyes including dichloro[R110], dichloro[R6G], dichloro[TAMRA], dichloro[ROX] or the like; fluorescein donor dye including fluorescein, 6-FAM, or the like; Cyanine dyes such as Cy3B; Alexa dyes, SETA dyes, Atto dyes such as atto 647N which forms a FRET pair with Cy3B and the like. Fluorophores include, but are not limited to, MDCC (7-diethylamino-3-[([(2-maleimidyl)ethyl]amino)carbonyl] coumarin), TET, HEX, Cy3, TMR, ROX, Texas Red, Cy5, LC red 705 and LC red 640. Fluorophores and methods for their use including attachment to polymerases and other molecules are described in The Molecular Probes® Handbook (Life Technologies, Carlsbad Calif.) and Fluorophores Guide (Promega, Madison, Wis.), which are incorporated herein by reference in their entireties. Exemplary quenchers include, but are not limited to, ZEN, IBFQ, BHQ-1, BHQ-2, DDQ-I, DDQ-11, Dabcyl, Qx1 quencher, Iowa Black RQ, and IRDye QC-1.

In certain preferred embodiments, the polymerase is labeled with a fluorescent detectable label, where the detectable label shows substantially no change in its fluorescent properties (excitation and emission) as the result of interaction with any nucleotide, or as the result of a conformational change to the polymerase itself. Thus, for example, polymerase signaling does not require energy transfer to or from the detectable label because of nucleotide interaction with the polymerase. Optionally, the detectable label of a distinguishably labeled polymerase is a fluorescent label, but the fluorescent label is not an intercalating dye that changes properties upon binding a primed template nucleic acid molecule.

Optionally, a conformationally sensitive dye may be attached close to the active site of the polymerase without affecting the polymerization ability or fidelity of the polymerase; wherein a change in conformation, or a change in polar environment due to the formation of a ternary complex is reflected as a change in fluorescence or absorbance properties of the dye. Common fluorophores such as Cy3 and fluorescein are known to have strong solvatochromatic response to polymerase binding and ternary complex formation, to the extent that the formation of ternary complex can be distinguished clearly from the binary polymerase-nucleic acid complex. Optionally, the ternary complex can be distinguished from binary complexes based on differences in fluorescence or absorbance signals from a conformationally sensitive dye. Optionally, a solvatochromatic dye may be employed to monitor conformational transitions; wherein the change in local polar environment induced by the conformational change can be used as the reporter signal. Solvatochromatic dyes include, but are not limited to, Reichart's dye, IR44, merocyanine dyes (e.g., merocyanine 540), 4-[2-N-substituted-1,4-hydropyridin-4-ylidine)ethylidene] cyclohexa-2,5-dien-1-one, red pyrazolone dyes, azomethine dyes, indoaniline dyes, diazamerocyanine dyes, indigoid dyes, as exemplified by indigo, and others as well as mixtures thereof. Methods to introduce dyes or fluorophores to specific sites of a polymerase are well known in the art. As a non-limiting example, a procedure for site specific labeling of a T7 DNA polymerase with a dye is provided in Analytical Biochemistry 384:136-44 (2009), which is incorporated by reference in its entirety.

Optionally, a polymerase is tagged with a fluorophore at a position that can sense ternary complex formation without interfering with the reaction. The polymerase may be a native or modified polymerase. Modified polymerases include those with one or more amino acid mutations, additions, and/or deletions. Optionally, one or more, but not all, cysteine amino acids are mutated to another amino acid, such as alanine. In this case, the remaining one or more cysteines are used for site-specific conjugation to a fluorophore. Alternatively, one or more amino acids are mutated to a reactive amino acid suitable for fluorophore conjugation, such as cysteines or amino acids comprising primary amines.

Optionally, binding between a polymerase and a template nucleic acid in the presence of a correct nucleotide may induce a decrease in fluorescence, whereas binding with an incorrect nucleotide causes an increase in fluorescence. Binding between a polymerase and a template nucleic acid in the presence of a correct nucleotide may induce an increase in fluorescence, whereas binding with an incorrect nucleotide causes a decrease in fluorescence. The fluorescent signals may be used to monitor the kinetics of a nucleotide-induced conformational change and identify the next base in the template nucleic acid sequence.

Optionally, the polymerase/nucleic-acid interaction may be monitored by scattering signal originating from the polymerase or tags attached to the polymerase, for instance, nanoparticle tags.

As discussed above, polymerases may be modified to facilitate ternary complex formation and/or stabilization during the examination step of the sequencing methods described herein. Thus, a modified polymerase may be used in the provided methods. Modifications of polymerases may include cross-linking the members within the ternary complex with cross-linkers or forming disulfide bonds within the polymerase to maintain a ternary complex.

Optionally, cysteine residues are positioned so that when a ternary complex is formed, the cysteines are in close proximity to form at least one disulfide bond to trap the polymerase in the closed conformation. Optionally, the finger and the thumb domain of the polymerase are engineered to contain one or more cysteines each, such that in the closed-complex, the cysteines on the opposing fingers interact, forming a disulfide bond and trapping the polymerase in its closed conformation. Introducing cysteines to suitable positions on the polymerase so as to induce disulfide bond formation can be accomplished using methods known to those in the art of protein engineering. A reducing agent such as 2-mercaptoethanol (BME), cysteine-HCl, dithiothreitol (DTT), Tris (2-carboxyethyl) phosphine (TCEP), or any combination thereof may be used to reduce the disulfide bond and release the polymerase. Optionally, nucleotides are added sequentially, one at a time, in separate examination steps along with the cysteine modified polymerase, wherein the need for additional examination reaction conditions that favor ternary complex formation and/or stabilization is optional. Optionally, 1, 2, 3, 4 or more nucleotides (e.g., dATP, dTTP, dCTP, and dGTP) are added in combination in one examination step along with the cysteine modified polymerase, wherein the need for additional examination reaction conditions that favor ternary complex formation and/or stabilization is optional.

Optionally, a cysteine-modified polymerase binds to a template nucleic acid without incorporating a correct nucleotide while forming a ternary complex. While in the ternary complex, the cysteines of the polymerase are close enough in space to form at least one disulfide bond, thereby stabilizing the ternary complex. In this example, the polymerase is trapped and prevented from nucleotide incorporation.

Optionally, a nucleotide present in the examination reaction mixture is a next correct nucleotide, and the cysteine-modified polymerase binds to a template nucleic acid and incorporates the next correct nucleotide forming a ternary complex; wherein while in the closed-complex, the cysteines of the polymerase are close enough in space to form at least one disulfide bond, thereby stabilizing the ternary complex. After ternary complex stabilization and monitoring, an incorporation step can be performed wherein a reducing agent breaks the disulfide bond, releasing the polymerase from the ternary complex. The reducing agent may then be removed, diluted, or sequestered and another examination step may be performed.

Optionally, the nucleotide of the disulfide-stabilized ternary complex is incorporated prior to or during stabilization of the ternary complex. An incorporation step may be performed by reducing the disulfide bond to allow for subsequent nucleotide incorporation and/or an additional examination step.

Optionally, one nucleotide is added to the reaction mixture during the examination step. Optionally, 1, 2, 3, 4 or more nucleotides are added to the reaction mixture during the examination step. Optionally, the next correct nucleotide is enclosed within the ternary complex.

Optionally, a polymerase may form a disulfide bond with itself after formation of a ternary complex. A polymerase can form a disulfide bond to the primed template nucleic acid after formation of a ternary complex. The ternary complex may include a next correct nucleotide based-paired to the next base and/or incorporated to the primer of the primed template nucleic acid.

Optionally, the polymerase is stabilized via cross-linking methods involving the polymerase of the ternary complex. The cross-linking methods do not need to be reversible, as the polymerase can be unbound from the nucleic acid using other means, such as enzymatic or chemical cleavage, denaturation or any combination thereof. Denaturants include, but are not limited to, acids such as acetic acid, or trichloroacetic acid; solvents such as ethanol or methanol; chaotropic agents such as urea, guanidinium chloride, lithium perchlorate; surfactants such as sodium dodecyl sulfate; or any combination thereof. Chemical cleavage includes the use of one or more of natural, modified, or commercially available proteases. Additional methods for releasing a cross-linked polymerase include, but are not limited to, altering pH, temperature, ionic strength, or any combination thereof.

Optionally, a polymerase is modified to favor the formation of a closed-complex over the formation of a binary complex. The polymerase modifications may be genetically engineered. Polymerases may be selected based on their selective binding affinities to the template nucleic acid. A polymerase may be selected or modified to have a high affinity for nucleotides, wherein the polymerase binds to a nucleotide prior to binding to the template nucleic acid. For example, the DNA polymerase X from the African Swine Fever virus has an altered order of substrate binding, where the polymerase first binds to a nucleotide, then binds to the template nucleic acid. Polymerases that bind to nucleotides first may be utilized to develop novel sequencing schemes. Polymerase modifications can be designed to trap the polymerase in a ternary complex in the methods disclosed herein. The polymerase may be trapped permanently or transiently.

Optionally, a modified polymerase that allows for the stabilization of a ternary complex is combined with reaction conditions, usually to release the ternary complex, including, but not limited to, the presence of a release reagent (e.g., catalytic metal ion, such as magnesium or manganese). Optionally, the ternary complex is stabilized even in the presence of a catalytic metal ion. Optionally, the ternary complex is released even in the presence of a cross-linking agent. Optionally, the stabilization of the closed-complex is dependent, in part, on the concentrations and/or identity of the stabilization reagent and/or the release reagents, and any combination thereof. Optionally, the stabilization of a ternary complex using one or more modified polymerases is combined with additional reaction conditions to stabilize a ternary complex, including, but not limited to, sequestering, removing, reducing, omitting, and/or chelating a catalytic metal ion; the presence of a polymerase inhibitor, or non-incorporable nucleotide; and any combination thereof.

Use of Polymerase Inhibitors to Stabilize Ternary Complexes

A ternary complex may be formed and/or stabilized by including a polymerase inhibitor in the examination reaction mixture. Inhibitor molecules phosphonoacetate, (phosphonoacetic acid) and phosphonoformate (phosphonoformic acid, common name Foscarnet), Suramin, Aminoglycosides, INDOPY-1 and Tagetitoxin are non-limiting examples of uncompetitive or noncompetitive inhibitors of polymerase activity. The binding of the inhibitor molecule, near the active site of the enzyme, traps the polymerase in either a pre-translocation or post-translocation step of the nucleotide incorporation cycle, stabilizing the polymerase in its ternary complex conformation before or after the incorporation of a nucleotide, and forcing the polymerase to be bound to the template nucleic acid until the inhibitor molecules are not available in the reaction mixture by removal, dilution or chelation.

Thus, polymerase inhibitor prevents the incorporation of the nucleotide molecule into the primer of the primer template nucleic acid. Optionally, the inhibitor is a non-competitive inhibitor, an allosteric inhibitor, or an uncompetitive allosteric inhibitor. Optionally, the polymerase inhibitor competes with a catalytic ion binding site in the polymerase.

Aminoglycosides non-competitively inhibit polymerase activity by displacing magnesium binding sites in a Klenow polymerase. The non-competitive nature of the interaction with respect to nucleotide binding allows the polymerase to interact with the template nucleic acid and nucleotide, affecting only the catalytic step of nucleotide incorporation.

One inhibitor molecule is the drug Efavirenz, which acts as a non-competitive inhibitor to the HIV-1 reverse transcriptase. The drug has high affinity and a low off-rate for the closed-complex configuration of the polymerase, such that, once the polymerase incorporates the next correct nucleotide, the drug binds to the polymerase, preventing the polymerase from opening its fingers to allow for binding and/or incorporation of a subsequent nucleotide. If the reaction occurs under conditions that favor ternary complex formation over the formation of a binary complex, non-specific polymerase-template nucleic acid interactions can be eliminated, wherein, the binding of the polymerase signifies the added nucleotide is complementary to the next base on the template. If the reaction occurs under examination reaction conditions, the high-affinity binding of the polymerase to the template nucleic acid containing the next correct nucleotide can be used to distinguish the ternary complex from random, non-specific interaction of polymerase with the template nucleic acid. Optionally, high-affinity polymerase binding indicates nucleotide incorporation.

Any polymerase may be chosen and a suitable non-competitive inhibitor may be uncovered using a high-throughput screening (HTS) process. Many examples of HTS processes for polymerase inhibitors are found in the literature, wherein the specific screening criteria is for non-competitive polymerase inhibitors. As a general concept, these inhibitors can be screened to have a binding site that is only exposed when the polymerase is in its closed conformation, and they bind with high affinities and very low off-rates, such that the binding of the inhibitor stabilizes the polymerase in the closed conformation. Such an inhibitor allows incorporation of a single base, after which the binding of the inhibitor prevents the polymerase from opening up to receive another nucleotide. The entire system can be washed away, including the polymerase, before initiating the next step (examination or incorporation) in the sequencing reaction.

Optionally, polymerase inhibitors found to be effective in inhibiting a HIV-1 reverse transcriptase polymerase are employed to stabilize a ternary complex. Optionally, the inhibitor is an inhibitor of HIV-2 reverse transcriptase. HIV-1 reverse transcriptase inhibitors include nucleoside/nucleotide reverse transcriptase inhibitors (NRTI) and non-nucleoside reverse transcriptase inhibitors (NNRTI). NRTIs include, but are not limited to, COMBIVIR (lamivudine and zidovudine; GlaxoSmithKline, Middlesex, UK), EMTRIVA (emtricitabine; Gilead Sciences, Foster City, Calif.), EPIVIR (lamivudine; GlaxoSmithKline, Middlesex, UK), EPZICOM (abacavir sulfate and lamivudine; GlaxoSmithKline, Middlesex, UK), HIVID (zalcitabine; Hoffmann-La Roche, Nutley, N.J.), RETROVIR (zidovudine; GlaxoSmithKline, Middlesex, UK), TRIZIVIR (abacavir sulfate, zidovudine, lamivudine; GlaxoSmithKline, Middlesex, UK), TRUVADA (emtricitabine/tenofovir disoproxil fumarate; Gilead Sciences, Foster City, Calif.), VIDEX EC (enteric coated didanosine; Bristol Myers-Squibb, New York, N.Y.), VIDEX (didanosine; Bristol Myers-Squibb, New York, N.Y.), VIREAD (tenofovir disoproxil fumarate; Gilead Sciences, Foster City, Calif.), ZERIT (stavudine; Bristol Myers-Squibb, New York, N.Y.), and ZIAGEN (abacavir sulfate; GlaxoSmithKline, Middlesex, UK). Examples of NNRTI include, but are not limited to, VIRAMUNE (nevirapine; Boehringer Ingelheim, Rhein, Germany), SUSTIVA (efavirenz, Bristol Myers-Squibb, New York, N.Y.), DELAVIRDINE (Rescriptor; Pfizer, New York, N.Y.), and INTELENCE (etravirine; Tibotec Therapeutics, Eastgate Village, Ireland). Optionally, NNRTIs are non-competitive polymerase inhibitors that bind to an allosteric center located near the RNA polymerase active site on subunit p66.

Optionally, an HIV-1 reverse transcriptase polymerase inhibitor is a (4/6-halogen/MeO/EtO-substituted benzo[d]thiazol-2-yl)thiazolidin-4-one. Table 1 includes a list of 19 (4/6-halogen/MeO/EtO-substituted benzo[d]thiazol-2-yl)thiazolidin-4-ones inhibitors (adapted from E. Pitta et. al., Synthesis and HIV-1 RT inhibitory action of novel (4/6-substituted benzo[d]thiazol-2-yl)thiazolidin-4-ones. Divergence from the non-competitive inhibition mechanism, Journal of Enzyme Inhibition and Medicinal Chemistry, February 2013, Vol. 28, No. 1, Pages 113-122). The (4/6-halogen/MeO/EtO-substituted benzo[d]thiazol-2-yl)thiazolidin-4-ones inhibitors have the following formula:

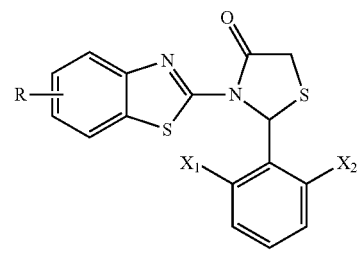

TABLE 1

(4/6-halogen/MeO/EtO-substituted benzo[d]thiazol-2-yl)thiazolidin-4-ones inhibitors

| NNRTI Inhibitor | R | $X_1$ | $X_2$ |
| --- | --- | --- | --- |
| 1 | 4-H, 6-H | F | F |
| 2 | 4-H, 6-H | F | Cl |
| 3 | 4-H, 6-Cl | Cl | Cl |
| 4 | 4-H, 6-Cl | F | Cl |
| 5 | 4-H, 6-Cl | F | F |
| 6 | 4-H, 6-H | Cl | Cl |
| 7 | 4-H, 6-H | F | Cl |
| 8 | 4-H, 6-H | F | F |
| 9 | 4-H, 6-F | Cl | Cl |
| 10 | 4-H, 6-F | F | Cl |
| 11 | 4-H, 6-F | F | F |
| 12 | 4-H, 6-MeO | Cl | Cl |
| 13 | 4-H, 6-MeO | F | Cl |
| 14 | 4-H, 6-MeO | F | F |
| 15 | 4-MeO, 6-H | Cl | Cl |
| 16 | 4-MeO, 6-H | F | Cl |
| 17 | 4-H, 6-EtO | Cl | Cl |
| 18 | 4-H, 6-EtO | F | Cl |
| 19 | 4-H, 6-EtO | F | F |

Any suitable combination of polymerase inhibitors and polymerase mutants may be used order to trap/stabilize the ternary complex and, optionally, prevent multiple nucleotide incorporations per cycle.

The provided reaction mixtures can include from 100 nM to 1 mM of the polymerase inhibitor, or any amount of inhibitor between 100 nM and 1 mM. Optionally, the provided reaction mixtures can include from 1 to 200 µM of the polymerase inhibitor or any amount in between. Optionally, the reaction mixtures include from 30 to 150 µM of the polymerase inhibitor. Optionally, the reaction mixtures include from 30 to 70 µM of the polymerase inhibitor. Optionally, the reaction mixtures include from 60 to 140 µM of the polymerase inhibitor.

Optionally, the polymerase of the ternary complex is prevented from opening its finger domains and translocating to the next template nucleic acid position by using pyrophosphate analogs or other related molecules. Pyrophosphate analogs configure the polymerase in ternary complex by occupying sites close to the triphosphate binding site in the active pocket of the polymerase. Release of the pyrophosphate (PPi) is critical for the polymerase to assume the open conformation, translocate to the next template nucleic acid position, and accept the next nucleotide. The non-competitive inhibitor, such as Foscarnet (phosphonoformate), phosphonoacetate or other pyrophosphate analogs, traps the polymerase in its fingers-closed confirmation. Optionally, binding of the PPi analog is reversible, with the polymerase activity fully restored by washing away, diluting, or sequestering the inhibitor in the reaction mixture. Broadly, any non-competitive inhibitor of polymerase activity may be used during the sequencing reaction.

Optionally, a polymerase inhibitor which stabilizes a ternary complex is combined with reaction conditions which usually release the ternary complex, including, but not limited to, the presence of a catalytic metal ion, such as magnesium or manganese. Optionally, the ternary complex is stabilized even in the presence of a catalytic metal ion. Optionally, the ternary complex is released even in the presence of a polymerase inhibitor. Optionally, the stabilization of the ternary complex is dependent, in part, on the concentrations, the identity of the stabilization reagent, the identity of release reagents, and any combination thereof. Optionally, the stabilization of a ternary complex using polymerase inhibitors is combined with additional reaction conditions which also function to stabilize a ternary complex, including, but not limited to, sequestering, removing, reducing, omitting, and/or chelating a catalytic metal ion; the presence of a modified polymerase in the ternary complex; a non-incorporable nucleotide in the ternary complex; and any combination thereof.

Discriminating Conditions: Distinguishing Binary and Ternary Complex Formation

Since the disclosed technique utilizes polymerase binding without incorporation to identify a cognate nucleotide (i.e., the next correct nucleotide), it can be beneficial to enhance discrimination between specific- and non-specific polymerase binding to the primed template nucleic acid. This can be achieved, in part, by reducing non-specific "background" binding due to binary complex formation.

Binary complex formation conveniently can be reduced, inhibited or destabilized by use of one or more salts that provide monovalent cations. Preferred concentration ranges are from 50 mM to 1,500 mM of a salt that provides monovalent cations (e.g., potassium ions). Preferably, the salt concentration is sufficient to preferentially destabilize binary complexes, and to favor ternary complex formation over binary complex formation by at least two-fold, by at least five-fold, or even more. Still further, the salt that provides monovalent cations may further provide a source of dicarboxylate anions, such as glutamate anions. The concentration of the salt that provides these ions can be from 10 mM to 1.6 M, optionally from 50 mM to 500 mM, or alternatively from 100 mM to 300 mM. Examples of monovalent metal cations include $Na^+$ and $K^+$; while examples of dicarboxylate anions include glutamate anions (e.g., arising from potassium glutamate).

Yet another approach for reducing contributions to polymerase binding signals due to binary complex formation involves the use of modified polymerases. More particularly, a mutant polymerase engineered to have substantially reduced propensity to form binary complexes can also yield good results using the disclosed technique. In some embodiments, formation of a ternary complex that includes a first polymerase and nucleotide (e.g., under high salt conditions to support discrimination) can be followed by use of a second polymerase, such as a "low binary" mutant, and a different nucleotide under lower salt conditions. Advantageously, this shift in salt conditions can enhance or strengthen existing ternary complexes containing the first polymerase, thereby stabilizing those complexes. Using the low binary mutant as the second polymerase permits discrimination between cognate and non-cognate nucleotides, even under the lower salt conditions. This approach can be employed to support the multiple rounds of binding, and optionally washing, that facilitate single-scan imaging. Generally speaking, it is beneficial to reduce binary complex formation when using the multicolored fluorescent sequencing procedure.

Stabilizing Ternary Complexes and Controlling Polymerase Exchange

The ability to form and maintain four different ternary complexes (i.e., produced using four different polymerase-nucleotide combinations in serial fashion) on different features of an array is facilitated by stabilization of ternary complexes. In particular embodiments, it is beneficial to stabilize ternary complexes (e.g., existing or preformed ternary complexes) in the absence of unbound polymerase. This is because the embodiments involve contacting a population of primed template nucleic acid molecules with one polymerase composition at a time, where one or more distinguishable labels associate with the polymerase composition indicate which nucleotide is present in the ternary complex. Any exchange of a polymerase from an established ternary complex with a different labeled polymerase from a subsequent contacting step (e.g., where a polymerase harboring one detectable label is replaced by a different polymerase harboring a different detectable label) would potentially reduce nucleotide-specific polymerase labeling while introducing another polymerase into the ternary complex. Despite this potential, some level of polymerase exchange is required for certain procedures, disclosed herein, that identify cognate nucleotide by "polymerase barcoding."

Optionally, a polymerase is stabilized in its ternary complex by one or a combination of approaches, including for example: crosslinking of polymerase domains (e.g., via biotinylated polymerase to streptavidin); reversible crosslinking of the polymerase to the nucleic acid; use of allosteric inhibition by small molecules, uncompetitive inhibitors, competitive inhibitors, and/or non-competitive inhibitors; use of non-catalytic cations; use of aptamers; use of anti-polymerase antibodies; and denaturation. Optionally, the polymerase inhibitor competes with a catalytic ion binding site in the polymerase. For example, aminoglycosides non-competitively inhibit polymerase activity by displacing magnesium binding sites in a Klenow polymerase. The non-competitive nature of the interaction with respect to nucleotide binding allows the polymerase to interact with the template nucleic acid and nucleotide, affecting only the catalytic step of nucleotide incorporation. In all instances, formation of the stabilized ternary complex provides information about the identity of the next base on the nucleic acid template. Particularly preferred approaches for trapping or stabilizing the polymerase in a ternary complex include the use of non-catalytic cations that inhibit phosphodiester bond formation, such as non-catalytic lanthanide cations, and/or allosteric inhibitors.

Stabilizing ternary complexes that included primed template nucleic acid, polymerase, and cognate nucleotide is illustrated below by the use of particular non-catalytic metal ions. To determine which non-catalytic metal cations afforded the longest retention of ternary complexes during subsequent binding and wash steps, various candidate cations were evaluated. Among the metal ions tested in this procedure were: $Cu^{2+}$, $Mn^{2+}$, $V^{5+}$, $Eu^{3+}$, $Ni^{2+}$, $Sr^{2+}$, $Tb^{3+}$, $Ca^{2+}$ and $Co^{2+}$. Certain preferred reaction conditions substantially maintain ternary complex signals in the absence of non-bound polymerase (i.e., polymerase free in solution, not bound to any immobilized template) over an extended period (e.g., of greater than about 30 seconds, such as about 30-60 seconds). For example, ternary complex binding signal measured at the desired time point following a wash step can be expressed as a percentage of the maximum signal (using the signal measured at the time of initial nucleotide contact as a baseline). In the illustrative examples presented below, these values ranged from about 10-20% (for $V^{5+}$ and $Cu^{2+}$ cation trials) to about 40% and even about 80% (for $Sr^{2+}$ and $Eu^{3+}$ cation trials, respectively). Results obtained using $Tb^{3+}$ cations were substantially similar to trials conducted using $Eu^{3+}$ cations (data not shown). Preferred metal ions include trivalent lanthanide ions, including europium ions and terbium ions. Results confirmed that superior retention of ternary complexes on primed template nucleic acid molecules by these cations were attributable to the physiochemical properties of trivalent lanthanides.

At concentrations of $Eu^{3+}$ or $Tb^{3+}$ greater than about 5 mM, the tested polymerases exhibited reduced abilities to discriminate between correct and incorrect nucleotides in the presence of moderate concentrations (e.g., 150 mM to 300 mM) of monovalent metal cations. Stated differently, the difference in observed signals between correctly matched dNTPs and that observed for binary complexes was reduced. This was not the case when using non-catalytic divalent metal cations (e.g., $Ni^{2+}$ or $Sr^{2+}$). Interestingly, although $V^{5+}$ by itself did not provide the conditions necessary to allow the desired level of discrimination while stabilizing ternary complexes against polymerase exchange, the combination of $V^{5+}$ and a trivalent lanthanide ion at a concentration greater than about 5 mM advantageously provided good results. More particularly, concentrations of $Eu^{3+}$ or $Tb^{3+}$ that were high enough to compromise discrimination between binary and ternary complexes could be used when $V^{5+}$ ions also were included (e.g., in the range of from 1 mM-100 mM, with 12.5 mM being preferred) in the binding solution. This was another way that ternary complexes could be stabilized at the same time binary complexes were destabilized.

Illustrative Workflow in a Multi-Label Sequencing Protocol

FIG. 1 illustrates a sample workflow in which a plurality of cycles of binding and washing progressively build-up ternary complexes on the primed template nucleic acid molecules of a population. After an imaging step is performed at the conclusion of the build-up procedure, ternary complexes are stripped from the primed template nucleic acid molecules, and another polymerase enzyme (i.e., different from the polymerase of the imaged ternary complex) incorporates a nucleotide (e.g., an unlabeled reversible terminator nucleotide). Ternary complexes formed during the build-up procedure include a cognate nucleotide and a polymerase, where the nucleotide and polymerase contacted the primed template nucleic acid in combination with each other. Each ternary complex—and so the nucleotide contained within—is "encoded" by any distinguishable feature of the polymerase, such as a detectable label linked to the polymerase, and the coincident time at which the polymerase and nucleotide contacted the primed template nucleic acid molecule. A ternary complex-stabilizing agent is included in each of the binding and washing steps. Optionally, the presence of nucleotides from all previous binding steps contributes to maintenance of ternary complexes. Optional wash steps intervening between the serial contacting steps remove non-bound polymerase from the previous binding step.

Typically, there will be a field or population of separated primed template nucleic acid molecules, where individuals among the population may be different from each other. The complexity of analysis for population systems involving thousands or even millions of sequencing targets precludes manual processing and analysis. Instead, population sequencing generally involves the use of robotic or automated systems.

The provided method easily adapts to automated platforms where repetitive steps are performed. Binding of a first polymerase composition (e.g., possibly including only a single distinguishably labeled polymerase) to a primed template nucleic acid molecule in the presence of one of four dNTPs (e.g., dATP, dCTP, dGTP, and either dTTP or dUTP) is typically performed for a period of anywhere from 10 seconds up to five minutes (e.g., usually about 60 seconds). The binding step is optionally followed by a brief wash (e.g., of from 10-30 seconds) using the same buffer that was employed in the binding step, but omitting the first polymerase, and optionally reducing the concentration of the dNTP down to a level of about 10% of the concentration used in the binding step. When this is the case, the ternary complex remains substantially intact over a period of time sufficient to interrogate all of the different dNTPs. In accordance with contemplated alternatives, however, the wash step can be performed in the presence or absence of dNTP(s), and may be performed in the presence of the same non-catalytic metal cation, a different non-catalytic metal cation, or a combination of non-catalytic metal cations. The first wash removes from the system any unbound first polymerase before a second nucleotide enters the system.

In particular embodiments, the simultaneous presence of (1) unbound labeled polymerase from a previous contacting step, and (2) a nucleotide from a subsequent step (i.e., that delivered a different polymerase-nucleotide combination) will promote formation of a ternary complex that includes an undesired polymerase-nucleotide combination. A limited amount of polymerase carryover can be acceptable, and will not affect base calling. However, excessive carry over could lead to mis-identification of the subsequently delivered nucleotide as the nucleotide from the previous step, and an erroneous base call. This is different from the "exchange labeling" that underlies "polymerase barcoding."

In polymerase barcoding, it is the presence of a polymerase from a subsequent step (as opposed to a previous step) that participates in formation of a ternary complex. Here a "barcode" of polymerases in a ternary complex can be represented by the collection of distinguishably labeled polymerases that included the first and all subsequent polymerases that were present when the cognate nucleotide also was present. Of course, this applies to procedures wherein a nucleotide is present in washes and/or subsequent rounds of the serially contacting steps. This provides the opportunity for associating an earlier nucleotide with a later-added polymerase from a different polymerase-nucleotide combination. Again, "barcoding" is made possible by polymerase exchange out of a pre-existing ternary complex.

Optionally, the binding and washing conditions employed in the present technique can substantially maintain the integrity of the ternary complex. Typically, the first polymerase used in connection with the first nucleotide will harbor a first detectable label (e.g., a first fluorescent label) that distinguishes the first polymerase-nucleotide combination from other polymerase-nucleotide combinations used in the procedure. Ternary complexes conveniently can be maintained after formation by including the cognate nucleotide and the ternary complex-stabilizing agent (e.g., a non-catalytic metal ion, such as a trivalent lanthanide cation) in all subsequent binding and washing buffers. In particular embodiments, ternary complexes, once formed and maintained, should not substantially dissociate or exchange polymerases. Optionally, ternary complexes formed after the first polymerase binding step can be visualized by detecting the label associated with the first polymerase before the last polymerase binding step (e.g., the fourth polymerase binding step). In certain preferred embodiments, a single imaging step detects all ternary complexes at the conclusion of the last of four polymerase-nucleotide binding steps (i.e., so-called "single-scan imaging"). This allows all cognate nucleotides to be identified from the results of a single imaging step conducted at the conclusion of all polymerase-nucleotide binding steps.

A second polymerase binding step can involve a second polymerase, distinguishable from the first polymerase (e.g., by the presence of a different detectable label), that is contacted with the primed template nucleic acid molecules of the population in the presence of a second nucleotide. Again, the buffer used in the second polymerase binding step optionally can include all components of the prior binding buffers with the exception of the polymerase(s) (or the polymerase label) from the prior steps. The binding buffer used in the second polymerase binding step can include the second polymerase (among other components), but will not include the first polymerase (or the polymerase label) from the first polymerase binding step. After allowing formation of ternary complexes containing a primed template nucleic acid, the second polymerase, and the second nucleotide, the population is washed with a wash buffer that includes the salts and ternary complex-stabilizing agent of the first binding buffer, the nucleotides from the first and second binding buffers, but no polymerase. The second wash removes from the system any unbound second polymerase before a third nucleotide enters the system. Consistent with the description above, it is to be understood that the simultaneous presence of unbound second polymerase (i.e., free in solution) with a third nucleotide conceivably could lead to formation of a ternary complex that would misidentify the second nucleotide as the cognate nucleotide when the next correct nucleotide is actually the third nucleotide. This is because identity of the cognate nucleotide is based on the identity of the polymerase (e.g., determined by the label on the polymerase) participating in a ternary complex. This may be the polymerase that was delivered with the nucleotide in the polymerase-nucleotide combination, but also may include the distinguishably labeled polymerases from subsequent polymerase-nucleotide combinations.

Steps in the workflow can be repeated for binding of a third distinguishable polymerase in combination with a third nucleotide, and for binding of a fourth distinguishable polymerase in combination with a fourth nucleotide. Wash steps after each round of polymerase-nucleotide contacting steps ensure removal of the polymerase from the prior step before introduction of the new nucleotide. Each wash buffer includes the salts and ternary complex-stabilizing agent of the prior binding buffer, and optionally the nucleotides from all of the prior binding buffers, but includes no polymerase. At the conclusion of the binding and washing steps, individual primed template nucleic acid molecules of the population will have contacted each of four different types of nucleotide in combination with a polymerase capable of forming ternary complexes. An imaging step identifies which polymerase is present in a ternary complex that includes cognate nucleotide and primed template nucleic acid molecule.

After the imaging step, any reversible terminator moiety present on the 3'-nucleotide of the primer can be removed so that the primer of the primed template nucleic acid can participate in phosphodiester bond formation. A second polymerase can then be introduced in the presence of four unlabeled reversibly terminated dNTPs for the incorporation of the correct reversibly terminated nucleotide at each feature. The incorporation step optionally may be followed by a step for de-blocking the reversibly terminated extended primer (i.e., removing the reversible terminator moiety). Alternatively, subsequent examination step(s) may be performed prior to de-blocking.

Robustness of the disclosed sequencing platform was supported by assay chemistry that: (1) enhanced discrimination between formation of binary and ternary complexes, where binary complex formation was reduced or inhibited or destabilized—ideally to the point of being undetectable; and (2) stabilized ternary complexes without nucleotide incorporation, so that exchange of bound polymerase with polymerase from the bulk reaction mixture (e.g., a polymerase harboring a different detectable label) was controlled or minimized. Since retention of ternary complexes during the cycling of polymerase-nucleotide binding and washing need not be absolute (some ternary complex dissociation is acceptable), the use of a second polymerase to incorporate reversible terminator nucleotides (e.g., unlabeled reversible terminator nucleotides) works to minimize "phasing" in the sequence data. Those having an ordinary level of skill in the art will appreciate that phasing results when a population of primed template molecules is being subjected to primer extension conditions in parallel but a subset of the extension products have fallen out of synch with the rest of the population. Thus, when the bulk of the population is being extended at position N of the primed template, the subset is being extended at positions N−1, N−2, or N−3 etc. of the primed template.

Systems

The disclosed technique for determining cognate nucleotides, whether for a single nucleic acid feature or for a population of different nucleic acid features spaced apart in a flow cell or well of a multiwell plate, can be performed using a dedicated system of interrelated modules or components. Some useful systems will be familiar to those having an ordinary level of skill in the art, and can be adapted or configured for processing by the disclosed technique that relies on identification or tracking of distinguishably labeled polymerases (e.g., four polymerases). An exemplary system for use in identifying a next correct nucleotide of a primed template nucleic acid molecule typically will include: a reaction vessel; a reagent dispense module; an imaging module; a processing module; and an electronic storage device. Systems useful for single-scan imaging of a population of nucleic acid features will have the capability of detecting four different fluorescent emission wavelengths. Essential features of particularly preferred systems are described below.

The reaction vessel employed in the system may take different forms. The reaction vessel will be in fluid communication with a supply of two or more distinguishably labeled polymerases. Examples of reaction vessels include flow cells having inlet and outlet ports, and one or more wells of a multiwell plate. Contained within the reaction vessel will be a collection or population of nucleic acid features to be processed by the disclosed technique. The nucleic acid features may be "clusters" of spaced-apart amplified nucleic acids (e.g., in situ amplified nucleic acids). Alternatively, individual beads harboring homogenous populations of nucleic acids may be contained within the reaction vessels.

The reagent dispense module also may take different forms. The reagent dispense module directs into the reaction vessel, one at a time, a liquid reagent that includes one of four distinguishably labeled polymerases in combination with one or more different nucleotides for each of four reagent exchanges. Optionally, the distinguishably labeled polymerases harbor different fluorescent detectable labels. Optionally, none of the fluorescent detectable labels is an intercalating dye, and wherein none of the fluorescent detectable labels is excited by energy transfer from a different molecular species. Optionally, the reaction vessel is a flow cell, and each reagent exchange involves flowing through the flow cell a second liquid reagent to replace a first liquid reagent. Optionally, the reagent dispense module includes a syringe pump that controllably transfers one of the four distinguishably labeled polymerases in combination with one or more of four different nucleotides. Optionally, the liquid reagent directed into the reaction vessel by the reagent dispense module includes a ternary complex-stabilizing agent. Exemplary ternary complex-stabilizing agents are disclosed elsewhere, herein. Preferably, none of the fluorescent detectable labels of the polymerases delivered by the reagent dispense module is an intercalating dye, and none of the fluorescent detectable labels is excited by energy transfer from a different molecular species.

The imaging module also may take different forms. The imaging module will be capable of detecting which of several distinguishably labeled polymerases is present in a complex that includes: (i) the primed template nucleic acid molecule; (ii) one of the distinguishably labeled polymerases; and (iii) the next correct nucleotide. Optionally, the imaging module includes an illumination component and a detection component. Illumination components may take the form of light emitting diodes (LEDs) that generate a range of wavelengths. A plurality of different LEDs may be employed in the imaging module. Useful detectors include fluorometers that measure parameters of fluorescence. There also can be one or more optical filters for narrowing the range or band of wavelengths that are transmitted either from an illumination component to a sample, or from the sample to a detector. The detection component of the imaging module optionally can be configured to detect intensities of a plurality of different wavelengths, each corresponding to a fluorescence emission by one of the four distinguishably labeled polymerases. Thus, each of the fluorescent detectable labels associated with one of the polymerases can be excited by a wavelength of energy produced by the illumination component (e.g., produced by one of the LEDs), and an emission signal produced by the detectable label can be detected by the detection component. In one embodiment, the imaging module includes an illumination component and a detection component, where each of several distinguishably labeled polymerases is labeled with a fluorescent detectable label, where each of the fluorescent detectable labels is excited by a wavelength of energy produced by the illumination component, and where the detection component is configured to detect intensities of a plurality of different wavelengths, each corresponding to a fluorescence emission by one of the several distinguishably labeled polymerases.

The processing module also can take different forms. For example, the processing module can include a computer (e.g., either a standalone computer or processor, a computer or processor integrated into the system within a common housing or chassis) configured with software to compare intensities of the plurality of different wavelengths, and to determine therefrom the identity of the next correct nucleotide. The processing module will be configured to receive a result from the imaging module, and further configured to identify the next correct nucleotide using the result processed result. Configuring of the processing module may involve embedded, or otherwise accessible software instructions (e.g., being accessed from a remote software repository).

The electronic storage device also can take different forms. The storage device will be in communication with the processing module, and stores a non-transient record of the next correct nucleotide identified by the processing module. For example, the electronic storage device can be a computer hard drive, flash drive, floppy disk, compact disk (CD) or other optical disk storage medium, cloud storage arrangement, and the like.

Optionally, the system can also include an output device that produces a non-transient record of the next correct nucleotide identified by the processing module. The non-transient record produced by the output device optionally can be either a record stored on computer-readable media, or a record printed on paper.

EXAMPLES

The following Examples illustrate aspects of the disclosed technique related to ternary complex stabilization, enhanced discrimination between ternary and binary complex formation, and application to sequence determination using an optional single-step imaging approach.

Example 1 illustrates procedures that can be used for identifying agents that stabilize ternary complexes against dissociation and polymerase exchange. Non-catalytic metal cations were used as illustrative stabilizing agents. However, polymerase inhibitors, aptamers, and anti-polymerase antibodies also may be used for this purpose.

Example 1

Stabilizing Ternary Complexes Against Polymerase Exchange

A FORTEBIO® (Menlo Park, Calif.) Octet instrument employing biolayer interferometry to measure binding reactions at the surface of a fiber optic tip was used in a multiwell plate format to assess formation and stability of ternary complexes in the presence of different non-catalytic metal ions. Template nucleic acid strands biotinylated at their 5'-ends were used to immobilize the primed template nucleic acid onto fiber optic tips functionalized with streptavidin (SA) according to standard procedures. Tips were washed in a Tris-buffered solution containing 200 mM KCl, 160 mM potassium glutamate, and 0.01% Tween-20 before commencing the cycling protocol. Binding reactions conducted using 2 mM of the test metal ion (i.e., 2 mM of the metal salt) were carried out in serial fashion using examination buffers that contained Tris-HCl (pH 8.0), 220 mM KCl, 160 mM potassium glutamate, 0.01% Tween-20, 1 mM β-mercaptoethanol, 100 µg/ml BSA, the correct nucleotide at a concentration of 100 µM, and 200 nM unlabeled Bst DNA polymerase large fragment. Salts used in the testing procedure included: $SrCl_2$, $Na_3VO_4$, $EuCl_3$, and $CuSO_4$. Examination buffers in this procedure were supplemented with DMSO and betaine to control DNA secondary structure. Binding steps were carried out for 60 seconds, and were followed by wash steps using a buffer that omitted polymerase, but included 10 µM of the correct dNTP, 100 µM of the incorrect dNTP, and 2 mM of the test metal ion. Retention of the ternary complex was measured over the course of 300 seconds. Surviving ternary complexes were stripped from the primed template by exposure to a solution containing 30 mM Tris-HCl (pH 8.0), 1 M NaCl, 4 mM EDTA, 4 mM DTPA, 0.2% SDS, 0.05% Tween-20, and 3% Tween-80 for a period of 30 seconds. This was followed by exposure to a regeneration solution made Tris-HCl (pH 8.0), 220 mM KCl, 160 mM potassium glutamate, 0.01% Tween-20, 1 mM β-mercaptoethanol, 100 µg/ml BSA for 20 seconds before commencing binding of polymerase and cognate nucleotide in the presence of the next test metal ion.

Figure 2:
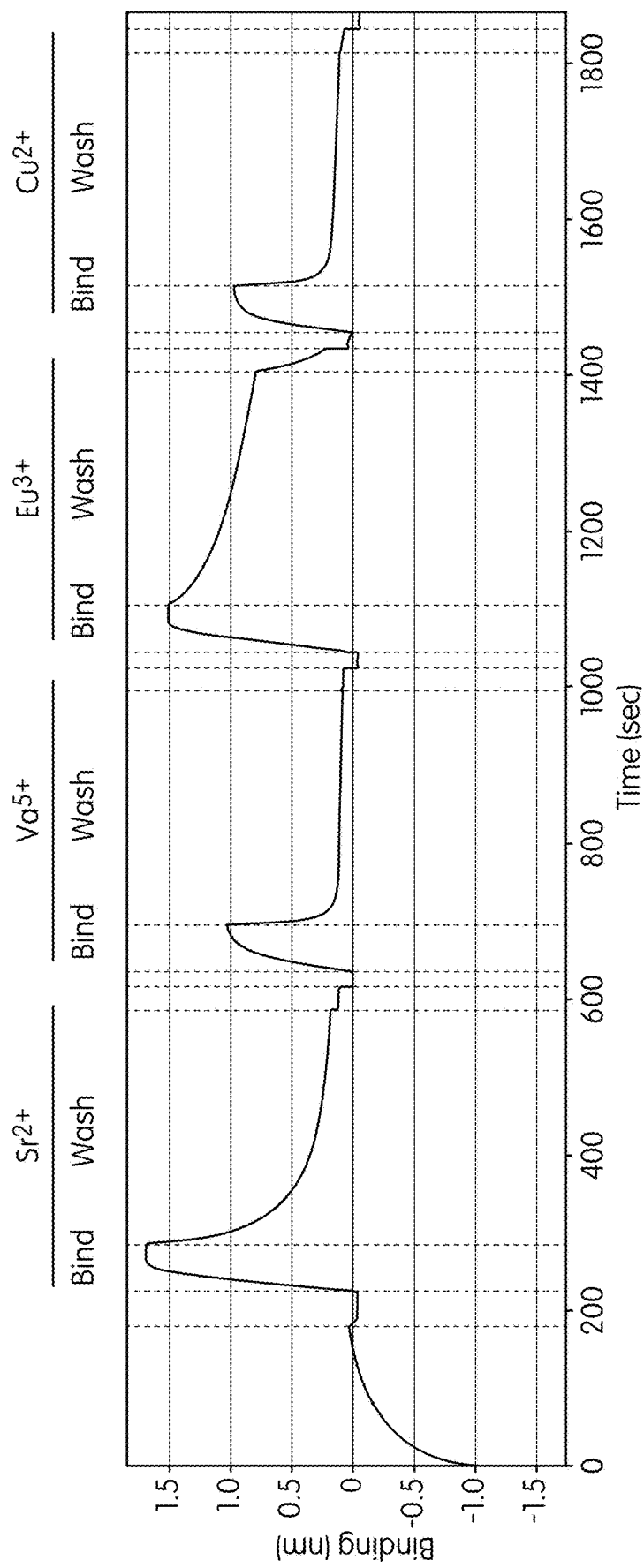
FIG. 2 is a graphical trace showing binding signal (vertical axis) as a function of time (horizontal axis) for polymerase binding and retention in the presence of different non-catalytic metal cations ($Sr^{2+}$, $V^{5+}$, $Eu^{3+}$, and $Cu^{2+}$).

The results presented in FIG. 2 demonstrated how different non-catalytic metal cations were associated with different formation and decay profiles for a ternary complex. Both $V^{5+}$ and $Cu^{2+}$ ions gave moderately high binding signals when ternary complexes formed on primed template nucleic acid molecules. However, rapid decay was observed following washing that involved removal of polymerase, reduction of correct nucleotide concentration down to 10% of the level used for binding, and addition of an incorrect nucleotide (e.g., corresponding to a concentration 10 fold higher than the level of the correct nucleotide). Both $Sr^{2+}$ and $Eu^{3+}$ ions gave high binding signals when ternary complexes formed on primed template nucleic acid molecules. Whereas ternary complex decay rates were slower than observed with $V^{5+}$ and $Cu^{2+}$ ions under corresponding conditions, the ternary complex formed and maintained in the presence of $Eu^{3+}$ was substantially more stable. More particularly, ternary complexes that were formed in the presence of $Eu^{3+}$ ions, and then washed in the presence of $Eu^{3+}$ ions and reduced levels of correct nucleotide and increased levels of an incorrect nucleotide, persisted for a longer duration. Although not shown in FIG. 2, use of $Tb^{3+}$ ions gave results substantially similar to the use of $Eu^{3+}$ ions. The $Eu^{3+}$ non-catalytic metal ion was selected as an exemplary stabilizing agent to demonstrate the sequencing procedure in a population context.

Example 2 describes procedures to optimize discrimination between correct and incorrect nucleotides by a polymerase in the absence of chemical incorporation of any nucleotide into the primer of a primed template nucleic acid molecule. The procedure involved titration of salts that dissolved in aqueous solution to provide monovalent cations. All trials included a fixed concentration of an agent that stabilized ternary complexes (e.g., $Eu^{3+}$ non-catalytic metal cation), and concentrations of potassium glutamate were held constant at 80 mM, 160 mM, 320 mM, or 640 mM. Each of these four conditions was then used for titrating a salt that provided monovalent metal cations in the presence of a correct (i.e., cognate) or an incorrect (i.e., non-cognate) nucleotide to determine the effect. The procedure focused on enhancement of nucleotide discrimination under conditions that preferentially destabilized binary complex formation.

Example 2

Enhancing Polymerase Discrimination Between Cognate and Non-Cognate Nucleotides in the Presence of an Agent that Stabilized Ternary Complexes Materials and methods used in the procedure were as follows. The FORTEBIO® OCTET® instrument employing biolayer interferometry was used to measure binding reactions at the surface of a fiber optic tip in a multiwell plate format to investigate differential formation of binary and ternary complexes. Template strands biotinylated at their 5'-ends were used to immobilize the primed template nucleic acid onto fiber optic tips functionalized with streptavidin (SA) according to standard procedures. The next correct nucleotide for the biotinylated template DNA was dCTP (with dGTP being used as the model incorrect nucleotide). Tips were first equilibrated in a Tris-buffered solution containing 30 mM Tris-HCl (pH 8.0), and 0.1 mM EDTA before commencing the cycling protocol. Independent binding reactions for the two test nucleotides (i.e., cognate and non-cognate nucleotides) were carried out in the presence of concentrations of KCl that varied from 100 mM to 650 mM when the concentration of dipotassium glutamate was fixed at either 80 mM, 160 mM, 320 mM, or 640 mM. In all instances the europium salt concentration was held constant at 2 mM (i.e., $Eu^{3+}$ concentration was 2 mM). Also in all instances, the reaction mixture used during the examination step contained Tris-HCl (pH 8.0), 0.01% Tween-20, 100 µg/ml BSA, 2 mM $Eu^{3+}$ cations derived from the chloride salt, 350 U/ml Bsu DNA polymerase large fragment; and one of the nucleotides at a concentration of 100 µM (dCTP was used as a cognate nucleotide, and dGTP was used as a non-cognate nucleotide). Following each examination step, tips were exposed to a buffer containing 60 mM Tris-HCl (pH 8.0), 1 M NaCl, 4 mM EDTA, 0.02% SDS and 0.1% Tween-20 for 30-60 seconds to strip enzyme complexes from the primed template nucleic acid. Optionally, the buffer that strips enzyme complexes may further include a chemical agent that cleaves any reversible terminator moiety attached to the 3' nucleotide of the primer strand of the primed template nucleic acid molecule. The stripping step was followed by a 15 second exposure to examination buffer without enzyme, dNTP or divalent cations to regenerate tips for the next cycle of examination. When using a single contacting step to effect binding of polymerase and nucleotide to the primed template nucleic acid, the binding step was 60 seconds long, with binding interactions being monitored continuously. This was accomplished by contacting the primed template nucleic acid with a single solution that included the polymerase, the test nucleotide, and appropriate salts. Results from interferometry monitoring were analyzed to identify formation of ternary complexes (i.e., identifying cognate nucleotide) or binary complexes (i.e., identifying non-cognate nucleotide).

The results from these procedures generally showed that use of either $Eu^{3+}$ (see FIGS. 3A, 3B, 3C and 3D) or $Tb^{3+}$ (see FIGS. 4A, 4B, 4C, and 4D) as stabilizing agents led to discrimination profiles that had not been observed before. More particularly, whereas non-cognate nucleotide binding was preferentially destabilized until plateauing as the concentration of added monovalent metal ion increased, cognate nucleotide binding also plateaued—but at a higher level.

Stated differently, the results illustrated maintenance of the fold discrimination favoring ternary complex formation over binary complex formation, rather than clear biphasic decreases, as the concentration of monovalent metal ion from all sources (e.g., KCl and potassium glutamate) increased. This demonstrated that discriminatory conditions could be identified that facilitated ternary complex formation, while minimizing binary complex formation and precluding nucleotide incorporation.

Figure 3A:
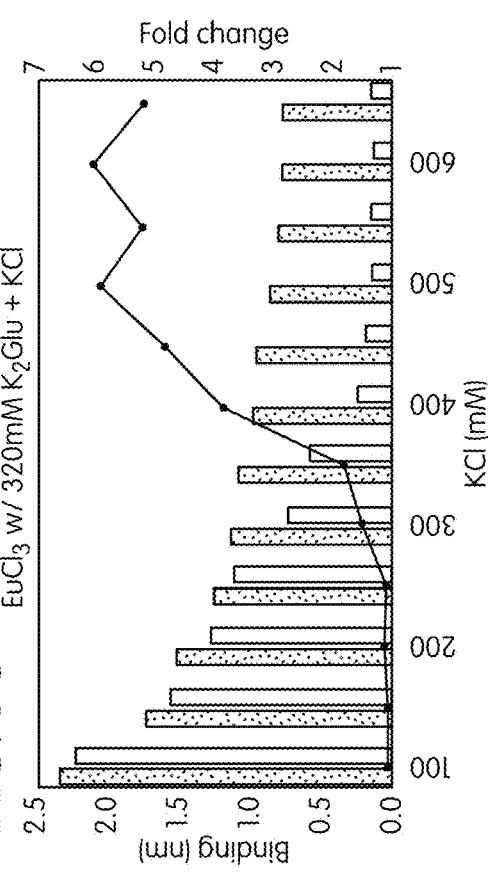
FIGS. 3A, 3B, 3C and 3D are a series of composite graphs showing polymerase binding intensity (left axis) in the presence of cognate (filled bars) and non-cognate (open bars) nucleotides when $Eu^{3+}$ was the agent stabilizing ternary complexes. The plotted line with markers indicates the fold discrimination (right axis) for ternary complex formation relative to binary complex formation. Potassium glutamate is indicated by "$K_2Glu$."
Figure 3B:
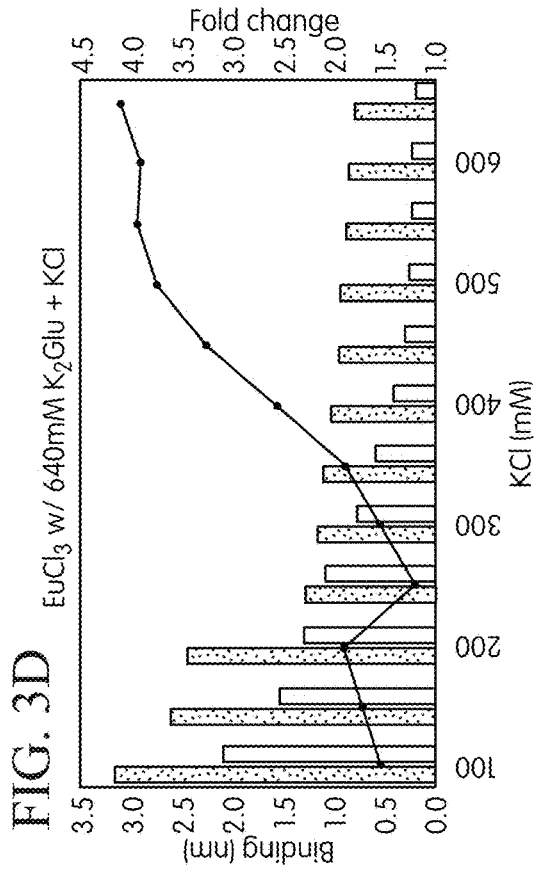
Figure 3C:
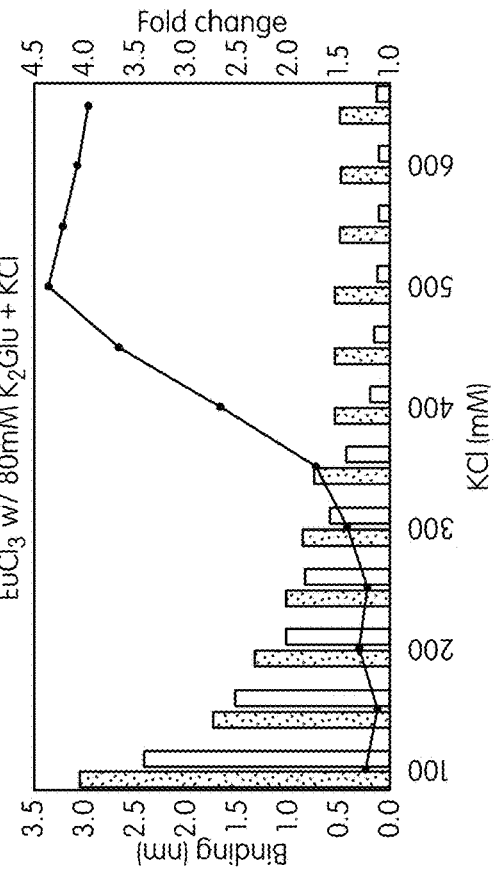
Figure 3D:
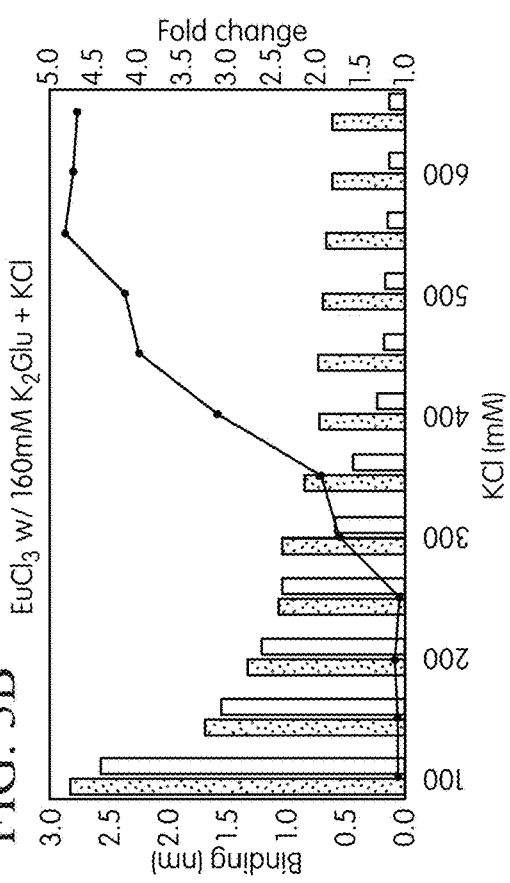

Results from trials conducted using $Eu^{3+}$ as the stabilizing agent confirmed that good discrimination between ternary and binary complex formation was achievable. FIG. 3A shows results from the KCl titration of trials made 2 mM $Eu^{3+}$ and 80 mM potassium glutamate, indicating maximal fold discrimination was observed when the added KCl concentration was about 500 mM. However, very good results were obtained when the added KCl concentration was greater than 350 mM (e.g., in the range of from 350 mM to 650 mM). FIG. 3B shows results from the KCl titration of trials made 2 mM $Eu^{3+}$ and 160 mM potassium glutamate, indicating the fold discrimination plateaued when the added KCl concentration was about 550 mM. However, very good results were obtained when the added KCl concentration was greater than 300 mM (e.g., in the range of from 300 mM to 650 mM). FIG. 3C shows results from the KCl titration of trials made 2 mM $Eu^{3+}$ and 320 mM potassium glutamate, indicating the fold discrimination substantially plateaued when the added KCl concentration was about 500 mM. However, very good results were obtained when the added KCl concentration was greater than 300 mM (e.g., in the range of from 300 mM to 650 mM). Finally, FIG. 3D shows results from the KCl titration of trials made 2 mM $Eu^{3+}$ and 640 mM potassium glutamate, indicating the fold discrimination plateaued when the added KCl concentration was about 500 mM. However, very good results were obtained when the added KCl concentration was greater than 300 mM (e.g., in the range of from 300 mM to 650 mM).

Figure 4A:
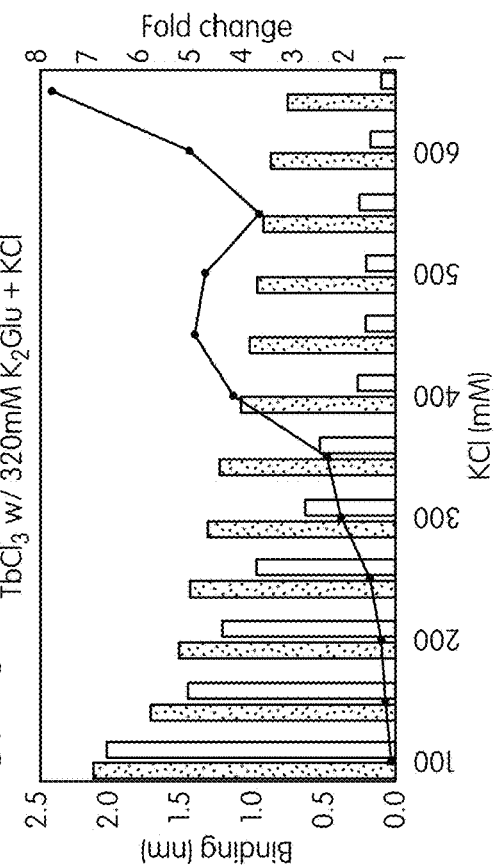
FIGS. 4A, 4B, 4C, and 4D are a series of composite graphs showing polymerase binding intensity (left axis) in the presence of cognate (filled bars) and non-cognate (open bars) nucleotides when $Tb^{3+}$ was the agent stabilizing ternary complexes. The plotted line with markers indicates the fold discrimination (right axis) for ternary complex formation relative to binary complex formation. Potassium glutamate is indicated by "$K_2Glu$."
Figure 4B:
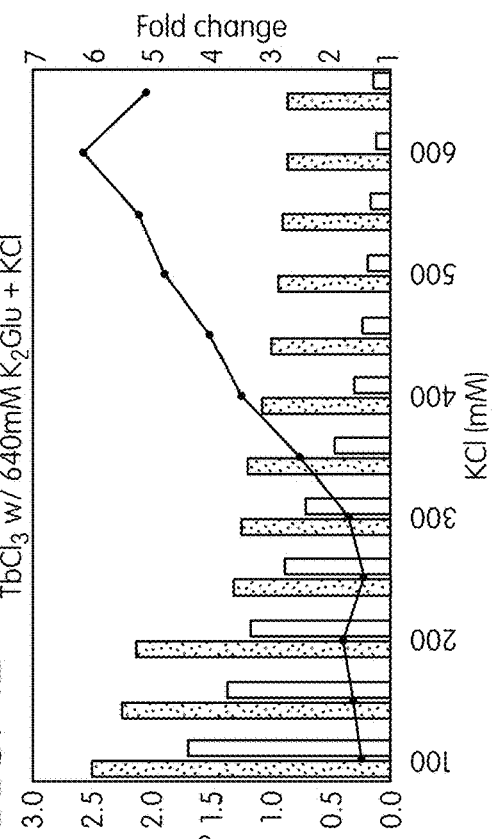
Figure 4C:
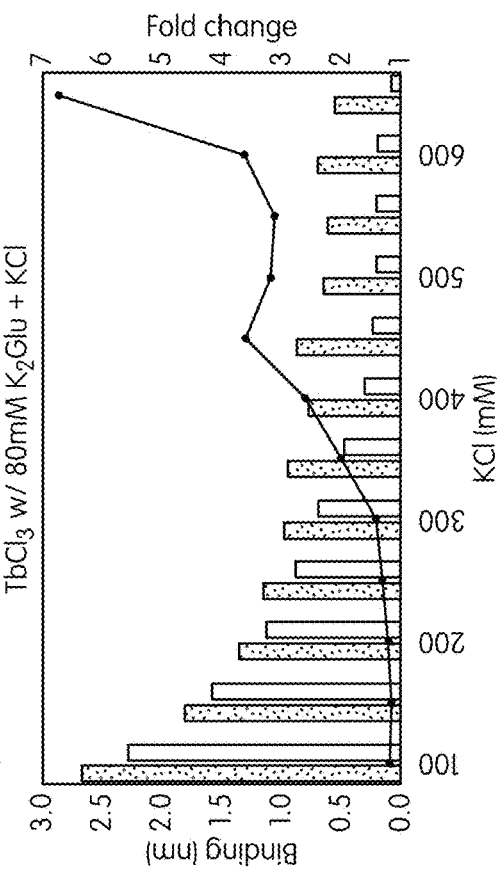
Figure 4D:
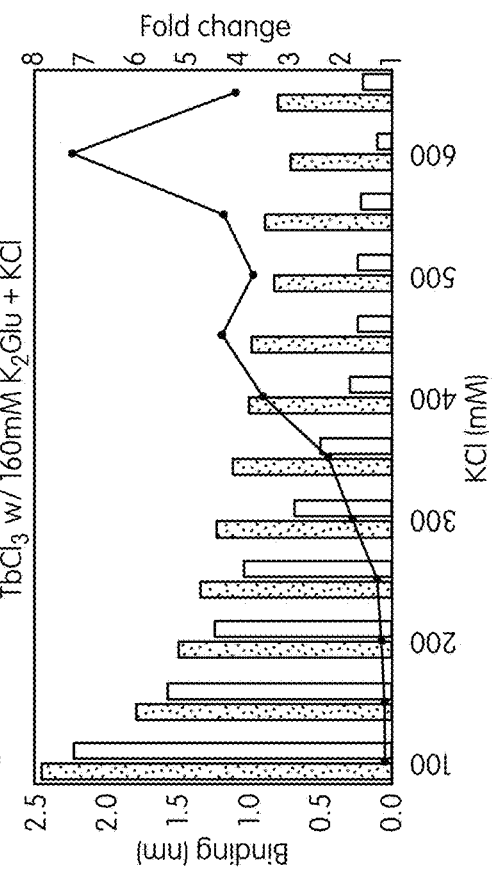

Results from trials conducted using $Tb^{3+}$ as the stabilizing agent also confirmed good discrimination between ternary and binary complex formation was achievable. FIG. 4A shows results from the KCl titration of trials made 2 mM $Tb^{3+}$ and 80 mM potassium glutamate, indicating increased fold discrimination was observed when the added KCl concentration was about 350 mM or greater (e.g., in the range of from 350 mM to 650 mM). FIG. 4B shows results from the KCl titration of trials made 2 mM $Tb^{3+}$ and 160 mM potassium glutamate, indicating increased fold discrimination when the added KCl concentration was 300 mM or greater (e.g., in the range of from 300 mM to 650 mM). FIG. 4C shows results from the KCl titration of trials made 2 mM $Tb^{3+}$ and 320 mM potassium glutamate, indicating increased fold discrimination when the added KCl concentration was about 300 mM or greater (e.g., in the range of from 300 mM to 650 mM). FIG. 4D shows results from the KCl titration of trials made 2 mM $Tb^{3+}$ and 640 mM potassium glutamate, indicating increased fold discrimination was obtained when the added KCl concentration was about 350 mM or greater (e.g., in the range of from 350 mM to 650 mM).

Taken together, these results confirmed that routine experimentation could be used to identify useful discriminating conditions that stabilized ternary complexes. As demonstrated, even salts providing monovalent metal cations (e.g., KCl, potassium glutamate, etc.) could be used to manipulate the relative formation of ternary and binary complexes. The effect was primarily achieved by preferentially destabilizing binary complexes using salts providing monovalent metal cations. Importantly, in the presence of an agent that stabilized ternary complexes (illustrated above using a trivalent lanthanide cation), appeared to stabilize ternary complexes even when binary complexes were destabilized at higher concentrations of the salt that provided monovalent metal cations.

Nucleic acid sequencing was facilitated by conditions that permitted discrimination between binary and ternary complex formation, while stabilizing ternary complexes against exchange or substitution by another polymerase from the bulk solution. By this approach, subsequent rounds of binding and examination using different combinations of polymerase and nucleotide could be conducted while retaining the initial ternary complex and any detectable signal that identified the cognate nucleotide.

The following Example illustrated a method and system that can be used for high-throughput sequencing. Each of two different types of nucleotide (e.g., dATP and dCTP) was encoded by its association with a distinguishable polymerase. The different polymerases were distinguished from each other by the presence or absence of different detectable labels. In this instance the different fluorescent labels were Cy3 and Cy5. Primed target nucleic acid molecules immobilized to beads in a flow cell were first contacted with the combination of a first nucleotide (e.g., dCTP) and a Cy3-labeled first polymerase in the presence of a ternary complex-stabilizing agent (e.g., an $Eu^{3+}$ non-catalytic metal cation). A second nucleotide (e.g., dATP) together with a Cy5-labeled second polymerase contacted the primed template nucleic acid molecules following a wash step that included the nucleotide from the first contacting step, but not the labeled polymerase. In this way, the two polymerase-nucleotide combinations did not mingle. Generally speaking, when the ternary complex-stabilizing agent is a non-catalytic metal cation, the non-catalytic metal cation can be a trivalent metal cation. Optionally, the trivalent metal cation is a lanthanide, such as europium or terbium ion. When the nucleotide is the next correct nucleotide, a stable ternary complex is formed that survives washes with buffer solutions containing the cognate dNTP but not the polymerase associated with that cognate dNTP. Subsequent binding and wash cycles can be conducted as a result of this stability. At the conclusion of the binding cycles, optionally including a subsequent wash cycle, a single imaging cycle can be used for rapid detection of bound polymerases and identification of cognate nucleotides. Cognate nucleotides are identified by the distinctive label (or absence of label) on the polymerase when the free polymerase and nucleotide were delivered to the primed template nucleic acid in combination. Incorporation of reversible terminator nucleotides (e.g., unlabeled reversible terminator nucleotides) allows the primer to increment forward by a single base. This may occur following removal of the labeled polymerase(s). Optionally, a polymerase different from any polymerase used in combination with free nucleotide is used for incorporating reversible terminator nucleotides. Optionally, the reversible terminator moiety of the incorporated reversible terminator can be removed before the next cycle of examination begins.

Example 3 illustrates a bead-based sequencing protocol, where a plurality of cycles of binding different polymerase-nucleotide combinations to a primed template nucleic acid molecule, followed by washing under conditions that maintained integrity of the ternary complexes, were used to identify ternary complexes and the next correct nucleotide. The procedure was carried out using microbeads immobilized within a flow cell, where the microbeads displayed a homogenous population of primed template nucleic acid molecules. It will be apparent that the binding and examination step in the procedure does not change the primer (i.e., there is neither incorporation into, nor degradation of the primer).

Example 3

Rapid Identification of Cognate Nucleotide

Flow cells were prepared using magnetic 1 µM microbeads displaying synthetic primed template nucleic acids of known sequence. Briefly, streptavidin-coated MyOne C1 magnetic beads (ThermoFisher Scientific; Waltham, Mass.) were functionalized with a TCO-PEG4-NHS (transcyclooctene-polyethylene glycol-N-hydroxysuccinimide) moiety that reacts with free amine moieties on the streptavidin. The TCO-modified beads were then incubated in a solution containing the desired primed template nucleic acid molecule at a concentration of 100 nM. Here two different primed template nucleic acids were employed on different beads. The next correct nucleotide for the primed template disposed on one bead type (the "C2" bead) was dCTP. The next correct nucleotide for the primed template disposed on the other bead type (the "A2" bead) was dATP. The beads were next introduced into a flow cell constructed with an aminosilane-coated coverslip that had been modified with an NHS-tetrazine ester reagent to covalently bind the TCO modified beads. The beads were allowed to settle to the surface and bind for about 15 minutes, and the bead density checked by optical microscopy. If higher bead density was required, more beads were flowed in and allowed to bind. Contents of the flow cell were "blocked" with SuperBlock (ThermoFisher Scientific) to minimize non-specific binding of reagents to the beads or background surfaces.

Prior to initiating the sequencing run, reagents were loaded into 15 mL conical tubes and connected to a fluidic manifold with reagent lines leading to the flow cell. The flow cell containing the bead array was mounted on a microscope equipped with a 20× objective, and then connected to the fluidic manifold. The flow cell was purged with wash reagent to equilibrate the beads and primed template nucleic acid with the starting reaction conditions. Sequencing was initiated using an automated protocol to control the order and timing of reagent delivery. In one case, the primer of the primed template nucleic acid contained an unblocked 3'-OH, but was converted to a blocked 3'-OH via the incorporation of an unlabeled aminooxy-dNTP. FIG. 1 shows a flow chart outlining an expanded workflow used in this Example. Rather than using four cycles of serial binding and washing steps, the procedure in this Example was illustrated using only two cycles.

The sequencing protocol employed a series of reagent deliveries to facilitate binding and washing of different nucleotide and labeled polymerase combinations within the flow cell. First, there was introduced into the flow cell a first binding reagent that included a Cy3-labeled Bst backbone polymerase and a first unlabeled nucleotide (dCTP, "dNTP (1)") at a 100 µM concentration in a solution that included 30 mM Tris-HCl (pH 8.0), 420 mM KCl, 160 mM potassium glutamate, 2 mM EuCl$_3$, and 0.01% Tween-20. After 30 seconds of contact within the flow cell, the first binding reagent was removed by flushing with a first wash solution containing Tris-HCl (pH 8.0), 220 mM KCl, 160 mM potassium glutamate, 0.01% Tween-20, 1 mM β-mercaptoethanol, 100 µg/ml BSA, 10 µM dNTP(1), and 2 mM EuCl$_3$. Next, there was introduced into the flow cell a second binding reagent that included a Cy5-labeled second Bst backbone polymerase, a second unlabeled nucleotide (dATP, "dNTP(2)") at a 100 µM concentration, and the first unlabeled nucleotide (dCTP) at a 10 µM concentration in a solution that included 30 mM Tris-HCl (pH 8.0), 420 mM KCl, 160 mM potassium glutamate, 2 mM EuCl$_3$, and 0.01% Tween-20. After 30 seconds of contact within the flow cell, the second binding reagent was removed by flushing with a second wash solution containing Tris-HCl (pH 8.0), 220 mM KCl, 160 mM potassium glutamate, 0.01% Tween-20, 1 mM β-mercaptoethanol, 100 µg/ml BSA, 2 mM EuCl$_3$, and 10 µM each of dNTP(2) and dNTP(1).

Figure 5:
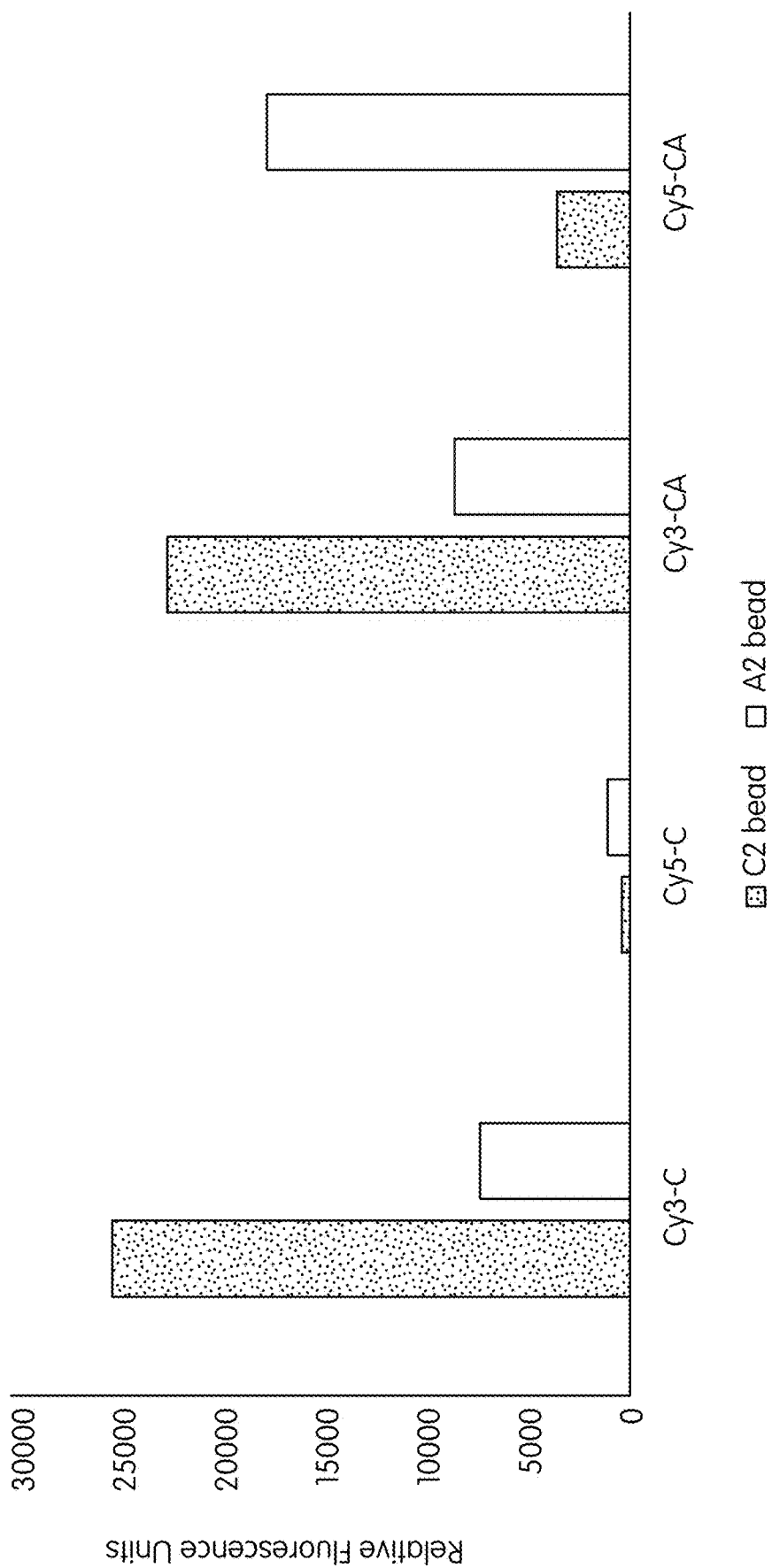
FIG. 5 presents a series of bar graphs showing relative fluorescence units (RFU) on the vertical axis for each of two different beads used in a sequencing procedure. Among each pair of graphs, the bar on the left (filled bar) represents a result obtained using a bead harboring immobilized primed template nucleic acid molecules having dCTP as the next correct nucleotide. The bar on the right (open bar) represents a result obtained using a bead harboring immobilized primed template nucleic acid molecules having dATP as the next correct nucleotide. Results indicate imaging following serial contacting steps using Cy3-labeled polymerase and dCTP (first contacting step); or Cy5-labeled polymerase and dCTP together with dATP (second contacting step).

Imaging was performed in two parts (see FIG. 5) to illustrate progress in the workflow, but optionally can be replaced by a single-scan imaging step at the conclusion of the binding and washing cycles. In a first imaging read, Cy3-labeled polymerase (delivered to the population in combination with dCTP) was detected in ternary complexes on the C2 bead (i.e., the correct target) at high levels, and at low levels on the A2 bead (i.e., the incorrect target). This indicated that dCTP was the cognate nucleotide for the primed template nucleic acid molecule on the C2 bead, and a non-cognate nucleotide for the primed template nucleic acid molecule on the A2 bead. Only very low backgrounds were observed in the Cy5 channel for each of the C2 and A2 beads in the absence of exposure of the population to the Cy5-labeled polymerase. A second imaging read followed exposure of the population to both Cy3-labeled polymerase (in combination with dCTP) and Cy5-labeled polymerase (in combination with both dATP and dCTP). Optical measurement using the Cy3 channel again indicated high level labeling of the C2 bead, and low level labeling of the A2 bead. This confirmed that dCTP was the cognate nucleotide for the primed template nucleic acid molecule on the C2 bead. Optical measurement using the Cy5 channel showed a low background signal for the C2 bead, and a high signal for the A2 bead, thereby indicating that dATP was the cognate nucleotide for the primed template nucleic acid molecule on the A2 bead. These aggregated results illustrated how a single imaging cycle could be used to detect a plurality of ternary complexes and identify cognate nucleotides on two different bead types among a population.

The results also demonstrated at least some level of polymerase exchange. Comparing the first and second imaging reads for binding of the Cy3-labeled polymerase in FIG. 5 indicates a low level of ternary complex dissociation and exchange over the extended period of the second binding step. More specifically, the slight decrease in signal for binding of Cy3-labeled polymerase between the first and second imaging reads indicated a low level of ternary complex dissociation, while the increased Cy5 signal associated with the C2 target in the second read suggested that polymerase from the second polymerase-nucleotide combination had formed a ternary complex with dCTP on targets that had lost the Cy3 polymerase by exchange. As discussed above, this is the basis of polymerase barcoding.

This invention has been described with reference to a number of specific examples and embodiments thereof. Of course, a number of different embodiments of the present invention will suggest themselves to those having ordinary skill in the art upon review of the foregoing detailed description. Thus, the true scope of the present invention is to be determined upon reference to the appended claims.

What is claimed is:

1. A method of distinguishing a first primed template nucleic acid from a second primed template nucleic acid in a first mixture, comprising
   (a) providing a first mixture comprising a population of different primed template nucleic acids attached to a solid support and a first stabilized ternary complex, the first stabilized ternary complex comprising a first primed template nucleic acid of the first mixture, a polymerase attached to a first type of label, and a first type of nucleotide;
   (b) removing any unbound polymerase attached to the first type of label from the first mixture, thereby forming a second mixture;
   (c) forming a second stabilized ternary complex by contacting the second mixture with a first reagent comprising a second type of nucleotide and a polymerase attached to a second type of label that is different from the first type of label, the second stabilized ternary complex comprising a second primed template nucleic acid of the first mixture, the polymerase of the first reagent, and the second type of nucleotide of the first reagent, thereby forming a third mixture comprising the first stabilized ternary complex and the second stabilized ternary complex, wherein the second type of nucleotide is different from the first type of nucleotide;
   (d) removing any unbound polymerase attached to the second type of label from the third mixture, thereby forming a fourth mixture; and
   (e) distinguishing the first primed template nucleic acid from the second primed template nucleic acid in the first mixture by detecting, in the fourth mixture, the first type of label and the second type of label.

2. The method of claim 1, wherein the first type of label is covalently attached to the polymerase of the first stabilized ternary complex.

3. The method of claim 2, wherein the second type of label is covalently attached to the polymerase of the second stabilized ternary complex.

4. The method of claim 1, wherein the first type of nucleotide and the second type of nucleotide are not distinguishably labeled with respect to each other.

5. The method of claim 4, wherein both the first type of nucleotide and the second type of nucleotide are unlabeled nucleotides.

6. The method of claim 1, wherein step (b) comprises contacting the first mixture with a wash solution comprising the first type of nucleotide.

7. The method of claim 1, wherein step (d) comprises contacting the third mixture with a wash solution comprising the first type of nucleotide and the second type of nucleotide.

8. The method of claim 1, wherein the first reagent further comprises the first type of nucleotide.

9. The method of claim 1, wherein the first type of nucleotide is not covalently attached to the first primed template nucleic acid in the first stabilized ternary complex of the second mixture, and wherein the second type of nucleotide is not covalently attached to the second primed template nucleic acid in the second stabilized ternary complex of the fourth mixture.

10. The method of claim 1, further comprising
    (f) forming a third stabilized ternary complex by contacting the fourth mixture with a second reagent comprising a third type of nucleotide and a polymerase attached to a third type of label that is different from the first type of label and the second type of label, the third stabilized ternary complex comprising a third primed template nucleic acid of the first mixture, the polymerase of the second reagent, and the third type of nucleotide of the second reagent, thereby forming a fifth mixture comprising the first stabilized ternary complex, the second stabilized ternary complex and the third stabilized ternary complex;
    (g) removing any unbound polymerase attached to the third type of label from the fifth mixture, thereby forming a sixth mixture; and
    (h) distinguishing the third primed template nucleic acid from the first primed template nucleic acid and the second primed template nucleic acid in the first mixture by detecting, in the sixth mixture, the third type of label.

11. The method of claim 10, wherein the third type of label is covalently attached to the polymerase of the third stabilized ternary complex.

12. The method of claim 10, wherein the first type of nucleotide, the second type of nucleotide and the third type of nucleotide are not distinguishably labeled with respect to each other.

13. The method of claim 10, wherein step (g) comprises contacting the fifth mixture with a wash solution comprising the first type of nucleotide, the second type of nucleotide and the third type of nucleotide.

14. The method of claim 10, wherein the second reagent further comprises the second type of nucleotide.

15. The method of claim 10, wherein the first type of nucleotide is not covalently attached to the first primed template nucleic acid in the first stabilized ternary complex of the sixth mixture; wherein the second type of nucleotide is not covalently attached to the second primed template nucleic acid in the second stabilized ternary complex of the sixth mixture, and wherein the third type of nucleotide is not covalently attached to the third primed template nucleic acid in the third stabilized ternary complex of the sixth mixture.

16. The method of claim 10, further comprising
    (i) forming a fourth stabilized ternary complex by contacting the sixth mixture with a third reagent comprising a fourth type of nucleotide and a polymerase attached to a fourth type of label that is different from the first type of label, the second type of label and the third type of label, the fourth stabilized ternary complex comprising a fourth primed template nucleic acid of the first mixture, the polymerase of the third reagent, and the fourth type of nucleotide of the third reagent, thereby forming a seventh mixture comprising the first stabilized ternary complex, the second stabilized ternary complex, third stabilized ternary complex and the fourth stabilized ternary complex;
    (j) removing any unbound polymerase attached to the fourth type of label from the seventh mixture, thereby forming an eighth mixture; and
    (k) distinguishing the fourth primed template nucleic acid from the first primed template nucleic acid, the second primed template nucleic acid and the third primed template nucleic acid in the first mixture by detecting, in the eighth mixture, the fourth type of label.

17. The method of claim 16, wherein the fourth type of label is covalently attached to the polymerase of the fourth stabilized ternary complex.

18. The method of claim 16, wherein the first type of nucleotide, the second type of nucleotide, the third type of nucleotide and the fourth type of nucleotide are not distinguishably labeled with respect to each other.

19. The method of claim 16, wherein step (j) comprises contacting the seventh mixture with a wash solution comprising the first type of nucleotide, the second type of nucleotide, the third type of nucleotide and the fourth type of nucleotide.

20. The method of claim 16, wherein the third reagent further comprises the third type of nucleotide.

21. The method of claim 16, wherein the first type of nucleotide is not covalently attached to the first primed template nucleic acid in the first stabilized ternary complex of the eighth mixture; wherein the second type of nucleotide is not covalently attached to the second primed template nucleic acid in the second stabilized ternary complex of the eighth mixture, wherein the third type of nucleotide is not covalently attached to the third primed template nucleic acid in the third stabilized ternary complex of the eighth mixture, and wherein the fourth type of nucleotide is not covalently attached to the fourth primed template nucleic acid in the fourth stabilized ternary complex of the eighth mixture.

* * * * *